US010329350B2

(12) United States Patent
Chou et al.

(10) Patent No.: US 10,329,350 B2
(45) Date of Patent: Jun. 25, 2019

(54) METHOD FOR PRODUCING A MULTIVALENT FAB FRAGMENT WITH COLLAGEN-LIKE PEPTIDE

(71) Applicant: INDUSTRIAL TECHNOLOGY RESEARCH INSTITUTE, Hsinchu (TW)

(72) Inventors: Min-Yuan Chou, Taipei (TW); Chuan-Chuan Huang, Hsinchu (TW); Hsiu-Chuan Li, Baoshan Township (TW); Ya-Ping Lai, Zhudong Township (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 347 days.

(21) Appl. No.: 13/761,569

(22) Filed: Feb. 7, 2013

(65) Prior Publication Data
US 2014/0178388 A1 Jun. 26, 2014

(30) Foreign Application Priority Data
Dec. 26, 2012 (TW) .............................. 101150029 A

(51) Int. Cl.
*C07K 16/28* (2006.01)
*C07K 16/46* (2006.01)
*A61K 39/00* (2006.01)

(52) U.S. Cl.
CPC ...... *C07K 16/2863* (2013.01); *C07K 16/2809* (2013.01); *A61K 2039/505* (2013.01); *C07K 2317/53* (2013.01); *C07K 2317/55* (2013.01); *C07K 2317/622* (2013.01); *C07K 2317/73* (2013.01); *C07K 2317/74* (2013.01); *C07K 2317/94* (2013.01); *C07K 2319/00* (2013.01); *C07K 2319/70* (2013.01)

(58) Field of Classification Search
None
See application file for complete search history.

(56) References Cited

U.S. PATENT DOCUMENTS

| 6,025,165 | A | 2/2000 | Whitlow et al. |
| 6,239,259 | B1 | 5/2001 | Davis et al. |
| 6,277,600 | B1 | 8/2001 | Tomita et al. |
| 6,511,663 | B1 | 1/2003 | King et al. |
| 2002/0018749 | A1* | 2/2002 | Hudson et al. ............... 424/1.49 |
| 2003/0027247 | A1* | 2/2003 | Wang ...................... C07K 16/00 435/69.1 |
| 2003/0138440 | A1 | 7/2003 | Fang et al. |
| 2003/0170230 | A1 | 9/2003 | Caterer et al. |
| 2008/0152586 | A1 | 6/2008 | Hudson et al. |
| 2008/0176247 | A1 | 7/2008 | Chou et al. |
| 2009/0324603 | A1* | 12/2009 | Cao ...................... A61K 51/103 424/142.1 |
| 2010/0136032 | A1 | 6/2010 | Weinberg et al. |
| 2011/0064653 | A1 | 3/2011 | Hansen et al. |
| 2012/0184716 | A1* | 7/2012 | Fischer ................. C07K 16/468 530/387.3 |

FOREIGN PATENT DOCUMENTS

| TW | 200922944 | 6/2009 |
| WO | WO2004/058821 | * 7/2004 |

OTHER PUBLICATIONS

Paul, Fundamental Immunology, 3rd Edition, 1993, pp. 292-295.*
Rudikoff et al. (Proceedings of the National Academy of Sciences USA, vol., 79, p. 1979, 1982).*
Wall et al., Theriogenology, vol. 45, p. 57-68, 1996.*
Houdebine et al., Journal of Biotechnology, vol. 34, p. 269-287, 1994.*
Kappell et al., Current Opinions in Biotechnology, vol. 3, p. 548-553, 1992.*
Invitrogen, pSecTag2/Hygro User Guide, p. 1-15, 2012.*
Arndt et al., "Antigen binding and stability properties of non-covalently linked anti-CD22 single-chain Fv dimers," FEBS Letters, vol. 578, 2004, pp. 257-261.
Charles et al., "Prevention of Human Rhinovirus Infection by Multivalent Fab Molecules Directed against ICAM-1," Antimicrobial Agents and Chemotherapy, vol. 47, No. 5, May 2003, pp. 1503-1508.
Fan et al., "Production of multivalent protein binders using a self-trimerizing collagen-like peptide scaffold," The FASEB Journal, vol. 22, Nov. 2008, pp. 3795-3804.
King et al., "Improved Tumor Targeting with Chemically Cross-Linked Recombinant Antibody Fragments," Cancer Research, vol. 54, Dec. 1, 1994, pp. 6176-6185.
Lawrence et al., "Orientation of antigen binding sites in dimeric and trimeric single chain Fv antibody fragments," FEBS Letters, vol. 425, 1998, pp. 479-484.
Luo et al., "Dimers and multimers of monoclonal IgG1 exhibit higher in vitro binding affinities to Fcgamma receptors," mAbs, Landes Bioscience, vol. 1, Issue 5, Sep./Oct. 2009, pp. 491-504.
Miller et al., "Design, Construction, and in Vitro Analyses of Multivalent Antibodies," The Journal of Immunology, vol. 170, 2003, pp. 4854-4861.
Miller et al., "Stability engineering of scFvs for the development of bispecific and multivalent antibodies," Protein Engineering, Design & Selection, vol. 23, No. 7, 2010, pp. 549-557.

(Continued)

*Primary Examiner* — Michael Allen
(74) *Attorney, Agent, or Firm* — Birch, Stewart, Kolasch & Birch, LLP

(57) ABSTRACT

The present invention relates to a method for producing multivalent Fab fragments. In particular, the invention relates to a method for the generation of trimeric Fab fragments by co-expression of a gene construct comprising a heavy chain portion of a Fab fragment and an in-frame fused collagen-like peptide, and a gene construct consisting of a light chain portion of an IgG in mammalian cells. Uses of molecules generated using the method of the invention are also described.

12 Claims, 20 Drawing Sheets

Specification includes a Sequence Listing.

(56) References Cited

OTHER PUBLICATIONS

Schoonooghe et al., "Efficient production of human bivalent and trivalent anti-MUCI Fab-scFv antibodies in Pichia pastoris," BMC Biotechnology, vol. 9, No. 70, Aug. 11, 2009, pp. 1-14.
Schott et al., "Preparation, Characterization, and in Vivo Biodistribution Properties of Synthetically Cross-Linked Multivalent Antitumor Antibody Fragments," Bioconjugate Chem, vol. 4, No. 2, 1993, pp. 153-165.

* cited by examiner

A

B

C

A

B

A

B

A

B

SEQUENCE LISTING

```
<160> NUMBER OF SEQ ID NOS: 32

<210> SEQ ID NO 1
<211> LENGTH: 297
<212> TYPE: PRT
<213> ORGANISM: Artificial Sequence
<220> FEATURE:
<223> OTHER INFORMATION: Synthetic heavy chain of h145FabCSA

<400> SEQUENCE: 1

Met Glu Thr Asp Thr Leu Leu Leu Trp Val Leu Leu Leu Trp Val Pro
1               5                   10                  15

Gly Ser Thr Gly Asp Glu Val Gln Leu Gln Glu Ser Gly Gly Gly Leu
            20                  25                  30

Val Gln Pro Gly Lys Ser Leu Lys Leu Ser Cys Glu Ala Ser Gly Phe
        35                  40                  45

Thr Phe Ser Gly Tyr Gly Met His Trp Val Arg Gln Ala Pro Gly Arg
    50                  55                  60

Gly Leu Glu Ser Val Ala Tyr Ile Thr Ser Ser Ser Ile Asn Ile Lys
65                  70                  75                  80

Tyr Ala Asp Ala Val Lys Gly Arg Phe Thr Val Ser Arg Asp Asn Ala
```

```
                     85                  90                  95
Lys Asn Leu Leu Phe Leu Gln Met Asn Ile Leu Lys Ser Glu Asp Thr
                100                 105                 110

Ala Met Tyr Tyr Cys Ala Arg Phe Asp Trp Asp Lys Asn Tyr Trp Gly
                115                 120                 125

Gln Gly Thr Met Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Lys Val Ala Ala Ala Glu Pro
225                 230                 235                 240

Lys Ser Gly Asp Lys Thr His Thr Cys Pro Pro Cys Pro Arg Ser Ile
                245                 250                 255

Pro Gly Pro Pro Gly Pro Pro Gly Pro Pro Gly Pro Pro Gly Pro Pro
            260                 265                 270

Gly Pro Pro Gly Pro Pro Gly Pro Pro Gly Pro Pro Gly Pro Pro Gly
            275                 280                 285

Ile Cys Asp Pro Ser Leu Cys Thr Gly
            290                 295

<210> SEQ ID NO 2
<211> LENGTH: 894
<212> TYPE: DNA
<213> ORGANISM: Artificial Sequence
<220> FEATURE:
<223> OTHER INFORMATION: Synthetic cDNA sequence encoding heavy chain of
      h145FabCSA

<400> SEQUENCE: 2
atggagacag acacactcct gctatgggta ctgctgctct ggttccaggt tccactggt        60 gatgaagtgc agctgcagga gtctggggga ggcttggtgc agcctggaaa gtccctgaaa     120
ctctcctgtg aggcctctgg attcaccttc agcggctatg catgcactg ggtccgccag      180 gctccaggga gggggctgga gtcggtcgca tacattacta gtagtagtat taatatcaaa     240
tatgctgacg ctgtgaaagg ccggttcacc gtctccagag acaatgccaa gaacttactg     300
tttctacaaa tgaacattct caagtctgag gacacagcca tgtactactg tgcaagattc     360
gactgggaca aaaattactg gggccaagga accatggtca ccgtctcctc agctagcacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgcggc cgctgagccc      720 aaatctggtg acaaaactca cacatgccca ccgtgcccaa gatctattcc tgggccacct     780
ggtcccccag gtcctccagg acccccaggg ccccccaggcc ccccgggcc gcctggaccc    840
```

```
ccagggccac caggcccccc aggcatctgc gacccatcac tatgtaccgg ttaa        894
```

<210> SEQ ID NO 3
<211> LENGTH: 235
<212> TYPE: PRT
<213> ORGANISM: Artificial Sequence
<220> FEATURE:
<223> OTHER INFORMATION: Synthetic light chain of h145FabCSA

<400> SEQUENCE: 3

```
Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ser Ser Leu
            20                  25                  30

Pro Ala Ser Leu Gly Asp Arg Val Thr Ile Asn Cys Gln Ala Ser Gln
        35                  40                  45

Asp Ile Ser Asn Tyr Leu Asn Trp Tyr Gln Gln Lys Pro Gly Lys Ala
    50                  55                  60

Pro Lys Leu Leu Ile Tyr Tyr Thr Asn Lys Leu Ala Asp Gly Val Pro
65                  70                  75                  80

Ser Arg Phe Ser Gly Ser Gly Ser Gly Arg Asp Ser Ser Phe Thr Ile
                85                  90                  95

Ser Ser Leu Glu Ser Glu Asp Ile Gly Ser Tyr Tyr Cys Gln Gln Tyr
            100                 105                 110

Tyr Asn Tyr Pro Trp Thr Phe Gly Pro Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 4
<211> LENGTH: 708
<212> TYPE: DNA
<213> ORGANISM: Artificial Sequence
<220> FEATURE:
<223> OTHER INFORMATION: Synthetic cDNA sequence encoding light chain of
      h145FabCSA

<400> SEQUENCE: 4

```
atggagacag acacactcct gctatgggta ctgctgctct ggttccaggt tccactggt        60 gatgacatcc agatgaccca gtctccatca tcactgcctg cctccctggg agacagagtc       120
actatcaatt gtcaggccag tcaggacatt agcaattatt taaactggta ccagcagaaa       180
ccagggaaag ctcctaagct cctgatctat tatacaaata aattggcaga tggagtccca       240
tcaaggttca gtggcagtgg ttctgggaga gattcttctt tcactatcag cagcctggaa       300
```

| | |
|---|---|
| tccgaagata ttggatctta ttactgtcaa cagtattata actatccgtg gacgttcgga | 360 |
| cctggcacca aggtggagat caagcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca agcagactac gagaaacac aaagtctacg cctgcgaagt cacccatcag | 660 |
| ggcctgagct cgcccgtcac aaagagcttc aacagggag agtgttag | 708 |

<210> SEQ ID NO 5
<211> LENGTH: 299
<212> TYPE: PRT
<213> ORGANISM: Artificial Sequence
<220> FEATURE:
<223> OTHER INFORMATION: Synthetic heavy chain of hOKT3FabCSA

<400> SEQUENCE: 5

Met Glu Thr Asp Thr Leu Leu Leu Trp Val Leu Leu Leu Trp Val Pro
1               5                   10                  15

Gly Ser Thr Gly Asp Gln Val Gln Leu Val Gln Ser Gly Gly Gly Val
            20                  25                  30

Val Gln Pro Gly Arg Ser Leu Arg Leu Ser Cys Lys Ala Ser Gly Tyr
        35                  40                  45

Thr Phe Thr Arg Tyr Thr Met His Trp Val Arg Gln Ala Pro Gly Lys
    50                  55                  60

Gly Leu Glu Trp Ile Gly Tyr Ile Asn Pro Ser Arg Gly Tyr Thr Asn
65                  70                  75                  80

Tyr Asn Gln Lys Val Lys Asp Arg Phe Thr Ile Ser Arg Asp Asn Ser
                85                  90                  95

Lys Asn Thr Ala Phe Leu Gln Met Asp Ser Leu Arg Pro Glu Asp Thr
            100                 105                 110

Gly Val Tyr Phe Cys Ala Arg Tyr Tyr Asp Asp His Tyr Cys Leu Asp
        115                 120                 125

Tyr Trp Gly Gln Gly Thr Pro Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Pro Gly Pro Gly Pro Gly Pro Gly Pro Pro Gly
            260                 265                 270

Pro Pro Gly Pro Pro Gly Pro Pro Gly Pro Pro Gly Pro Pro Gly Pro
        275                 280                 285

Pro Gly Ile Cys Asp Pro Ser Leu Cys Thr Gly

<210> SEQ ID NO 6
<211> LENGTH: 900
<212> TYPE: DNA
<213> ORGANISM: Artificial Sequence
<220> FEATURE:
<223> OTHER INFORMATION: Synthetic cDNA sequence encoding heavy chain of hOKT3FabCSA

<400> SEQUENCE: 6

```
atggagacag acacactcct gctatgggta ctgctgctct gggttccagg ttccactggt    60
gatcaggtgc agctggtgca gagcggcggc ggcgtggtgc agcctggcag gagcctgagg   120
ctgagctgca aggccagcgg ctacaccttc accaggtaca ccatgcactg ggtgaggcag   180
gcccctggca agggcctgga gtggatcggc tacatcaacc ctagcagggg ctacaccaac   240
tacaaccaga aggtgaagga caggttcacc atcagcaggg acaacagcaa gaataccgcc   300
ttcctgcaga tggacagcct gaggcctgag gacaccggcg tgtacttctg cgccaggtac   360
tacgacgacc actactgcct ggactactgg ggccagggca cccctgtgac cgtgagcagc   420
gctagcacca agggtccatc ggtcttcccc ctggcaccct cctccaagag cacctctggg   480
ggcacagcgg ccctgggctg cctggtcaag gactacttcc ccgaacctgt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
aaatcttgtg acaaaactca cacatgccca ccgtgcccag cacctgaact cctgggaggg   780
ccacctggtc ccccaggtcc tccaggaccc cagggccccc aggcccccc cgggccgcct   840
ggacccccag ggcaccagg ccccccaggc atctgcgacc atcactatg taccggttaa    900
```

<210> SEQ ID NO 7
<211> LENGTH: 234
<212> TYPE: PRT
<213> ORGANISM: Artificial Sequence
<220> FEATURE:
<223> OTHER INFORMATION: Synthetic light chain of hOKT3FabCSA

<400> SEQUENCE: 7

```
Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ser Ser Leu
                20                  25                  30

Ser Ala Ser Val Gly Asp Arg Val Thr Ile Thr Cys Ser Ala Ser Ser
            35                  40                  45

Ser Val Ser Tyr Met Asn Trp Tyr Gln Gln Thr Pro Gly Lys Ala Pro
        50                  55                  60

Lys Arg Trp Ile Tyr Asp Thr Ser Lys Leu Ala Ser Gly Val Pro Ser
65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Ser
                100                 105                 110

Ser Asn Pro Phe Thr Phe Gly Gln Gly Thr Lys Leu Gln Ile Thr Arg
            115                 120                 125

Thr Val Ala Ala Pro Ser Val Phe Ile Phe Pro Pro Ser Asp Glu Gln
        130                 135                 140
```

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
        180                 185                 190

Tyr Ser Leu Ser Ser Thr Leu Thr Leu Ser Lys Ala Asp Tyr Glu Lys
    195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 8
<211> LENGTH: 705
<212> TYPE: DNA
<213> ORGANISM: Artificial Sequence
<220> FEATURE:
<223> OTHER INFORMATION: Synthetic cDNA sequence encoding light chain of
      hOKT3FabCSA

<400> SEQUENCE: 8
atggagacag acacactcct gctatgggta ctgctgctct ggttccagg ttccactggt      60 gatgacatcc agatgaccca gagccctagc agcctgagcg ccagcgtggg cgacagggtg    120
accatcacct gcagcgccag cagcagcgtg agctacatga actggtacca gcagacccct    180
ggcaaggccc ctaagaggtg gatctacgac accagcaagc tggccagcgg cgtgcctagc    240
aggttcagcg gcagcggcag cggcaccgac tacaccttca ccatcagcag cctgcagcct    300
gaggacatcg ccacctacta ctgccagcag tggagcagca cccctttcac cttcggccag    360
ggcaccaagc tgcagatcac ccgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gttag                    705

<210> SEQ ID NO 9
<211> LENGTH: 241
<212> TYPE: PRT
<213> ORGANISM: Artificial Sequence
<220> FEATURE:
<223> OTHER INFORMATION: Synthetic polypeptide sequence of the 763
      single-chain Fv, 763scFv of 763scFv

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Phe Cys Gln His Phe Asp His Leu Pro Leu
                85                  90                  95
Ala Phe Gly Gly Gly Thr Lys Val Glu Ile Lys Gly Gly Gly Gly Ser
            100                 105                 110
Gly Gly Gly Gly Ser Gly Gly Gly Gly Ser Gln Val Gln Leu Gln Glu
        115                 120                 125
Ser Gly Pro Gly Leu Val Lys Pro Ser Glu Thr Leu Ser Leu Thr Cys
130                 135                 140
Thr Val Ser Gly Gly Ser Val Ser Ser Gly Asp Tyr Tyr Trp Thr Trp
145                 150                 155                 160
Ile Arg Gln Ser Pro Gly Lys Gly Leu Glu Trp Ile Gly His Ile Tyr
                165                 170                 175
Tyr Ser Gly Asn Thr Asn Tyr Asn Pro Ser Leu Lys Ser Arg Leu Thr
            180                 185                 190
Ile Ser Ile Asp Thr Ser Lys Thr Gln Phe Ser Leu Lys Leu Ser Ser
        195                 200                 205
Val Thr Ala Ala Asp Thr Ala Ile Tyr Tyr Cys Val Arg Asp Arg Val
    210                 215                 220
Thr Gly Ala Phe Asp Ile Trp Gly Gln Gly Thr Met Val Thr Val Ser
225                 230                 235                 240
Ser
```

<210> SEQ ID NO 10
<211> LENGTH: 723
<212> TYPE: DNA
<213> ORGANISM: Artificial Sequence
<220> FEATURE:
<223> OTHER INFORMATION: Synthetic cDNA sequence encoding polypeptide
      sequence of the 763 single-chain Fv, 763scFv of 763scFv

<400> SEQUENCE: 10

```
gacatccaga tgacccagag ccctagcagc ctgagcgcca gcgtgggcga cagggtgacc      60
atcacctgcc aggccagcca ggacatcagc aactacctga actggtacca gcagaagcct     120
ggcaaggccc ctaagctgct gatctacgac gccagcaacc tggagaccgg cgtgcctagc     180
aggttcagcg gcagcggcag cggcaccgac ttcaccttca ccatcagcag cctgcagcct     240
gaggacatcg ccacctactt ctgccagcac ttcgaccacc tgcctctggc cttcggcggc     300
ggcaccaagg tggagatcaa gggtggaggc ggttcaggcg aggtggctc tggcggtggc     360
ggatcgcagg tgcagctgca ggagagcggc cctggcctgg tgaagcctag cgagaccctg     420
agcctgacct gcaccgtgag cggcggcagc gtgagcagcg gcgactacta ctggacctgg     480
atcaggcaga gccctggcaa gggcctggag tggatcggcc acatctacta cagcggcaac     540
accaactaca accctagcct gaagagcagg ctgaccatca gcatcgacac cagcaagacc     600
cagttcagcc tgaagctgag cagcgtgacc gccgccgaca ccgccatcta ctactgcgtg     660
agggacaggg tgaccggcgc cttcgacatc tggggccagg gcaccatggt gaccgtgagc     720
agc                                                                   723
```

<210> SEQ ID NO 11
<211> LENGTH: 20
<212> TYPE: PRT
<213> ORGANISM: Artificial Sequence
<220> FEATURE:
<223> OTHER INFORMATION: Synthetic signal sequence

<400> SEQUENCE: 11

```
Met Glu Thr Asp Thr Leu Leu Leu Trp Val Leu Leu Leu Trp Val Pro
1               5                   10                  15

Gly Ser Thr Gly
            20

<210> SEQ ID NO 12
<211> LENGTH: 117
<212> TYPE: PRT
<213> ORGANISM: Artificial Sequence
<220> FEATURE:
<223> OTHER INFORMATION: Synthetic heavy chain variable region derived
      from the hamster anti-mouse CD3 antibody (145-2C11)

<400> SEQUENCE: 12

Asp Glu Val Gln Leu Gln Glu Ser Gly Gly Gly Leu Val Gln Pro Gly
1               5                   10                  15

Lys Ser Leu Lys Leu Ser Cys Glu Ala Ser Gly Phe Thr Phe Ser Gly
            20                  25                  30

Tyr Gly Met His Trp Val Arg Gln Ala Pro Gly Arg Gly Leu Glu Ser
        35                  40                  45

Val Ala Tyr Ile Thr Ser Ser Ser Ile Asn Ile Lys Tyr Ala Asp Ala
    50                  55                  60

Val Lys Gly Arg Phe Thr Val Ser Arg Asp Asn Ala Lys Asn Leu Leu
65                  70                  75                  80

Phe Leu Gln Met Asn Ile Leu Lys Ser Glu Asp Thr Ala Met Tyr Tyr
                85                  90                  95

Cys Ala Arg Phe Asp Trp Asp Lys Asn Tyr Trp Gly Gln Gly Thr Met
            100                 105                 110

Val Thr Val Ser Ser
        115

<210> SEQ ID NO 13
<211> LENGTH: 107
<212> TYPE: PRT
<213> ORGANISM: Artificial Sequence
<220> FEATURE:
<223> OTHER INFORMATION: Synthetic light chain variable region derived
      from the hamster anti-mouse CD3 antibody

<400> SEQUENCE: 13

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Asn Lys Leu Ala Asp Gly Val Pro Ser Arg Phe Ser Gly
    50                  55                  60

Ser Gly Ser Gly Arg Asp Ser Ser Phe Thr Ile Ser Ser Leu Glu Ser
65                  70                  75                  80

Glu Asp Ile Gly Ser Tyr Tyr Cys Gln Gln Tyr Tyr Asn Tyr Pro Trp
                85                  90                  95

Thr Phe Gly Pro Gly Thr Lys Val Glu Ile Lys
            100                 105

<210> SEQ ID NO 14
<211> LENGTH: 120
<212> TYPE: PRT
<213> ORGANISM: Artificial Sequence
```

```
<220> FEATURE:
<223> OTHER INFORMATION: Synthetic heavy chain variable region of the
      humanized muromonab-CD3 (Orthoclone OKT3)

<400> SEQUENCE: 14

Asp Gln Val Gln Leu Val Gln Ser Gly Gly Gly Val Val Gln Pro Gly
1               5                  10                  15

Arg Ser Leu Arg Leu Ser Cys Lys Ala Ser Gly Tyr Thr Phe Thr Arg
            20                  25                  30

Tyr Thr Met His Trp Val Arg Gln Ala Pro Gly Lys Gly Leu Glu Trp
        35                  40                  45

Ile Gly Tyr Ile Asn Pro Ser Arg Gly Tyr Thr Asn Tyr Asn Gln Lys
50                  55                  60

Val Lys Asp Arg Phe Thr Ile Ser Arg Asp Asn Ser Lys Asn Thr Ala
65                  70                  75                  80

Phe Leu Gln Met Asp Ser Leu Arg Pro Glu Asp Thr Gly Val Tyr Phe
                85                  90                  95

Cys Ala Arg Tyr Tyr Asp Asp His Tyr Cys Leu Asp Tyr Trp Gly Gln
            100                 105                 110

Gly Thr Pro Val Thr Val Ser Ser
            115                 120

<210> SEQ ID NO 15
<211> LENGTH: 107
<212> TYPE: PRT
<213> ORGANISM: Artificial Sequence
<220> FEATURE:
<223> OTHER INFORMATION: Synthetic light chain variable region of the
      humanized muromonab-CD3 (Orthoclone OKT3)

<400> SEQUENCE: 15

Asp Asp Ile Gln Met Thr Gln Ser Pro Ser Ser Leu Ser Ala Ser Val
1               5                  10                  15

Gly Asp Arg Val Thr Ile Thr Cys Ser Ala Ser Ser Ser Val Ser Tyr
            20                  25                  30

Met Asn Trp Tyr Gln Gln Thr Pro Gly Lys Ala Pro Lys Arg Trp Ile
        35                  40                  45

Tyr Asp Thr Ser Lys Leu Ala Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Trp Ser Ser Asn Pro Phe
                85                  90                  95

Thr Phe Gly Gln Gly Thr Lys Leu Gln Ile Thr
            100                 105

<210> SEQ ID NO 16
<211> LENGTH: 116
<212> TYPE: PRT
<213> ORGANISM: Artificial Sequence
<220> FEATURE:
<223> OTHER INFORMATION: Synthetic CH1 domain and a hinge region of
      human IgG1

<400> SEQUENCE: 16

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Ala Ala Ala Glu Pro Lys Ser Gly Asp Lys Thr His Thr Cys
                100                 105                 110

Pro Pro Cys Pro
            115
```

<210> SEQ ID NO 17
<211> LENGTH: 107
<212> TYPE: PRT
<213> ORGANISM: Artificial Sequence
<220> FEATURE:
<223> OTHER INFORMATION: Synthetic kappa light chain constant domain of
      IgG1

<400> SEQUENCE: 17

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 18
<211> LENGTH: 15
<212> TYPE: PRT
<213> ORGANISM: Homo sapiens
<220> FEATURE:
<221> NAME/KEY: misc_feature
<223> OTHER INFORMATION: hinge region of a human IgG

<400> SEQUENCE: 18

```
Glu Pro Lys Ser Gly Asp Lys Thr His Thr Cys Pro Pro Cys Pro
 1               5                  10                  15
```

<210> SEQ ID NO 19
<211> LENGTH: 15
<212> TYPE: PRT
<213> ORGANISM: Homo sapiens
<220> FEATURE:
<221> NAME/KEY: misc_feature
<223> OTHER INFORMATION: hinge region of a human IgG

<400> SEQUENCE: 19

```
Glu Pro Lys Ser Cys Asp Lys Thr His Thr Cys Pro Pro Cys Pro
 1               5                  10                  15
```

```
<210> SEQ ID NO 20
<211> LENGTH: 23
<212> TYPE: PRT
<213> ORGANISM: Homo sapiens
<220> FEATURE:
<221> NAME/KEY: misc_feature
<223> OTHER INFORMATION: hinge region of Human IgG1

<400> SEQUENCE: 20

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 21
<211> LENGTH: 19
<212> TYPE: PRT
<213> ORGANISM: Homo sapiens
<220> FEATURE:
<221> NAME/KEY: misc_feature
<223> OTHER INFORMATION: hinge region of Human IgG2

<400> SEQUENCE: 21

Glu Arg Lys Cys Cys Val Glu Cys Pro Pro Cys Pro Ala Pro Pro Val
1               5                   10                  15

Ala Gly Pro

<210> SEQ ID NO 22
<211> LENGTH: 25
<212> TYPE: PRT
<213> ORGANISM: Homo sapiens
<220> FEATURE:
<221> NAME/KEY: misc_feature
<223> OTHER INFORMATION: hinge region of Human IgG3

<400> SEQUENCE: 22

Glu Leu Lys Thr Pro Leu Gly Asp Thr Thr His Thr Cys Pro Arg Cys
1               5                   10                  15

Pro Ala Pro Glu Leu Leu Gly Gly Pro
            20                  25

<210> SEQ ID NO 23
<211> LENGTH: 20
<212> TYPE: PRT
<213> ORGANISM: Homo sapiens
<220> FEATURE:
<221> NAME/KEY: misc_feature
<223> OTHER INFORMATION: hinge region of Human IgG4

<400> SEQUENCE: 23

Glu Ser Lys Tyr Gly Pro Pro Cys Pro Ser Cys Pro Ala Pro Glu Phe
1               5                   10                  15

Leu Gly Gly Pro
            20

<210> SEQ ID NO 24
<211> LENGTH: 15
<212> TYPE: PRT
<213> ORGANISM: Artificial Sequence
<220> FEATURE:
<223> OTHER INFORMATION: Synthetic commonly used linker of scFv

<400> SEQUENCE: 24

Gly Gly Gly Gly Ser Gly Gly Gly Gly Ser Gly Gly Gly Gly Ser
1               5                   10                  15
```

```
<210> SEQ ID NO 25
<211> LENGTH: 16
<212> TYPE: PRT
<213> ORGANISM: Artificial Sequence
<220> FEATURE:
<223> OTHER INFORMATION: Synthetic glycine linker

<400> SEQUENCE: 25

Gly Gly Ser Gly Gly Ser Gly Gly Gly Ser Gly Gly Gly Gly Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic glycine linker

<400> SEQUENCE: 26

Arg Gly Arg Gly Arg Gly Arg Gly Arg Gly Arg Gly Gly Gly Ser
1               5                   10                  15

<210> SEQ ID NO 27
<211> LENGTH: 30
<212> TYPE: PRT
<213> ORGANISM: Artificial Sequence
<220> FEATURE:
<223> OTHER INFORMATION: Synthetic collagen-like peptide

<400> SEQUENCE: 27

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30

<210> SEQ ID NO 28
<211> LENGTH: 8
<212> TYPE: PRT
<213> ORGANISM: Artificial Sequence
<220> FEATURE:
<223> OTHER INFORMATION: Synthetic linker

<400> SEQUENCE: 28

Ala Ala Ala Gly Gly Gly Gly Ser
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic linker

<400> SEQUENCE: 29

Gly Gly Gly Gly Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Glycine-alanine linker

<400> SEQUENCE: 30

Gly Gly Ala Gly Ala Gly Ala Gly
```

```
<210> SEQ ID NO 31
<211> LENGTH: 30
<212> TYPE: PRT
<213> ORGANISM: Artificial Sequence
<220> FEATURE:
<223> OTHER INFORMATION: Synthetic collagen-like domain

<400> SEQUENCE: 31

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Ala Pro Glu Leu Leu Gly
1               5
```

METHOD FOR PRODUCING A MULTIVALENT FAB FRAGMENT WITH COLLAGEN-LIKE PEPTIDE

CROSS REFERENCE TO RELATED APPLICATIONS

This Application claims priority of Taiwan Patent Application No. 101150029, filed on Dec. 26, 2012, the entirety of which is incorporated by reference herein.

BACKGROUND

Functional affinity (avidity) is a measure of the overall binding strength of an antigen with many antigenic determinants. Polymerization of antigen-binding partners greatly increases their availability (or valency) for binding to a group of specific identical ligands in very close proximity to a target cell, resulting in greater target binding strength, slow dissociation rate and cross-linking effect which can prolong modulation of the ligands and facilitate biological potency.

A single-chain variable fragment (scFv) is a fusion protein of the variable regions of the heavy ($V_H$) and light chains ($V_L$) of immunoglobulins, linked by a short linker peptide. A major disadvantage of scFv, in comparison with the bivalent immunoglobulin G (IgG) counterpart, is the monovalency of the product, which precludes an increased avidity due to polyvalent binding. Several strategies have been developed for the multimerization of scFv in order to increase avidity.

Recombinant production of a trivalent single-chain antibody fragment (scFv) fusion protein by using a trimerization domain, including a C-propeptide of procollagens, a coiled-coil neck domain of collectin family proteins, a C-terminal portion of FasL and a bacteriophage T4 fibritin foldon domain (Hoppe, H. J., P. N. Barlow, et al. (1994). "A parallel three stranded alpha-helical bundle at the nucleation site of collagen triple-helix formation." FEBS Lett 344(2-3): 191-195; Frank, Kammerer et al. 2001 "Stabilization of short collagen-like triple helices by protein engineering." J Mol Biol 308(5): 1081-1089; Holler, N., A. Tardivel, et al. (2003). "Two adjacent trimeric Fas ligands are required for Fas signaling and formation of a death-inducing signaling complex." Mol Cell Biol 23(4): 1428-1440.) has been reported. A short alpha-helical collagen-like peptide capable of self-trimerization and propagation of the heterologous fusion proteins from either the C- or N-terminal direction has also been reported in EP1798240B1. The heterologous fusion domains used in EP1798240B1 were presented in scFv antibody fragments. However, there are disadvantages of scFv in multivalent formats for therapeutic applications.

Unlike immunoglobulin G (IgG) molecules which can be easily purified by affinity chromatographies on protein A or G-conjugated resins through binding to the Fc fragment of IgG, resulting in more than 98% in homogeneity of the product at the first step of purification scheme, purification of the multimeric scFv fusions for therapeutic applications is challenging work since no commercial affinity columns are available. Multivalent scFvs have significantly different stabilities depending on the specific variable domains from which they are constructed (Jung, S., A. Honegger, et al. (1999). "Selection for improved protein stability by phage display." J Mol Biol 294(1): 163-180; Worn, A. and A. Pluckthun (2001). "Stability engineering of antibody single-chain Fv fragments." J. Mol Biol 305(5): 989-1010). It has been reported that multimerization of a chimeric anti-CD20 single-chain Fv-Fc fusion protein is mediated through variable domain exchange, leading to heterogeneous antibody variants (Wu, A. M., G. J. Tan, et al. (2001). "Multimerization of a chimeric anti-CD20 single-chain Fv-Fc fusion protein is mediated through variable domain exchange." Protein Eng 14(12): 1025-1033).

CFY196 is composed of an Fab fragment of a humanized version of mAb 1A616 fused with a linker derived from human immunoglobulin D hinge and a tetramerization domain derived from the coiled-coil sequence of human transcription factor ATFα (Charles, Luo et al. 2003). However, ATFα is not a plasma-derived protein, which may associate with the risk of an immune response that could severely limit potential therapeutic applications.

U.S. Patent Application Publication U.S. 2008/0176247 demonstrates that an anti-CD3 scFv N-terminal fused to a self-trimerization collagen-like scaffold comprising GPP triplets is capable of forming a trimeric antibody fragment made up of three single-chain peptides. However, downstream purification of these trimeric scFv versions of collagen-like scaffold fusions was cumbersome since there is no available affinity resin to purify it efficiently. Additionally, the low protein expression level and the thermal instability of said trimeric scFv versions were not qualified to be used for biotherapeutics. Therefore, there is a need to design a new format of trimeric collagen scaffold antibodies.

SUMMARY

The present embodiments include a method for producing a multivalent Fab fragments in a eukaryotic cell including the steps of co-expressing in a eukaryotic cell:
(1) a gene construct coding for an amino acid sequence comprising a heavy chain portion of a Fab fragment and an in-frame fused collagen-like peptide; and,
(2) a gene construct coding for an amino acid sequence comprising a light chain variable region and the kappa light chain constant domain of human IgG.

In one embodiment the gene construct of (1) further comprises a sequence coding for a hinge region from human IgG.

In one embodiment the human IgG is selected from the group consisting of $IgG_1$, $IgG_2$, $IgG_3$, and $IgG_4$.

In one embodiment the sequence coding for the hinge region is located between the Fab fragment and the collagen-like peptide in the gene construct.

In one embodiment, the gene construct of (1) further comprises a sequence coding for a single chain Fv.

In one embodiment, the gene construct of (2) comprises a kappa light chain of human $IgG_1$.

Embodiments of the present invention include multivalent Fab fragment produced by the methods discussed above.

Another embodiment includes trimeric multivalent Fab fragment comprising three multivalent Fab fragments bound together by at least their collagen-like domains.

A further embodiment includes a multivalent antibody fragment comprising:
(1) an amino acid sequence comprising a heavy chain portion of a Fab fragment and an in-frame fused collagen-like peptide; and,
(2) an amino acid sequence comprising a light chain variable region and the kappa light chain constant domain of human IgG.

In one embodiment, the antibody fragment is bispecific.

A ligand for the multivalent antibody fragment of the embodiments discussed above, may be human CD3 or human CD3 and human epidermal growth factor receptor.

Another embodiment is a nucleic acid encoding the protein embodiments, expression vectors which express the protein embodiments, or host cells including the expression vector and/or nucleic acids.

The present invention provides a method of treating, preventing or ameliorating the symptoms of T cell-mediated immunological diseases, particularly autoimmune diseases, through the use of anti-CD3 antibody fragments. In particular, the methods of the invention provide for administration of antibodies that specifically bind the epsilon subunit within the human CD3 complex. Such antibodies modulate the T cell receptor/alloantigen interaction and, thus, regulate the T cell mediated cytotoxicity associated with autoimmune disorders. Additionally, the invention provides for modification of the anti-CD3 antibodies such that they exhibit reduced or eliminated effector function and T cell activation as compared to non-modified anti-CD3 antibodies. Cytokine release syndrome is manifested by, for example, headache, nausea, vomiting, fever, myalgias, arthralgias and shaking and may be caused by increased serum levels of, for example, IL-2, IL-6, IL-10, TNFα, and IFNγ.

Figure 1:
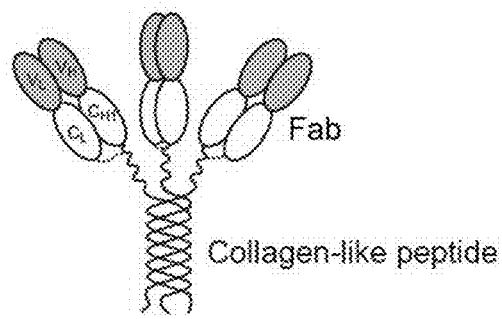
FIG. 1 depicts a schematic representation of different formats of antibody fragment molecules according to the embodiments: Format A: FabCSA, which is a trimeric antibody fragment consisting of a Fab fragment, in which the heavy chain fragment is fused with a hinge region and a collagen-like peptide capable of self-trimerization; Format B: FabCSA-scFv, which is a trimeric bispecific antibody fragment consisting of a Fab fragment and a single-chain antibody (scFv) at the N- and C-terminus of a collagen-like peptide capable of self-trimerization, respectively; and Format C: FabCSA-sdAb, which is a trimeric bispecific antibody fragment consisting of a Fab fragment and a single-domain antibody (sdAb) at the N- and C-terminus of a collagen-like peptide capable of self-trimerization, respectively.
Figure 1:
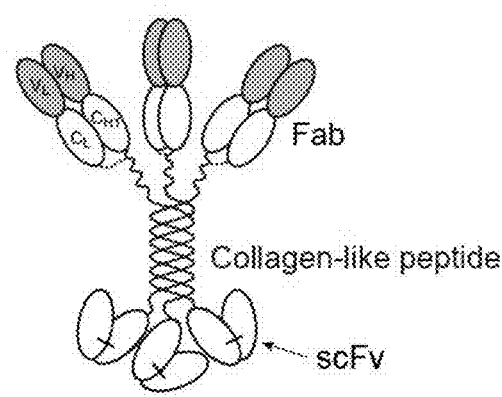
Figure 1:
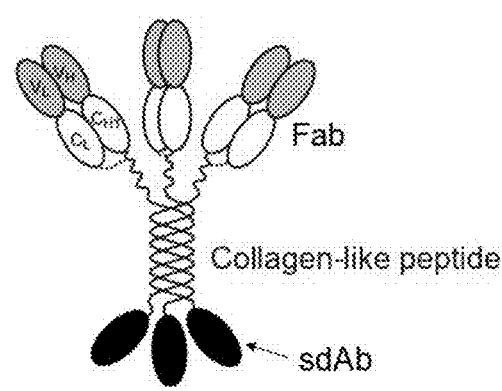

SCID mouse model. On day 0, two groups—763 IgG and PBS control, were inoculated subcutaneously with 5×10$^6$ HCT116 cells in the absence of human PBMC. The remaining three groups were subcutaneously inoculated with mixtures of 5×10$^6$ HCT116 cells and 5×10$^6$ unstimulated human PBMC from a healthy donor on day 0, followed by tail vein injection of PBS vehicle control (100 μl), 50 μg and 15 μg of hOKT3FabCSA763scFv on day 1 for 10 consecutive days. Tumor growth curves derived from each group with the indicated n numbers of animals are shown. Statistically significant differences (P<0.001) between the dosing of the hOKT3FabCSA763scFv groups and the unstimulated human PBMC control group are shown.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure includes a method for producing a multivalent antibody fragment in eukaryotic cells comprising expressing:

(1) a gene construct coding for an amino acid sequence comprising a heavy chain portion of an antibody fragment and an in-frame fused collagen-like peptide; and, (2) a gene construct coding for an amino acid sequence comprising a light chain variable region and the kappa light chain constant domain of human IgG.

The gene construct of (1) may also include a hinge region of an IgG and/or an scFv.

The multivalent antibody fragment described in the method above may then be assembled into a trimeric construct.

The present disclosure encompasses the nucleic acids encoding the multivalent antibody fragment and an expression vector expressing the multivalent antibody fragment when expressed in a host cell. The present disclosure also encompasses a host cell comprising an expression vector that expresses the multivalent antibody fragment.

The disclosure encompasses a method and kit for modulating (i.e., either inhibiting or augmenting) the biological activity of a ligand comprising incubating a trimer comprising three multivalent antibody fragments with the ligand.

The present disclosure also provides a method of treating, preventing or ameliorating the symptoms of T cell-mediated immunological diseases, particularly autoimmune diseases, through the administration multivalent anti-CD3 antibody fragments.

Definitions

1. Antibody Fragment

The multivalent antibody fragment of this disclosure includes one or more "antibody fragments" also described as an "antibody region," "antibody domain" or "antigen binding domain." The "antibody fragment" as discussed herein comprises a portion of an intact antibody, like the antigen binding or variable region of an intact antibody. Examples of antibody fragments include Fab, Fab', F(ab')$_2$, and Fv fragments; diabodies; linear antibodies (see U.S. Pat. No. 5,641, 870, Example 2; Zapata et al., Protein Eng. 8(10): 1057-1062 [1995]), single-chain antibody molecules, and multispecific antibodies.

Papain digestion of antibodies produces two identical antigen-binding fragments, called "Fab" fragments, and a residual "Fc" fragment, a designation reflecting the ability to crystallize readily.

The Fab fragment may include an entire L chain along with the variable region domain of the H chain ($V_H$), and the first constant domain of one heavy chain ($C_{H1}$). The constant region of the light chain could be of either lambda or kappa type. Each Fab fragment is monovalent with respect to antigen binding, i.e., it has a single antigen-binding site.

Fd or Fd fragment is the antibody heavy chain fragment consisting of $V_H$ and $C_{H1}$ domains.

Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_{H1}$ domain including one or more cysteines from the antibody hinge region.

The present multivalent antibody fragments may include a portion of the heavy chain, the light chain (or a portion thereof) or both the portion of a heavy chain, and either the light chain or a portion thereof.

The antibody fragment may include a single-chain Fv. "Single-chain Fv" also abbreviated as "sFv" or "scFv" are antibody fragments that comprise the $V_H$ and $V_L$ antibody domains connected into a single polypeptide chain. In one embodiment, the scFv polypeptide further comprises a polypeptide linker between the $V_H$ and $V_L$ domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994); Borrebaeck 1995, infra.

"Single domain" antibodies (sdAb) are antibodies whose complementary determining regions are part of a single domain polypeptide. Examples include heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, shark, goat, rabbit, and bovine.

"Bispecific antibodies" are antibodies that have binding specificities for at least two different antigens.

Fd-CS in the embodiments is a fusion polypeptide chain consisting of the antibody Fd fragment, followed by a hinge region of human IgG$_1$ and the collagen-like peptide of the invention.

The term "monomer" may be used herein to describe an embodiment of a multivalent antibody fragment having a single collagen like peptide. In one embodiment, "monomer" is used to describe a multivalent antibody fragment where a heavy chain and a light chair are associated. Said "monomers" are distinguished from the "trimerized" structure of the multivalent antibody fragments.

The multivalent antibody fragment in one embodiment is bispecific. In one embodiment, a monomeric structure of the invention may have more than antibody fragment, more than one antigen binding domain, and may bind more than one type of antigen. For instance, a single monomeric structure of the present multivalent antibody fragment may have a Fab region at the N terminal of the monomeric structure, and have an scFv region at the C terminal of the monomeric structure.

2. Hinge Region

The proteins of the embodiments of the present invention optionally include a "hinge region." In one embodiment, the hinge region is an approximately 4-15 amino acid long sequence. It may be the hinge region of a human IgG or a glycine linker. In one embodiment, the hinge region of a human IgG is the hinge region of human $IgG_1$, $IgG_2$, $IgG_3$ or human $IgG_4$.

As demonstrated previously by Fan, et al. (2008) "Production of multivalent protein binders using a self-trimerizing collagen-like peptide scaffold." FASEB J 22(11):3795-3804, the collagen-like peptide, $(GPP)_{10}$, by itself can drive the formation of a non-covalently bound trimeric fusion protein. Therefore, the "hinge region" is optional, and, even if present does not have a trimerizing effect on the claimed fusion peptides.

3. Collagen-Like Peptide

Collagen is the most abundant protein in mammals. It is an extracellular matrix protein that contains one or more triple-helical regions (collagenous domains or collagen "scaffolds") with a repeating triplet sequence of Gly-Xaa-Yaa, where Xaa and Yaa are any amino acid residues, with proline (amino acid code, P or Pro) as the residue most frequently incorporated. In the Yaa position, Pro is generally enzymatically modified to 4-hydroxyproline (amino acid code, O or Hyp), making Gly-Pro-Hyp the most common, as well as the most stabilizing, triplet in collagen. The presence of such triplets allows three collagen polypeptide chains (α-chains) to fold into a triple-helical conformation. Descriptions of collagen-like peptides can be found in the description of the collagen-like domains of U.S. patent application Ser. No. 13/588,752, which is hereby expressly incorporated by reference in its entirety. The collagen-like polypeptide of the invention by itself is capable of trimerizing a heavy chain portion of a Fab fragment into a trivalent structure, without other separate trimerization domains. A collagen-like polypeptide of the invention comprises at least one stretch of at least 5, at least 10, consecutive repeats of Gly-Pro-Pro or Gly-Pro-Hyp triplets. Collagen-like peptides of the invention may include a Gly-Pro-Pro or Gly-Pro-Hyp motif and/or other Gly-Xaa-Yaa motif, where Xaa and Yaa are any amino acid residues. Collagen-like peptides of the invention can also include a perfect repeating Gly-Xaa-Yaa triplet, interrupted by a short imperfection, in which the first position of Gly or the third position of Yaa residue is missing, found in many naturally occurring collagens and proteins containing collagen-like domains.

The stability of collagen multimer structures can be determined by measuring the melting temperature of the trimers. Many studies have examined the melting temperatures/stability of G-P-X1 repeats. Frank et al., (2001); Persikov et al., (2000) Biochemistry 39, 14960-14967; Persikov et al., (2004) Protein Sci. 13: 893-902; and Mohs et al., (2007) J. Biol. Chem. 282: 29757-29765. Based on these studies, the stability of various repeat structures can be predicted.

4. Linker

The linker is a short peptide sequence which may optionally be placed in between the antibody fragment and the collagen-like peptide region or between the binding domain and the collagen-like peptide region. The scFv polypeptide also comprises a polypeptide linker between the $V_H$ and $V_L$ domains which enables the scFv to form the desired structure for antigen binding. In some embodiments, the linker in either instance is between 4 and 10 amino acids in length.

The present multivalent antibody fragments can bind a ligand in the binding domain. A ligand is a biomolecule which forms a complex with a binding domain of the present embodiments. The ligand may bind the binding through intermolecular forces at a certain functional affinity. In one embodiment, the multivalent antibody fragment has a functional affinity for its ligand of greater than $10^{-6}$ M. In one embodiment, multivalent antibody fragment has a functional affinity for its ligand of greater than $10^{-8}$ M. In one embodiment, the multivalent antibody fragment has a functional affinity for its ligand of greater than $10^{-10}$ M. In certain embodiments, the soluble trimeric or hexameric fusion protein has a functional affinity (or affinity) for its ligand between $10^{-7}$ M and $10^{-12}$ M, between $10^{-8}$ M and $10^{-11}$ M, between $10^{-7}$ M and $10^{-10}$ M, between $10^{-8}$ M and $10^{-10}$ M, and between $10^{-9}$ M and $10^{-10}$ M.

In one embodiment, the trimeric or hexameric protein constructed of the multivalent antibody fragments is a soluble protein. A soluble protein is one that is soluble under physiological conditions. In one embodiment, the soluble trimeric or hexameric construct of the multivalent antibody fragments is a secreted protein. A secreted fusion protein is one that is secreted by a cell. Secretion of a protein can be targeted by having a signal sequence or signal peptide on the polypeptide comprising the antibody domain.

Signal sequences may include:

(SEQ ID NO: 11)
MetGluThrAspThrLeuLeuLeuTrpValLeuLeuLeuTrpValProGlySerThrGly.

The signal peptide may be cleaved off during the expression, assembly, and/or secretion process. Mouse myeloma NS0 cells are a good expression system for recombinant collagen or collagen-like protein production and for the expression of the present fusion proteins. Additionally, CHO and CHO-S cells may be used for the recombinant collagen or collagen-like protein production and for the expression of the present fusion proteins.

The assembled trimers of the embodiments of present invention include three monomers; a first, second and third multivalent antibody fragment. In one embodiment, the above-described first, second, and third multivalent antibody fragments are substantially identical, having at least 75% (e.g., any number between 75% and 100%, inclusive, e.g., 75%, 76% . . . 95%, 96%, 97%, 98%, or 99%) sequence identity to one another. A complex formed by three identical multivalent antibody fragments is a homotrimer. The three multivalent antibody fragments can be functional equivalents. A "functional equivalent" refers to a polypeptide derivative of a common polypeptide, e.g., a protein having one or more point mutations, insertions, deletions, truncations, a fusion protein, or a combination thereof, and retaining substantially the ability to form a triple helix coil and the activity of the heterologous domain, such as binding to a ligand. In one embodiment there are three copies of a first monomer multivalent antibody fragment structure, and three copies of a second multivalent antibody fragment structure. In one embodiment there may be two copies of a first multivalent antibody fragment structure, two copies of a second multivalent antibody fragment structure, and two copies of a third polypeptide structure.

The percent identity can be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Figure 9:
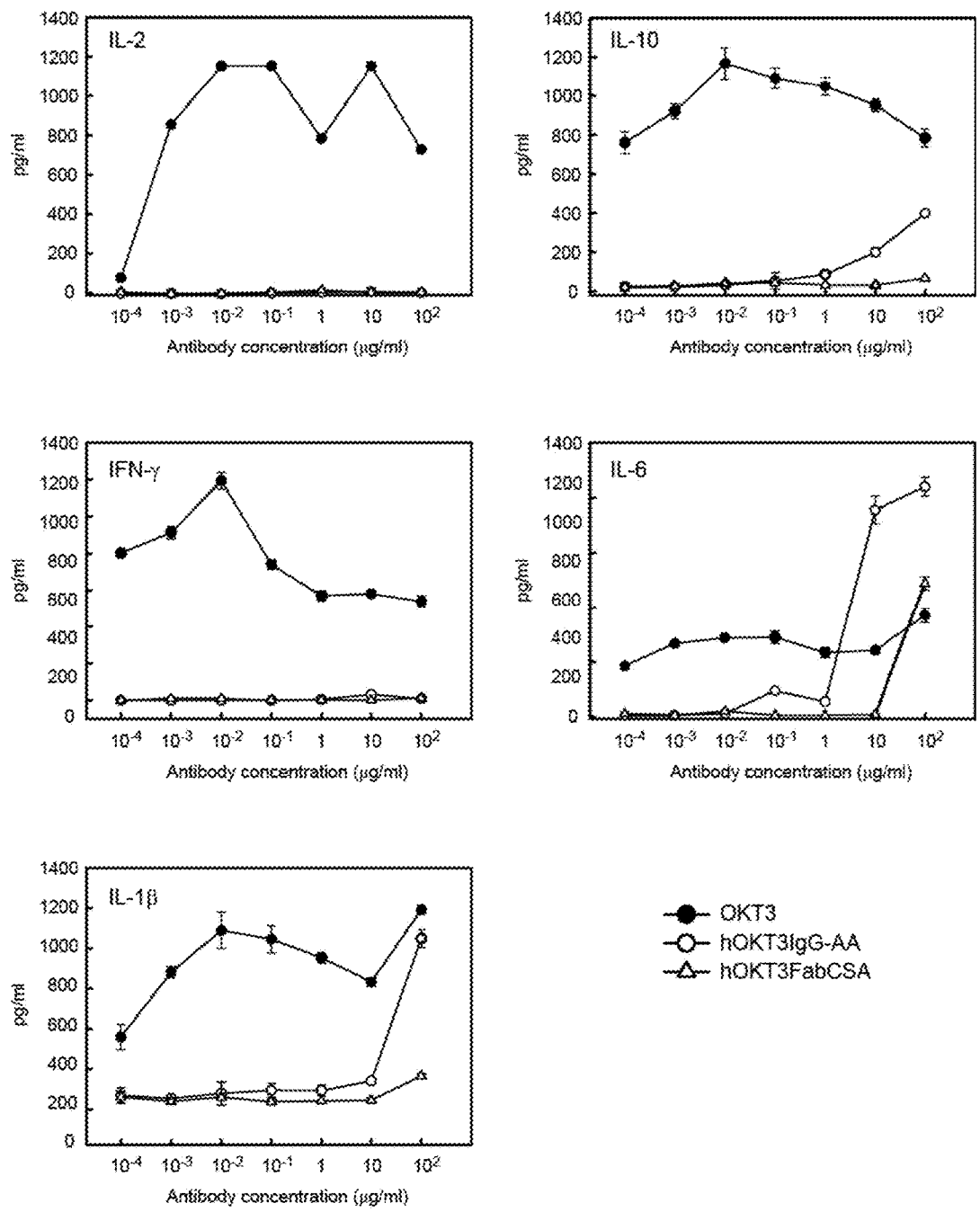
FIG. 9 depicts the releasing of cytokines induced by the purified OKT3, hOKT3IgG-AA and hOKT3FabCSA trimer. Human PBMCs were collected from three healthy normal donors and incubated individually with serial log dilutions of OKT3 (filled circles), hOKT3IgG-AA (open circles) or hOKT3FabCSA (open triangles). The levels of IL-2 and the rest of the indicated cytokines in the culture supernatants were determined by ELISA at 24- and 72-hour time points, respectively. Each point represents the mean±S.D. of three donors.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987; see also Richards et al., FIG. 9). In a family of proteins, each position in the consensus sequence is occupied by the amino acid occurring most frequently at that position in the family. If two amino acids occur equally frequently, either can be included in the consensus sequence.

A heterologous polypeptide, nucleic acid, or gene is a polypeptide, nucleic acid, or gene that is associated with another polypeptide, nucleic acid, or gene with which it is not naturally associated. Two fused domains or sequences are heterologous to each other if they are not adjacent to each other in a naturally occurring protein or nucleic acid.

An "isolated" polypeptide (or multivalent antibody fragment) or protein complex refers to a polypeptide or a protein complex substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide or protein complex of the embodiments of the invention can be purified from a natural source, produced by recombinant DNA techniques.

The three monomeric antibody fragments that trimerize to form trimeric multivalent antibody fragments may be non-contiguous. In another embodiment, the three monomeric antibody fragments that trimerize to form a trimeric multivalent antibody fragment are contiguous, i.e., translated as a single translation product.

On the one hand, when two or more of the six binding domains are identical to each other, the protein complex can have 1-3 binding domains that are specific for one binding partner (e.g., antigen) in comparison with a conventional antibody or receptor, which has only one or two such domains. In other words, unlike a conventional antibody or receptor, which is only monovalent or divalent for an antigen, the protein complex can be di-, tri-, tetra-, penta-, or hexa-valent. As a result, it can be made to have affinities that are higher than a conventional antibody or receptor. Because of the higher affinities, smaller amounts of the protein complex and shorter incubation durations are needed than a conventional antibody to achieve the desired goals, for example, therapeutic effects, thereby lowering treatment costs and minimizing side effects (e.g., unwanted immune responses).

On the other hand, when two or more of the six domains are different from each other, a protein complex of this invention can have 2-6 binding domains that are specific for 2-6 different binding partners. Unifying multiple binding partner sites of different specificities into one unit, it has the ability to bring together multiple binding partners and therefore have desirable uses in therapy, tissue reconstruction, and assembly of active protein machinery (e.g., a multi-subunit enzyme) at the nanometer level.

A protein complex of the embodiments of this invention may be conjugated to a therapeutic moiety such as a cytotoxin, a therapeutic agent, or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, and 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Radioactive ions contemplated in embodiments of the invention include, but are not limited to, $^{111}$Indium, $^{113}$Indium, $^{99}$Rhenium, $^{105}$Rhenium, $^{101}$Rhenium, $^{99}$Mtechnetium, $^{121}$Mtellurium, $^{122}$Mtellurium, $^{125}$Mtelliurunm, $^{165}$Thulium, $^{167}$Thulium, $^{168}$Thulium, $^{123}$Iodine, $^{125}$Iodine, $^{126}$Iodine, $^{131}$Iodine, $^{133}$Iodine, $^{81}$Krypton, $^{33}$Xenon, $^{90}$Yttrium, $^{213}$Bismuth, $^{77}$Bromine, $^{18}$Fluorine, $^{95}$Ruthenium, $^{97}$Ruthenium, $^{103}$Ruthenium, $^{105}$Ruthenium, $^{107}$Mercury, $^{203}$Mercury, $^{67}$Gallium, $^{68}$Gallium, $^{35}$Sulphur, and $^{14}$Carbon.

The conjugates can be used for modifying a given biological response by administering the conjugate to a host. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

In additional embodiments, a multivalent antibody (or its trimer complex) may be conjugated to or bound to a labeling agent (i.e. "a marking agent"), such as fluorescent agents or radioactive agents. Marker proteins include, but are not limited to, luciferase, green fluorescent protein, and enhanced green fluorescent protein. Multivalent antibodies of the present embodiments that include marker proteins can be used in diagnostic and molecular imaging. In embodiments of the invention, multivalent antibody fragments that include marker proteins or radioactive ions, or other fusion moieties, can be packaged in a kit including the multivalent antibody fragment and other reagents necessary for imaging of specific molecules. These reagents can include, but are not limited to, reagents for the preparation of biological samples and reagents for the visualization of the marker protein.

In further embodiments of the invention, a multivalent antibody fragment (or its trimer complex) can be conjugated to a polymer. Such polymers include, but are not limited to polyethylene glycol, polypropylene glycol, and polyoxyethylated polyol.

The embodiments of the invention also encompass an isolated nucleic acid that contains a sequence encoding the just-mentioned multivalent antibody fragment or a complement of the sequence. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but in one embodiment is double-stranded DNA. An "isolated nucleic acid" is a nucleic acid, the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of a vector include a plasmid, cosmid, or viral vector. The vector of this invention includes a nucleic acid in a form suitable for expression of the nucleic acid in a host cell. The vector includes one or more regulatory sequences operatively linked to the nucleic acid sequence to be expressed. In one embodiment the expression vector is pSecTag2/Hygro (Invitrogen).

A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of the embodiments of the invention is a host cell that contains the above-described nucleic acid. Examples include E. coli cells, insect cells (e.g., using Drosophila S2 cells or baculovirus-infected insect cells), yeast cells, or mammalian cells (e.g., mouse myeloma NS0 cell). See e.g., Goeddel, (1990) Gene Expression Technology: Methods in Enzymology 185, Academic Press, San Diego, Calif.

The sequences encoding the present monomer structures may also include nucleotide or protein sequences allowing for identification and purification. Such sequences can include restriction sites, tags, spacers, and other methods to purify or identify the nucleotide or protein sequence. Often such sequences are included in the nucleotide, and code for short amino acid sequences of 4-6 amino acids in length. They often appear in-between domains of the multivalent antibody fragment as artifacts, but do not materially affect the basic and novel characteristics of the invention.

To produce a multivalent antibody fragment, one can culture a host cell in a medium under conditions permitting expression of the polypeptide encoded by a nucleic acid, and purify the polypeptide from the cultured cell or the medium of the cell. Peptides containing collagen-like peptides can be difficult to purify if there are no affinity tags. In the present multivalent antibody fragments, the Fab region assists with purification. Alternatively, the nucleic acid of this invention can be transcribed and translated in vitro, for example, using T7 promoter regulatory sequences and T7 polymerase.

To produce a protein complex of the embodiments of this invention, one can culture a host cell containing a first, second, and third nucleic acids respectively encoding the above-mentioned first, second, and third fusion polypeptides in a medium under a condition permitting expression of polypeptides encoded by the three nucleic acids and formation of a triple helix coil between the expressed polypeptides, and purifying the protein complex from the cultured cell or the medium of the cell. The host cell is a eukaryotic cell containing an enzymatic activity that hydroxylates a proline residue.

A host cell can be any prokaryotic or eukaryotic cell. The proteins of the embodiments of the invention can be expressed in bacterial cells (such as E. coli), insect cells, yeast, or mammalian cells (such as Chinese hamster ovary cells (CHO) or COS cells (African green monkey kidney cells CV-1 origin SV40 cells; Gluzman (1981) Cell 23:175 182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

For in vivo use in a human, a multivalent antibody fragment of the embodiments of the invention is of human origin. For example, it can include a sequence fused in-frame to a collagen-like domain of human origin. Since many collagen-like proteins with collagenous domains are fairly stable in the blood, the multivalent antibody fragments should retain structural integrity in blood as well. Furthermore, the hinge region and Fc domains can be taken from a human IgG or humanized antibody.

The present embodiments of the invention also provides a method of treating, preventing or ameliorating the symptoms of T cell-mediated immunological diseases, particularly autoimmune diseases, through the use of multivalent anti-CD3 antibody fragments. In particular, the methods of the invention provide for administration of multivalent antibody fragments or antibodies that specifically bind the epsilon subunit within the human CD3 complex. Such antibodies and antibody fragments modulate the T cell receptor/alloantigen interaction and, thus, regulate the T cell mediated cytotoxicity associated with autoimmune disorders. Additionally, the invention provides for modification of the anti-CD3 antibodies or anti-CD3 antibody fragments such that they exhibit reduced or eliminated effector function and T cell activation as compared to non-modified anti-CD3 antibodies.

Autoimmune disorders refer to diseases wherein the immune system mistakenly attacks and destroys healthy body tissue, thereby producing tissue injury. Autoimmune disorders include, but are not limited to, rheumatoid arthritis, juvenile rheumatoid arthritis, ankylosing spondylitis, multiple sclerosis, type 1 diabetes mellitus, inflammatory bowel diseases, systemic lupus erythematosus, mixed connective tissue disease, progressive systemic scleroderma, antiphospholipid syndrome, psoriasis, scleroderma, glomerulonephritis, dermatomyositis, Hashimoto's thyroiditis and Grave's disease.

Effector function may be demonstrated by phagocytosis and collapse of an antibody-coated particle through complement-dependent cytotoxicity (CDC), lysis of an antibody-coated target cell by crosslinking the antibody Fc fragment with the Fcγ receptors of an activated effector cell, such as natural killer cells, through antibody-dependent cell-mediated cytotoxicity (ADCC), cell membrane rupture, release of an inflammatory mediator, including IL-1α, IL-1β, IL-6, and TNFα, and control of immunoglobulin production.

T cell activation may be demonstrated by measuring T cell proliferation upon stimulation of T cells via antigen or agonistic antibodies to T cell receptor (TCR). TCR activation can lead to the initiation of signaling pathways including induction of specific protein tyrosine kinases (PTKs), breakdown of phosphatidylinositol 4,5-biphosphate (PIP2), activation of protein kinase C (PKC) and elevation of intracellular calcium ion concentration. These early events are transmitted to the nucleus and result in clonal expansion of T cells; upregulation of activation markers on the cell surface; differentiation into effector cells; induction of cytotoxicity or cytokine secretion such as IL-2; induction of apoptosis.

Cytokine release syndrome is manifested by, for example, headache, nausea, vomiting, fever, myalgias, arthralgias and shaking and may be caused by increased serum levels of, for example, IL-1α, IL-1β, IL-2, IL-6, IL-10, TNFα, and IFNγ.

The above-described protein complexes, based on the specificity of the heterologous binding domains, can be used for treating various disorders, including autoimmune disorders, inflammation diseases, metabolism diseases, fibrosis diseases, cancer, and cardiovascular diseases. Specific manifestations of the diseases include headache, nausea, vomiting, fever, myalgias, arthralgias and shaking and may be caused by increased serum levels of, for example, IL-2, IL-6, IL-10, TNFα, and IFNγ. The invention therefore features a method of treating such a disorder, e.g., by administering to a subject in need thereof an effective amount of a protein complex of the invention to treat the disorder. Subjects to be treated can be identified as having, or being at risk for acquiring, a condition characterized by the disorder. This method can be performed alone or in conjunction with other drugs or therapy.

One embodiment is used for treating disorders caused by or exacerbated by T cell receptor/alloantigen interaction, and thus, regulate the T cell mediated toxicity associated with autoimmune disorders. In another embodiment, the present invention is used for modulating the biological activity of CD3, modulating the level of CD3 signaling, or modulating the T cell receptor/alloantigen interaction in a patient in need thereof. In an embodiment, the present invention decreases the level of unbound CD3 or CD3 signaling.

Because of the multi-specific feature of a protein complex of this invention, one can use it to bridge molecules or cells that are normally are not associated with each other. This feature is particularly useful for cell-based therapies. In one example, the present multivalent Fab antibody fragments are capable of binding CD3 with one domain, while another domain binds EGFR.

Activation of the cytotoxic T cell may occur via binding of the CD3 antigen as an effector antigen on the surface of the cytotoxic T cell by a protein complex of the invention. Other lymphoid cell-associated effector antigens include the human CD16 antigen, NKG2D antigen, NKp46 antigen, CD2 antigen, CD28 antigen, CD25 antigen, CD64 antigen, and CD89 antigen. Binding to these effector antigens leads to activation of effector cells such as monocytes, neutrophilic granulocytes, and dendritic cells. These activated cells then exert a cytotoxic or an apoptotic effect on target cells.

The term "treating" is defined as administration of a composition to a subject with the purpose to cure, alleviate, relieve, remedy, prevent, or ameliorate a disorder, the symptom of the disorder, the disease state secondary to the disorder, a disorder which is exacerbated by the ligand of the present protein, or the predisposition toward the disorder. An "effective amount" is an amount of the composition that is capable of producing a medically desirable result, e.g., as described above, in a treated subject.

In one in vivo approach, a therapeutic composition (e.g., a composition containing a protein complex the invention) is administered to a subject. Generally, the complex is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Suitable dosages are in the range of 0.01-100.0 mg/kg or more specifically 0.1-100, 0.1-75, 0.1-50, 0.1-25, 0.1-10, 0.5-100, 0.5-75, 0.5-50, 0.5-25, 0.5-10, 1-100, 1-75, 1-50, or 1-25 mg/kg. The dosages may include 1-10, 10-100, 10-75, 10-50, 10-25, 25-50, 50-75, 25-100, 25-50, 50-100, or 75-100 mg/kg. Or dosages can range from 1-2, 3-4, 5-6, 7-8, or 9-10 mg/kg.

Therapeutic compositions of the embodiments of the invention can be administered daily, one time, two times, or three times or more per week for between about 1 to 10 weeks, like between 2 to 8 weeks, or between about 3 to 7 weeks, and even for about 4, 5, or 6 weeks. Variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

The pharmaceutically acceptable carrier includes a solvent, a dispersion medium, a coating, an antibacterial and antifungal agent, and an isotonic and absorption delaying agent. Specifically, these agents can include saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH of the pharmaceutical composition can be adjusted with acids or bases, such as hydrochloric acid or sodium hydroxide.

Also within the scope of the embodiments of the invention is a pharmaceutical composition that contains a pharmaceutically acceptable carrier and an effective amount of a protein complex of the embodiments of the invention. The pharmaceutical composition can be used to treat the disorders listed above. The pharmaceutically acceptable carrier includes a solvent, a dispersion medium, a coating, an antibacterial and antifungal agent, and an isotonic and absorption delaying agent. The pharmaceutical composition can be formulated into dosage forms for different administration routes utilizing conventional methods.

The efficacy of a composition of the embodiments of the invention can be evaluated both in vitro and in vivo. For in vivo studies, the composition can be injected into an animal (e.g., a mouse model) and its therapeutic effects are then accessed. Based on the results, an appropriate dosage range and administration route can be determined.

As used herein, the terms "directed against" and "specifically binds to" mean that the present fusion protein comprises an antibody domain, where the antibody or fragment of an antibody has a functional affinity of at least $10^{-6}$ M for its ligand.

The details of one or more embodiments of the invention are set forth in the accompanying drawing and the description below. Other features, objects, and advantages of the invention will be apparent from the description and drawing, and from the claims.

II. Structure of Embodiments

A. Antibody Fragment

A monomer of the present multivalent antibody fragment according to one embodiment may have a single antibody fragment (including a binding domain/region or antigen-binding fragment) or more than one antibody fragment. Examples of antibody fragments of the a monomer present multivalent antibody fragments include, but are not limited to: (i) a Fab fragment, a monovalent fragment consisting of the $V_L$, $V_H$, $C_L$, and $C_{H1}$ domains; (ii) a F(ab)$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated complementarity determining region (CDR); and (vii) $V_L$ or $V_H$ domains. In one embodiment, the antibody fragment is a Fab fragment.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain Fv (scFv); see e.g., Bird et al. (1988) Science 242:423-426; and Huston et al. (1988) Proc. Natl. Acad. Sci. USA 85:5879-5883). Such single-chain antibodies (scFv) are also encompassed within the term "antigen-binding fragment" of an antibody. These antibody fragments can be obtained using conventional techniques known to those with skill in the art, and the fragments are screened for utility in the same manner as are intact antibodies.

In one embodiment, the antibody fragment is an scFv.

In one embodiment, the multivalent antibody includes two antibody fragments, a Fab and an scFv.

Fd or Fd fragment is the antibody heavy chain fragment consisting of $V_H$ and $C_{H1}$ domains.

An antibody can be a monoclonal antibody. In one embodiment, the antibody can be recombinantly produced, e.g., produced by phage display or by combinatorial methods. Phage display and combinatorial methods for generating antibodies are known in the art (see e.g., Ladner et al. U.S. Pat. No. 5,223,409; Kang et al. International Publication No. WO 92/18619; Dower et al. International Publication No. 25 WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9: 1370-1372; Hay et al. (1992) Hum Antibod Hybridomas 3: 81-85; Huse et al. (1989) Science 246: 1275-1281; Griffths et al. (1993) EMBO J. 12: 725-734; Hawkins et al. (1992) J Mol Biol 226: 889-896; Clackson et al. (1991) Nature 352: 624-628; Gram et al. (1992) Proc Natl Acad Sci USA 89: 3576-3580; Garrad et al. (1991) Bio/Technology 9: 1373-1377; Hoogenboom et al. (1991) Nuc Acid Res 19: 41334137; and Barbas et al. (1991) Proc Natl Acad Sci USA 88: 7978-7982, the contents of all of which are incorporated by reference herein). In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), or camel antibody. In one embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT 15 publication WO 91/10741; Lonberg et al. International Application WO 92/03918; Kay et al. International Application 92/03917; Lonberg, et al. (1994) Nature 368: 856-859; Green, L. L. et al. (1994) Nature Genet. 7: 13-21; Morrison et al. (1994) Proc. Natl. Acad. Sci. USA 81: 6851-6855; Bruggeman et al. (1993) Year Immunol 7: 33-40; Tuaillon et al. (1993) Proc. Natl. Acad. Sci. USA 90: 3720-3724; Bruggeman et al. (1991) Eur J Immunol 21: 1323-1326).

One example of a human monoclonal antibody is panitumumab (VECTIBIX®), formerly ABX-EGF, is a fully human monoclonal antibody specific to the epidermal growth factor receptor (EGFR). Panitumumab is used to treat patients with EGFR-expressing, metastatic cancer of the colon or rectum.

An antibody can be one in which the variable region, or a portion thereof, e.g., the CDR's, are generated in a non-human organism, e.g., a rat or mouse. Chimeric, CDR-grafted, and humanized antibodies can be used. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184, 187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988) Science 240: 1041-1043); Liu et al. (1987) Proc. Natl. Acad. Sci. USA 84: 3439-3443; Liu et al., (1987) J Immunol. 139:3521-3526; Sun et al. (1987) Proc. Natl. Acad. Sci. USA 84: 214-218; Nishimura et al., (1987) Canc. Res. 47: 999-1005; Wood et al. et al (1985) Nature 314: 446-449; and Shaw et al., (1988) J. Natl Cancer Inst. 80: 1553-1559).

A humanized or CDR-grafted antibody will have at least one or two but generally all three recipient CDR's (of heavy and/or light immunoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody or a fragment thereof. The donor may be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, or 90%, 95%, 99% or higher identical thereto.

In one embodiment, the ligand or antigen is CD3. In one embodiment the ligand or antigen is EGFR. In one embodiment a bispecific structure has both anti-CD3 regions and anti-EGFR regions.

In one embodiment, the Fab is anti-CD3 and may include one or more of the following structures:

Binding Regions Included in h145FabCSA

The binding region of an antibody fragment may be derived from an anti-CD3 antibody, and may include both the heavy and light chains. For instance, the heavy chain variable region derived from the hamster anti-mouse CD3 antibody (145-2C11) is:

(SEQ ID NO: 12)
AspGluValGlnLeuGlnGluSerGlyGlyGlyLeuValGlnProGly

LysSerLeuLysLeuSerCysGluAlaSerGlyPheThrPheSerGly

-continued
TyrGlyMetHisTrpValArgGlnAlaProGlyArgGlyLeuGluSer

ValAlaTyrIleThrSerSerSerIleAsnIleLysTyrAlaAspAla

ValLysGlyArgPheThrValSerArgAspAsnAlaLysAsnLeuLeu

PheLeuGlnMetAsnIleLeuLysSerGluAspThrAlaMetTyrTyr

CysAlaArgPheAspTrpAspLysAsnTyrTrpGlyGlnGlyThrMet

ValThrValSerSer

The light chain variable region derived from the hamster anti-mouse CD3 antibody (145-2C11) is:

(SEQ ID NO: 13)
AspIleGlnMetThrGlnSerProSerSerLeuProAlaSerLeuGly

AspArgValThrIleAsnCysGlnAlaSerGlnAspIleSerAsnTyr

LeuAsnTrpTyrGlnGlnLysProGlyLysAlaProLysLeuLeuIle

TyrTyrThrAsnLysLeuAlaAspGlyValProSerArgPheSerGly

SerGlySerGlyArgAspSerSerPheThrIleSerSerLeuGluSer

GluAspIleGlySerTyrTyrCysGlnGlnTyrTyrAsnTyrProTrp

ThrPheGlyProGlyThrLysValGluIleLys

Binding Regions Included in hOKT3FabCSA

The heavy chain variable region of the humanized muromonab-CD3 (Orthoclone OKT3 antibody) is:

(SEQ ID NO: 14)
AspGlnValGlnLeuValGlnSerGlyGlyGlyValValGlnProGly

ArgSerLeuArgLeuSerCysLysAlaSerGlyTyrThrPheThrArg

TyrThrMetHisTrpValArgGlnAlaProGlyLysGlyLeuGluTrp

IleGlyTyrIleAsnProSerArgGlyTyrThrAsnTyrAsnGlnLys

ValLysAspArgPheThrIleSerArgAspAsnSerLysAsnThrAla

PheLeuGlnMetAspSerLeuArgProGluAspThrGlyValTyrPhe

CysAlaArgTyrTyrAspAspHisTyrCysLeuAspTyrTrpGlyGln

GlyThrProValThrValSerSer

The light chain variable region of the humanized muromonab-CD3 (Orthoclone OKT3) is:

(SEQ ID NO: 15)
AspAspIleGlnMetThrGlnSerProSerSerLeuSerAlaSerVal

GlyAspArgValThrIleThrCysSerAlaSerSerSerValSerTyr

MetAsnTrpTyrGlnGlnThrProGlyLysAlaProLysArgTrpIle

TyrAspThrSerLysLeuAlaSerGlyValProSerArgPheSerGly

SerGlySerGlyThrAspTyrThrPheThrIleSerSerLeuGlnPro

GluAspIleAlaThrTyrTyrCysGlnGlnTrpSerSerAsnProPhe

ThrPheGlyGlnGlyThrLysLeuGlnIleThr

In the Fab, the heavy chain may include the $C_{H1}$ domain and a hinge region of human $IgG_1$. One example of this sequence is:

(SEQ ID NO: 16)
AlaSerThrLysGlyProSerValPheProLeuAlaProSerSerLys

SerThrSerGlyGlyThrAlaAlaLeuGlyCysLeuValLysAspTyr

PheProGluProValThrValSerTrpAsnSerGlyAlaLeuThrSer

GlyValHisThrPheProAlaValLeuGlnSerSerGlyLeuTyrSer

LeuSerValValThrValProSerSerSerLeuGlyThrGlnThr

TyrIleCysAsnValAsnHisLysProSerAsnThrLysValAspLys

LysValGluProLysSerCysAspLysThrHisThrCysProProCys

Pro

In the Fab, the kappa light chain constant domain of IgG$_1$ may be added C-terminal to the light chain variable region. One example of the kappa light chain constant domain is:

(SEQ ID NO: 17)
ArgThrValAlaAlaProSerValPheIlePheProProSerAspGlu

GlnLeuLysSerGlyThrAlaSerValValCysLeuLeuAsnAsnPhe

TyrProArgGluAlaLysValGlnTrpLysValAspAsnAlaLeuGln

SerGlyAsnSerGlnGluSerValThrGluGlnAspSerLysAspSer

ThrTyrSerLeuSerSerThrLeuThrLeuSerLysAlaAspTyrGlu

LysHisLysValTyrAlaCysGluValThrHisGlnGlyLeuSerSer

ProValThrLysSerPheAsnArgGlyGluCys

In one embodiment, the multivalent antibody fragment includes an scFv. The sequence of one such scFv is against EGFR (763scFv), shown below:

(SEQ ID NO: 9)
AspIleGlnMetThrGlnSerProSerSerLeuSerAlaSerValGly

AspArgValThrIleThrCysGlnAlaSerGlnAspIleSerAsnTyr

LeuAsnTrpTyrGlnGlnLysProGlyLysAlaProLysLeuLeuIle

TyrAspAlaSerAsnLeuGluThrGlyValProSerArgPheSerGly

SerGlySerGlyThrAspPheThrPheThrIleSerSerLeuGlnPro

GluAspIleAlaThrTyrPheCysGlnHisPheAspHisLeuProLeu

AlaPheGlyGlyGlyThrLysValGluIleLysGlyGlyGlyGlySer

GlyGlyGlyGlySerGlyGlyGlyGlySerGlnValGlnLeuGlnGlu

SerGlyProGlyLeuValLysProSerGluThrLeuSerLeuThrCys

ThrValSerGlyGlySerValSerSerGlyAspTyrTyrTrpThrTrp

IleArgGlnSerProGlyLysGlyLeuGluTrpIleGlyHisIleTyr

TyrSerGlyAsnThrAsnTyrAsnProSerLeuLysSerArgLeuThr

IleSerIleAspThrSerLysThrGlnPheSerLeuLysLeuSerSer

ValThrAlaAlaAspThrAlaIleTyrTyrCysValArgAspArgVal

ThrGlyAlaPheAspIleTrpGlyGlnGlyThrMetValThrValSer

Ser

B. Hinge Region

The fusion proteins of the present invention may include a "hinge region." In one embodiment, the hinge region is an approximately 4-15 amino acid long sequence. It may be the hinge region of a human IgG or a glycine linker. In one embodiment, the hinge region of a human IgG is the hinge region of human IgG$_1$ or human IgG$_2$.

In one embodiment, the "hinge region" has one of the following sequences:
GluProLysSerGlyAspLysThrHisThrCysProProCysPro (SEQ ID NO: 18) or
GluProLysSerCysAspLysThrHisThrCysProProCysPro (SEQ ID NO: 19) or one of the following:

| Amino acid sequences of the hinge region of human immunoglobulins | | |
|---|---|---|
| SEQ ID NO: 20 | Human IgG$_1$ | EPKSCDKTHTCPPCPAPELLGGP |
| SEQ ID NO: 21 | Human IgG$_2$ | ERKCCVECPPCPAPPVAGP |
| SEQ ID NO: 22 | Human IgG$_3$ | ELKTPLGDTTHTCPRCPAPELLGGP |
| SEQ ID NO: 23 | Human IgG$_4$ | ESKYGPPCPSCPAPEFLGGP |

In one embodiment, the "hinge region" comprises a glycine linker.

Examples of a Glycine Linker (G-linker) may include the following:
(GGGGS)$_3$ (SEQ ID NO: 24) The most commonly used linker of scFv contains a fifteen amino acid combination of glycine and serine residues.
GGSGGSGGGGSGGGGS (SEQ ID NO: 25), as shown in U.S. Pat. No. 5,908,626: Hybrid with interferon-β and an immunoglobulin Fc joined by a peptide linker.
RGRGRGRGRGRGGGS (SEQ ID NO: 26) taken from scFv-RG3.

Linkers may also be used elsewhere in the present multivalent antibody fragments.

C. The Collagen-Like Peptide

Descriptions of collagen-like peptides can be found in the description of the collagen-like domains of U.S. patent application Ser. No. 13/588,752, which is hereby expressly incorporated by reference in its entirety. Collagen-like peptides of the invention may include a GPP or GPO motif and/or a trimerizing motif or other structure. For example, one such collagen-like peptide may have a sequence as follows:

(SEQ ID NO: 27)
GlyProProGlyProProGlyProProGlyProProGlyProProGly

ProProGlyProProGlyProProGlyProProGlyProPro.

D. Linker

The linker is a short peptide sequence which optionally may be placed in between the antibody fragment and the collagen-like peptide region or between the binding domain and the collagen-like peptide region. The scFv polypeptide also comprises a polypeptide linker between the V$_H$ and V$_L$ domains which enables the scFv to form the desired structure for antigen binding. In some embodiments, the linker in either instance is between 4 and 10 amino acids in length, and may have the sequence:
Alaalaalaglyglyglyglyser (SEQ ID NO: 28) or glyglyglyglyser (SEQ ID NO: 29).

Glycine Linker (G-linker): (GGGGS)$_3$ (SEQ ID NO: 24), the most commonly used linker of scFv contains a fifteen combination of glycine and serine residues.
GGSGGSGGGGSGGGGS (SEQ ID NO: 25) found in U.S. Pat. No. 5,908,626 entitled Hybrid with interferon-β and an immunoglobulin Fc joined by a peptide linker, which is hereby expressly incorporated by reference.

```
                                          (SEQ ID NO: 30)
    Glycine-alanine linker: GGAGAGAG (SEQ ID NO: 26)
    Glycine-arginine linker: RGRGRGRGRGRGGGS.
```

Specific embodiments include Formats A-C, shown in FIG. 1 as trimers. Format A: FabCSA, is a trimeric antibody fragment having a Fab fragment at the N-terminus of a collagen-like peptide capable of self-trimerization; Format B: FabCSA-scFv, is a trimeric bispecific antibody fragment having a Fab fragment and a single-chain antibody fragment at the N- and C-terminus of a collagen-like peptide capable of self-trimerization, respectively; and Format C: FabCSA-sdAb, is a trimeric bispecific antibody fragment having a Fab fragment and a single-domain antibody at the N- and C-terminus of a collagen-like peptide capable of self-trimerization, respectively. Notably, Formats A-C include three monomers, each monomer having, in the Fab region, a heavy and light chain.

The specific examples below are to be construed as merely illustrative, and not limiting of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Example 1

Construction of h145FabCSA, hOKT3FabCSA and hOKT3FabCSA763scFv

Listed below are the polypeptide sequence of the heavy chain of h145FabCSA (SEQ ID NO: 1) and the cDNA sequence encoding it (SEQ ID NO: 2). The coding region of the heavy chain of h145FabCSA, from N- to C-terminus, included a signal peptide (underline)(SEQ ID NO: 11), the heavy chain variable region derived from the hamster anti-mouse CD3 antibody (145-2C11) (boldface)(SEQ ID NO: 12), the $C_{H1}$ domain and the hinge region of human IgG$_1$ (italics)(SEQ ID NO: 16), followed by a (GPP)$_{10}$ collagen-like domain (double-underline)(SEQ ID NO: 31). This synthetic sequence (SEQ ID NO: 2) was prepared by overlapping PCR.

```
                                                                    SEQ ID NO: 1
MetGluThrAspThrLeuLeuLeuTrpValLeuLeuLeuTrpValProGlySerThrGlyAspGluValGlnLeu

GlnGluSerGlyGlyGlyLeuValGlnProGlyLysSerLeuLysLeuSerCysGluAlaSerGlyPheThrPhe

SerGlyTyrGlyMetHisTrpValArgGlnAlaProGlyArgGlyLeuGluSerValAlaTyrIleThrSerSer

SerIleAsnIleLysTyrAlaAspAlaValLysGlyArgPheThrValSerArgAspAsnAlaLysAsnLeuLeu

PheLeuGlnMetAsnIleLeuLysSerGluAspThrAlaMetTyrTyrCysAlaArgPheAspTrpAspLysAsn

TyrTrpGlyGlnGlyThrMetValThrValSerSerAlaSerThrLysGlyProSerValPheProLeuAlaPro

SerSerLysSerThrSerGlyGlyThrAlaAlaLeuGlyCysLeuValLysAspTyrPheProGluProValThr

ValSerTrpAsnSerGlyAlaLeuThrSerGlyValHisThrPheProAlaValLeuGlnSerSerGlyLeuTyr

SerLeuSerSerValValThrValProSerSerSerLeuGlyThrGlnThrTyrIleCysAsnValAsnHisLys

ProSerAsnThrLysValAspLysLysValAlaAlaAlaGluProLysSerGlyAspLysThrHisThrCysPro

ProCysProArgSerIlePro<u>GlyProProGlyProProGlyProProGlyProProGlyProProGlyProPro

GlyProProGlyProProGlyProPro</u>GlyIleCysAspProSerLeuCysThrGly

SEQ ID NO: 2
    ATGGAGACAGACACACTCCTGCTATGGGTACTGCTGCTCTGGGTTCCAGGTTCCACT

GGTGATGAAGTGCAGCTGCAGGAGTCTGGGGGAGGCTTGGTGCAGCCTGGAAAGTC

CCTGAAACTCTCCTGTGAGGCCTCTGGATTCACCTTCAGCGGCTATGGCATGCACTG

GGTCCGCCAGGCTCCAGGGAGGGGGCTGGAGTCGGTCGCATACATTACTAGTAGTA

GTATTAATATCAAATATGCTGACGCTGTGAAAGGCCGGTTCACCGTCTCCAGAGACA

ATGCCAAGAACTTACTGTTTCTACAAATGAACATTCTCAAGTCTGAGGACACAGCCA

TGTACTACTGTGCAAGATTCGACTGGGACAAAAATTACTGGGGCCAAGGAACCATG

GTCACCGTCTCCTCAGCTAGCACCAAGGGCCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCCA
```

-continued

```
GCAACACCAAGGTGGACAAGAAAGTTGCGGCCGCTGAGCCCAAATCTGGTGACAAA

ACTCACACATGCCCACCGTGCCCAAGATCTATTCCTGGGCCACCTGGTCCCCCAGGT

CCTCCAGGACCCCCAGGGCCCCCAGGCCCCCCCGGGCCGCCTGGACCCCCAGGGCC

ACCAGGCCCCCCAGGCATCTGCGACCCATCACTATGTACCGGTTAA
```

Listed below are the polypeptide sequence of the light chain of h145FabCSA (SEQ ID NO: 3) and the cDNA sequence encoding it (SEQ ID NO: 4). The coding region of the light chain of h145FabCSA, from N- to C-terminus, included a signal peptide (underline)(SEQ ID NO: 11), the light chain variable region derived from the hamster anti-mouse CD3 antibody (145-2C11) (boldface)(SEQ ID NO: 13), followed by the kappa light chain constant domain of human IgG$_1$ (italics)(SEQ ID NO: 17). This synthetic sequence (SEQ ID NO: 4) was prepared by overlapping PCR.

derived from pSecTag2/Hygro (Invitrogen) for antibody expression in mammalian cells. Listed below are the polypeptide sequence of the heavy chain of hOKT3FabCSA (SEQ ID NO: 5) and the cDNA sequence encoding it (SEQ ID NO: 6). The coding region of the heavy chain of hOKT3FabCSA, from N- to C-terminus, included a signal peptide (underline)(SEQ ID NO: 11), the heavy chain variable region of the humanized muromonab-CD3 (Orthoclone OKT3) (boldface)(SEQ ID NO: 14), the C$_{H1}$ domain and the hinge region of human IgG$_1$ (italics)(SEQ ID NO: 16), followed by a (GPP)$_{10}$ collagen-like domain (double-under-

SEQ ID NO: 3

<u>MetGluThrAspThrLeuLeuLeuTrpValLeuLeuLeuTrpValProGlySerThrGly</u>AspAspIleGlnMet

ThrGlnSerProSerSerLeuProAlaSerLeuGlyAspArgValThrIleAsnCysGlnAlaSerGlnAspIle

SerAsnTyrLeuAsnTrpTyrGlnGlnLysProGlyLysAlaProLysLeuLeuIleTyrTyrThrAsnLysLeu

AlaAspGlyValProSerArgPheSerGlySerGlySerGlyArgAspSerSerPheThrIleSerSerLeuGlu

SerGluAspIleGlySerTyrTyrCysGlnGlnTyrTyrAsnTyrProTrpThrPheGlyProGlyThrLysVal

GluIleLys*ArgThrValAlaAlaProSerValPheIlePheProProSerAspGluGlnLeuLysSerGlyThr*

*AlaSerValValCysLeuLeuAsnAsnPheTyrProArgGluAlaLysValGlnTrpLysValAspAsnAlaLeu*

*GlnSerGlyAsnSerGlnGluSerValThrGluGlnAspSerLysAspSerThrTyrSerLeuSerSerThrLeu*

*ThrLeuSerLysAlaAspTyrGluLysHisLysValTyrAlaCysGluValThrHisGlnGlyLeuSerSerPro*

*ValThrLysSerPheAsnArgGlyGluCys*

SEQ ID NO: 4

```
ATGGAGACAGACACACTCCTGCTATGGGTACTGCTGCTCTGGGTTCCAGGTTCCACT

GGTGATGACATCCAGATGACCCAGTCTCCATCATCACTGCCTGCCTCCCTGGGAGAC

AGAGTCACTATCAATTGTCAGGCCAGTCAGGACATTAGCAATTATTTAAACTGGTAC

CAGCAGAAACCAGGGAAAGCTCCTAAGCTCCTGATCTATTATACAAATAAATTGGC

AGATGGAGTCCCATCAAGGTTCAGTGGCAGTGGTTCTGGGAGAGATTCTTCTTTCAC

TATCAGCAGCCTGGAATCCGAAGATATTGGATCTTATTACTGTCAACAGTATTATAA

CTATCCGTGGACGTTCGGACCTGGCACCAAGGTGGAGATCAAGCGTACGGTGGCTG

CACCATCTGTCTTCATCTTCCCGCCATCTGATGAGCAGTTGAAATCTGGAACTGCCTC

TGTTGTGTGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGGACAGCA

AGGACAGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCCGTCAC

AAAGAGCTTCAACAGGGGAGAGTGTTAG
```

The heavy and the light chain inserts of h145FabCSA were subsequently cloned into a dual expression vector line)(SEQ ID NO: 31). This synthetic sequence (SEQ ID NO: 6) was prepared by overlapping PCR.

SEQ ID NO: 5

<u>MetGluThrAspThrLeuLeuLeuTrpValLeuLeuLeuTrpValProGlySerThrGly</u>AspGlnValGlnLeu

ValGlnSerGlyGlyGlyValValGlnProGlyArgSerLeuArgLeuSerCysLysAlaSerGlyTyrThrPhe

ThrArgTyrThrMetHisTrpValArgGlnAlaProGlyLysGlyLeuGluTrpIleGlyTyrIleAsnProSer

ArgGlyTyrThrAsnTyrAsnGlnLysValLysAspArgPheThrIleSerArgAspAsnSerLysAsnThrAla

PheLeuGlnMetAspSerLeuArgProGluAspThrGlyValTyrPheCysAlaArgTyrTyrAspAspHisTyr

CysLeuAspTyrTrpGlyGlnGlyThrProValThrValSerSer_AlaSerThrLysGlyProSerValPhePro_

_LeuAlaProSerSerLysSerThrSerGlyGlyThrAlaAlaLeuGlyCysLeuValLysAspTyrPheProGlu_

_ProValThrValSerTrpAsnSerGlyAlaLeuThrSerGlyValHisThrPheProAlaValLeuGlnSerSer_

_GlyLeuTyrSerLeuSerSerValValThrValProSerSerSerLeuGlyThrGlnThrTyrIleCysAsnVal_

_AsnHisLysProSerAsnThrLysValAspLysLysValGluProLysSerCysAspLysThrHisThrCysPro_

_ProCysProAlaProGluLeuLeuGly_<u>GlyProProGlyProProGlyProProGlyProProGlyProProGly</u>

<u>ProProGlyProProGlyProProGlyProProGlyProPro</u>GlyIleCysAspProSerLeuCysThrGly

SEQ ID NO: 6

```
ATGGAGACAGACACACTCCTGCTATGGGTACTGCTGCTCTGGGTTCCAGGTTCCACT
GGTGATCAGGTGCAGCTGGTGCAGAGCGGCGGCGGCGTGGTGCAGCCTGGCAGGAG
CCTGAGGCTGAGCTGCAAGGCCAGCGGCTACACCTTCACCAGGTACACCATGCACT
GGGTGAGGCAGGCCCCTGGCAAGGGCCTGGAGTGGATCGGCTACATCAACCCTAGC
AGGGGCTACACCAACTACAACCAGAAGGTGAAGGACAGGTTCACCATCAGCAGGG
ACAACAGCAAGAATACCGCCTTCCTGCAGATGGACAGCCTGAGGCCTGAGGACACC
GGCGTGTACTTCTGCGCCAGGTACTACGACGACCACTACTGCCTGGACTACTGGGGC
CAGGGCACCCCTGTGACCGTGAGCAGCGCTAGCACCAAGGGTCCATCGGTCTTCCCC
CTGGCACCCTCCTCCAAGAGCACCTCTGGGGGCACAGCGGCCCTGGGCTGCCTGGTC
AAGGACTACTTCCCCGAACCTGTGACGGTGTCGTGGAACTCAGGCGCCCTGACCAG
CGGCGTGCACACCTTCCCGGCTGTCCTACAGTCCTCAGGACTCTACTCCCTCAGCAG
CGTGGTGACCGTGCCCTCCAGCAGCTTGGGCACCCAGACCTACATCTGCAACGTGAA
TCACAAGCCCAGCAACACCAAGGTGGACAAGAAAGTTGAGCCCAAATCTTGTGACA
AAACTCACACATGCCCACCGTGCCCAGCACCTGAACTCCTGGGAGGGCCACCTGGT
CCCCCAGGTCCTCCAGGACCCCCAGGGCCCCAGGCCCCCCGGGCCGCCTGGACC
CCCAGGGCCACCAGGCCCCCCAGGCATCTGCGACCCATCACTATGTACCGGTTAA
```

Listed below are the polypeptide sequence of the light chain of hOKT3FabCSA (SEQ ID NO: 7) and the cDNA sequence encoding it (SEQ ID NO: 8). The coding region of the light chain of hOKT3FabCSA, from N- to C-terminus, included a signal peptide (underline)(SEQ ID NO: 11), the light chain variable region of the humanized muromonab-CD3 (Orthoclone OKT3) (boldface)(SEQ ID NO: 15), followed by the kappa light chain constant domain of human IgG$_1$ (italics)(SEQ ID NO: 17). This synthetic sequence (SEQ ID NO: 8) was prepared by overlapping PCR.

SEQ ID NO: 7

<u>MetGluThrAspThrLeuLeuLeuTrpValLeuLeuLeuTrpValProGlySerThrGly</u>AspAspIleGlnMet

ThrGlnSerProSerSerLeuSerAlaSerValGlyAspArgValThrIleThrCysSerAlaSerSerSerVal

SerTyrMetAsnTrpTyrGlnGlnThrProGlyLysAlaProLysArgTrpIleTyrAspThrSerLysLeuAla

SerGlyValProSerArgPheSerGlySerGlySerGlyThrAspTyrThrPheThrIleSerSerLeuGlnPro

GluAspIleAlaThrTyrTyrCysGlnGlnTrpSerSerAsnProPheThrPheGlyGlnGlyThrLysLeuGln

IleThr_ArgThrValAlaAlaProSerValPheIlePheProProSerAspGluGlnLeuLysSerGlyThrAla_

-continued

SerValValCysLeuLeuAsnAsnPheTyrProArgGluAlaLysValGlnTrpLysValAspAsnAlaLeuGln

SerGlyAsnSerGlnGluSerValThrGluGlnAspSerLysAspSerThrTyrSerLeuSerSerThrLeuThr

LeuSerLysAlaAspTyrGluLysHisLysValTyrAlaCysGluValThrHisGlnGlyLeuSerSerProVal

ThrLysSerPheAsnArgGlyGluCys

SEQ ID NO: 8

ATGGAGACAGACACACTCCTGCTATGGGTACTGCTGCTCTGGGTTCCAGGTTCCACT

GGTGATGACATCCAGATGACCCAGAGCCCTAGCAGCCTGAGCGCCAGCGTGGGCGA

CAGGGTGACCATCACCTGCAGCGCCAGCAGCAGCGTGAGCTACATGAACTGGTACC

AGCAGACCCCTGGCAAGGCCCCTAAGAGGTGGATCTACGACACCAGCAAGCTGGCC

AGCGGCGTGCCTAGCAGGTTCAGCGGCAGCGGCAGCGGCACCGACTACACCTTCAC

CATCAGCAGCCTGCAGCCTGAGGACATCGCCACCTACTACTGCCAGCAGTGGAGCA

GCAACCCTTTCACCTTCGGCCAGGGCACCAAGCTGCAGATCACCCGTACGGTGGCTG

CACCATCTGTCTTCATCTTCCCGCCATCTGATGAGCAGTTGAAATCTGGAACTGCCTC

TGTTGTGTGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGGA

CAGCAAGGACAGCACCTACAGCCTCAGCAGCACCCTGACGCTGAGCAAAGCAGACT

ACGAGAAACACAAAGTCTACGCCTGCGAAGTCACCCATCAGGGCCTGAGCTCGCCC

GTCACAAAGAGCTTCAACAGGGGAGAGTGTTAG

The above heavy and the light chain inserts of hOKT3FabCSA were subsequently cloned into a dual expression vector derived from pSecTag2/Hygro (Invitrogen) for antibody expression in mammalian cells. Listed below are the polypeptide sequence of the 763 single-chain Fv, 763scFv of 763scFv (SEQ ID NO: 9) and the cDNA sequence encoding it (SEQ ID NO: 10). The cDNAs coding for the $V_L$ and $V_H$ of 763scFv were PCR amplified using primer sets derived from the corresponding cDNAs of the anti-EGFR monoclonal antibody, panitumumab (VECTIBIX®, Amgen, Inc.), based on the published nucleotide sequence (U.S. Pat. No. 6,235,883). The scFv PCR fusion of 763 was generated by joining the $V_L$ and $V_H$ chains with a glycine-linker (GGGGS)$_3$ (SEQ ID NO: 24) shown underlined in SEQ ID NO: 9.

An anti-CD3×EGFR bispecific antibody, hOKT3FabCSA763scFv, was generated as follows. The cDNA sequence encoding for 763scFv was cloned in-frame to the C-terminus of the heavy chain of hOKT3FabCSA at AgeI and BamHI sites to make a heavy chain construct consisting the heavy chain of hOKT3Fab, the hinge region of human IgG$_1$, a (GPP)$_{10}$ collagen-like domain (SEQ ID NO: 31), followed by 763scFv. The above heavy construct and the light chain construct of hOKT3FabCSA (SEQ ID NO: 8) were subsequently cloned into a dual expression vector derived from pSecTag2/Hygro (Invitrogen) for antibody expression in mammalian cells.

SEQ ID NO: 9

AspIleGlnMetThrGlnSerProSerSerLeuSerAlaSerValGlyAspArgValThrIleThrCysGlnAlaSer

GlnAspIleSerAsnTyrLeuAsnTrpTyrGlnGlnLysProGlyLysAlaProLysLeuLeuIleTyrAspAlaSer

AsnLeuGluThrGlyValProSerArgPheSerGlySerGlySerGlyThrAspPheThrPheThrIleSerSerLeu

GlnProGluAspIleAlaThrTyrPheCysGlnHisPheAspHisLeuProLeuAlaPheGlyGlyGlyThrLysVal

GluIleLys<u>GlyGlyGlyGlySerGlyGlyGlyGlySerGlyGlyGlyGlySer</u>GlnValGlnLeuGlnGluSerGly

ProGlyLeuValLysProSerGluThrLeuSerLeuThrCysThrValSerGlyGlySerValSerSerGlyAspTyr

TyrTrpThrTrpIleArgGlnSerProGlyLysGlyLeuGluTrpIleGlyHisIleTyrTyrSerGlyAsnThrAsn

TyrAsnProSerLeuLysSerArgLeuThrIleSerIleAspThrSerLysThrGlnPheSerLeuLysLeuSerSer

ValThrAlaAlaAspThrAlaIleTyrTyrCysValArgAspArgValThrGlyAlaPheAspIleTrpGlyGlnGly

ThrMetValThrValSerSer

-continued

SEQ ID NO: 10

```
GACATCCAGATGACCCAGAGCCCTAGCAGCCTGAGCGCCAGCGTGGGCGACAGGGT

GACCATCACCTGCCAGGCCAGCCAGGACATCAGCAACTACCTGAACTGGTACCAGC

AGAAGCCTGGCAAGGCCCCTAAGCTGCTGATCTACGACGCCAGCAACC

TGGAGACCGGCGTGCCTAGCAGGTTCAGCGGCAGCGGCAGCGGCACCGACTTCACC

TTCACCATCAGCAGCCTGCAGCCTGAGGACATCGCCACCTACTTCTGCCAGCACTTC

GACCACCTGCCTCTGGCCTTCGGCGGCGGCACCAAGGTGGAGATCAA

GGGTGGAGGCGGTTCAGGCGGAGGTGGCTCTGGCGGTGGCGGATCGCAGGTGCAGC

TGCAGGAGAGCGGCCCTGGCCTGGTGAAGCCTAGCGAGACCCTGAGCCTGACCTGC

ACCGTGAGCGGCGGCAGCGTGAGCAGCGGCGACTACTACTGGACCTGGATCAGGCA

GAGCCCTGGCAAGGGCCTGGAGTGGATCGGCCACATCTACTACAGCGGCAACACCA

ACTACAACCCTAGCCTGAAGAGCAGGCTGACCATCAGCATCGACACCAGCAAGACC

CAGTTCAGCCTGAAGCTGAGCAGCGTGACCGCCGCCGACACCGCCATCTACTACTGC

GTGAGGGACAGGGTGACCGGCGCCTTCGACATCTGGGGCCAGGGCACCATGGTGAC

CGTGAGCAGC
```

For the construction of the low-Fc binding anti-human CD3 antibody—hOKT3IgG-AA, with a structure feature similar to teplizumab (also called MGA031 and hOKT3-γ1 (Ala-Ala)), the variable regions of the heavy and light chain of hOKT3 were cloned into a human IgG$_1$ expression vector derived from pSecTag2/Hygro (Invitrogen), in which the wild type leucine residues at amino acids 234 and 235 of the heavy chain constant region was replaced with two alanine residues. For the construction of the low-Fc binding anti-mouse CD3 antibody—145IgG-AA, the variable regions of the heavy and light chain of the hamster anti-mouse CD3 antibody (145-2C11) were cloned into a mouse IgG$_{2a}$ expression vector (InvivoGen), in which the wild type leucine residues at amino acids 234 and 235 of the heavy chain constant region was replaced with two alanine residues. For the construction of anti-human EGFR antibody—763IgG, with a structure feature similar to panitumumab (Vectibix®), the variable regions of the heavy and light chain of panitumumab were cloned into a human IgG$_2$ expression vector derived from pSecTag2/Hygro (Invitrogen).

Example 2

Expression and Purification of h145FabCSA, 145IgG-AA, hOKT3FabCSA, hOKT3IgG-AA, 763IgG and hOKT3FabCSA763scFv The expression constructs of h145FabCSA, 145IgG-AA and hOKT3IgG-AA were used to transfect mouse myeloma NS0 cells (European Collection of Animal Cell Cultures, Wiltshire, UK) using Effectene (Qiagen) according to the manufacturer's instructions. After selection with Hygromycin B (400 µg/ml), stable clones were cultured in a shaker flask at an initial seeding density of $5 \times 10^5$ cells/ml in a chemically-defined medium HyQCDM4NS0 (Hyclone). The culture was maintained at 130 rpm for five days at 37° C. The expression constructs of hOKT3FabCSA, hOKT3FabCSA763scFv, and 763IgG were used to transfect CHO-S cells (Life Technologies Corporation), respectively, by electroporation using the Amax Nucleofector device (Amaxa, Inc., Gaithersburg, Md.) according to the manufacturer's instructions. After selection with Hygromycin B (400 µg/ml), stable clones were cultured in a shaker flask at an initial seeding density of $3 \times 10^5$ cells/ml in a chemically-defined medium CD OptiCHO™ (Life Technology). CD OptiCHO™ is an animal origin-free (AOF), chemically defined medium that contains no proteins, hydrolysates, or components of unknown composition and CD OptiCHO™ is formulated without phenol red. The culture was maintained at 130 rpm for 12 days at 37° C. The glucose was controlled at 2 mg/L by the addition of a 30 mg/ml glucose solution.

For the purification of h145FabCSA, hOKT3FabCSA and hOKT3FabCSA763scFv, around 1 L each of the filtered culture media were applied to a KappaSelect column (5-ml in bed volume, GE Healthcare) equilibrated with phosphate buffered saline (PBS), pH 7.4 (0.01 M phosphate buffer, 0.0027 M KCl, 0.14 M NaCl) at a flow rate of 60 ml/h. After washing with the same buffer, the recombinant antibodies were eluted with 50 mM of sodium phosphate buffer, pH 2.5. The UV absorbance was monitored at 280 nm and the peak fraction was collected, neutralized with 1.0 M of sodium bicarbonate to pH 7.5. The neutralized sample was then concentrated by ultrafiltration using Amicon Ultra-15 Centrifugal Filter Unit with Ultracel-30 membrane (EMD Millipore Corporation, Billerica, Mass.). Five milliliters of the concentrate were applied onto a HiLoad 16/600 SUPERDEX™ 200 column (a prepacked size exclusion chromatography column) (GE Healthcare) equilibrated with phosphate buffered saline (PBS), pH 7.4, at a linear flow rate of 1.5 ml/min.

For the purification of h145IgG-AA, hOKT3IgG-AA, and 763 IgG, around 1 L each of the filtered culture media were applied onto a HITRAP™ Protein A HP column (5-ml in bed volume, GE Healthcare) (a prepacked Protein A Sepharose High Performance column) equilibrated with phosphate buffered saline (PBS), pH 7.4 (0.01 M phosphate buffer, 0.0027 M KCl, 0.14 M NaCl) at a flow rate of 60 ml/h. After washing with the same buffer, the recombinant antibodies were eluted with 50 mM of sodium phosphate buffer, pH 2.5. The UV absorbance was monitored at 280 nm and the peak fraction was collected, neutralized with 1.0 M of sodium bicarbonate to pH 7.5. The neutralized samples were dialyzed against phosphate buffered saline (PBS), pH 7.4.

SDS-PAGE was carried out using either a 4-12% NUPAGE™ bis-Tris polyacrylamide gel (a SDS-PAGE gel electrophoresis system) with MES as running buffer (Invitrogen, San Diego, Calif.). Proteins were stained with INSTANTBLUE™ protein stain solution, a Coomassie based solution containing solubilisers, Coomassie Brilliant Blue, phosphoric acid and ethanol, manufactured by Expedeon Ltd, (Expedeon, Cambridgeshire, UK). Bench Mark (Invitrogen, San Diego, Calif.) was used as molecular size standards.

Results: Chromatography and Structural Characterization of h145FabCSA

Figure 2:
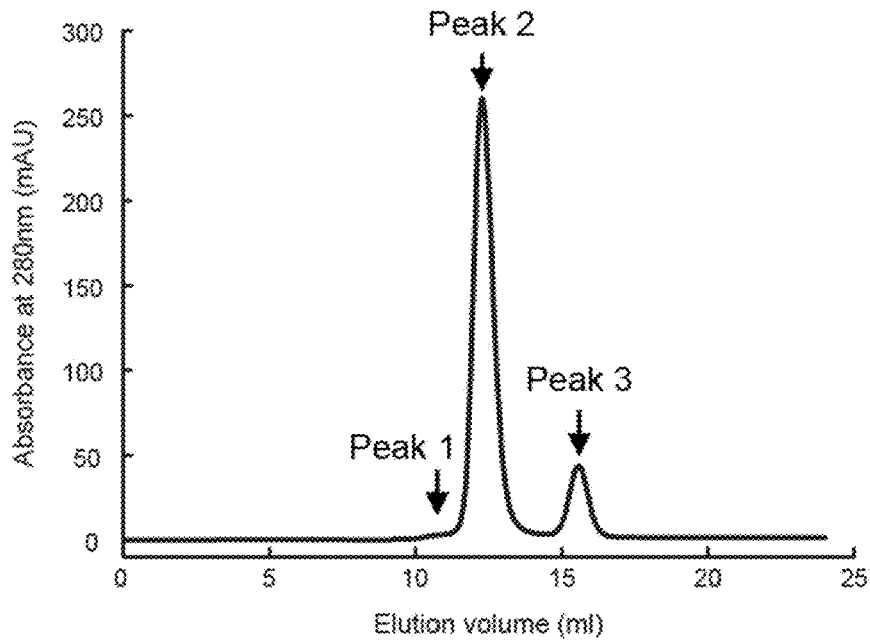
FIG. 2 depicts the structural characterization of the h145FabCSA molecules purified from culture media by sequential chromatographies on KappaSelect (an affinity medium designed for the purification of human Fab (kappa) fragments) and SUPERDEX™ 200 columns (a prepacked size exclusion chromatography column) according to the embodiments. (A) Separation of h145FabCSA species by gel filtration. Sample eluted from a KappaSelect column (an affinity medium designed for the purification of human Fab (kappa) fragments) was concentrated and loaded onto a SUPERDEX™ 200 columns (a prepacked size exclusion chromatography column) gel filtration column equilibrated with PBS (pH 7.4); (B) The different peak fractions (numbered Peaks 1 to 3 in A) and the sample loads were analyzed by SDS-PAGE under non-reducing (lanes 2, 4, 6, and 8) and reducing (lanes 3, 5, 7, and 9) conditions, where samples were treated with 50 mM of DTT for 10 min at 75° C. (C) Schematic representation of the structures corresponding to the protein bands indicated by arrowheads as shown in B. Dotted lines indicate putative disulfide bonds. All samples with equal amounts of protein were electrophoresed on a 4-12% SDS/Bis-Tris polyacrylamide gel with MES as a running buffer. The gels were stained with INSTANT-BLUE™ protein stain solution, a Coomassie based solution containing solubilisers, Coomassie Brilliant Blue, phosphoric acid and ethanol, manufactured by Expedeon Ltd.
Figure 2:
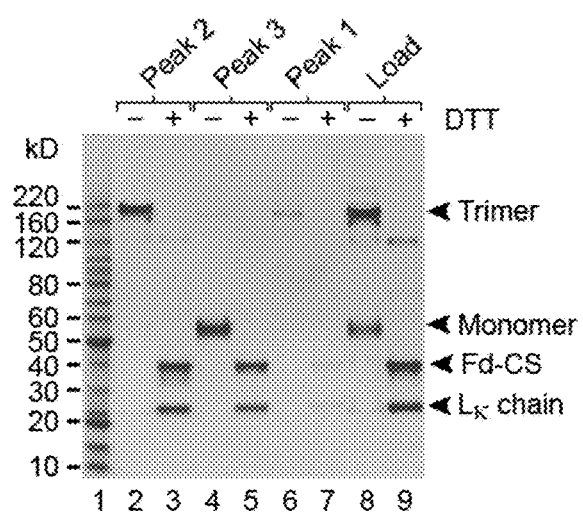
Figure 2:
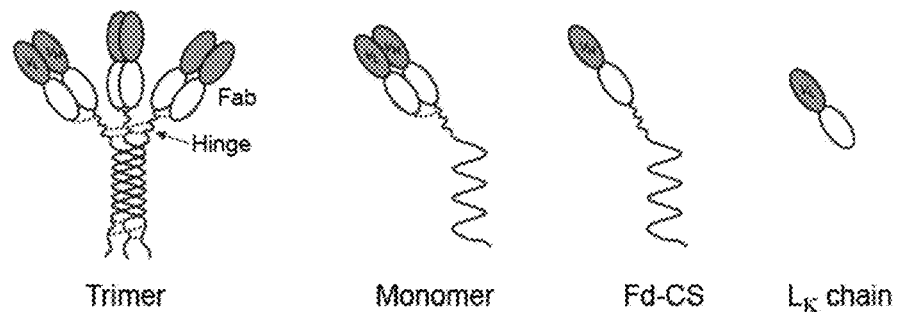

FIG. 2 depicts the structural characterization of the h145FabCSA molecules purified from culture media by sequential chromatographies on KappaSelect and SUPERDEX™ 200 columns (a prepacked size exclusion chromatography column) according to the embodiments. (A) Separation of h145FabCSA species by gel filtration. Sample eluted from KappaSelect column was concentrated and loaded onto a SUPERDEX™ 200 gel filtration column equilibrated with PBS (pH 7.4); (B) The different peak fractions (numbered Peaks 1 to 3 in A) and the sample load were analyzed by SDS-PAGE under non-reducing (lanes 2, 4, 6, and 8) and reducing (lanes 3, 5, 7, and 9) conditions, where samples were treated with 50 mM of DTT for 10 min at 75° C. (C) Schematic representation of the structures corresponding to the species resolved by SDS-PAGE shown in B.

The results demonstrated that the collagen-like peptide of the invention is capable of trimerizing an anti-mouse CD3 Fd fragment and an intact Fab fragment can be assembled in eukaryotic cells and secreted as a stable trimer.

Results: Chromatography and Structural Characterization of hOKT3FabCSA

Figure 3:
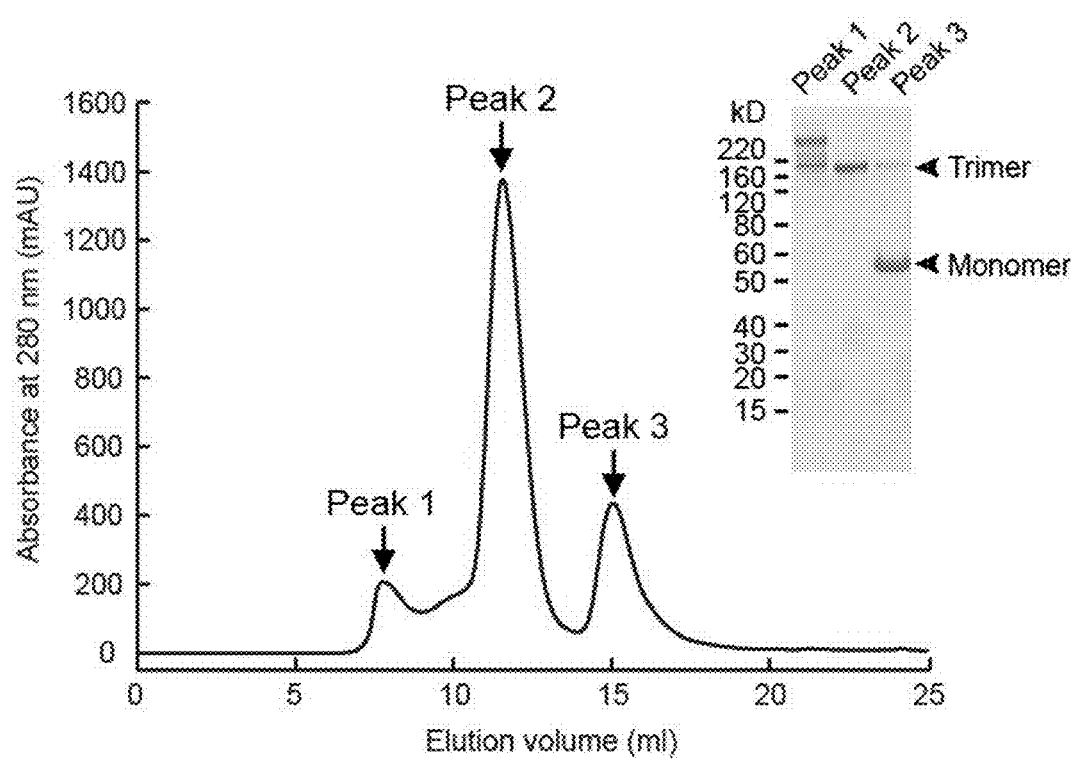
FIG. 3 depicts the structural characterization of the hOKT3FabCSA molecules purified from culture media by sequential chromatographies on KappaSelect (an affinity medium designed for the purification of human Fab (kappa) fragments) and SUPERDEX™ 200 columns (a prepacked size exclusion chromatography column) according to the embodiments. Sample eluted from a KappaSelect column (an affinity medium designed for the purification of human Fab (kappa) fragments) was concentrated and loaded onto a SUPERDEX™ 200 gel filtration column equilibrated with PBS (pH 7.4). Upper right panel: different peak fractions (numbered Peaks 1 to 3) separated by SUPERDEX™ 200 (a prepacked size exclusion chromatography column) were analyzed by SDS-PAGE under non-reducing conditions. Protein bands corresponding to hOKT3FabCSA trimer and monomer are indicated by arrowheads, respectively. All samples were electrophoresed on a 4-12% SDS/Bis-Tris polyacrylamide gel with MES as a running buffer. The gels were stained with INSTANTBLUE™ protein stain solution, a Coomassie based solution containing solubilisers, Coomassie Brilliant Blue, phosphoric acid and ethanol, manufactured by Expedeon Ltd.

FIG. 3 depicts the structural characterization of the hOKT3FabCSA molecules isolated by Superdex 200 chromatography according to the embodiments. Sample eluted from KappaSelect column was concentrated and loaded onto a SUPERDEX™ 200 gel filtration column (a prepacked size exclusion chromatography column) equilibrated with PBS (pH 7.4). Upper right panel: different peak fractions (numbered Peaks 1 to 3) were analyzed by SDS-PAGE under non-reducing conditions. Peak 2 is the main fraction which contains hOKT3FabCSA trimers, whereas Peak 3 fraction contains monomers. The major upper band shown in Peak 1 appears to be an interchain disulfide-bonded dimer of trimers. Again, the results demonstrated that the collagen-like peptide of the invention is capable of trimerizing an anti-human CD3 Fd fragment and an intact Fab fragment can be assembled in eukaryotic cells and secreted as a stable trimer.

Figure 4:
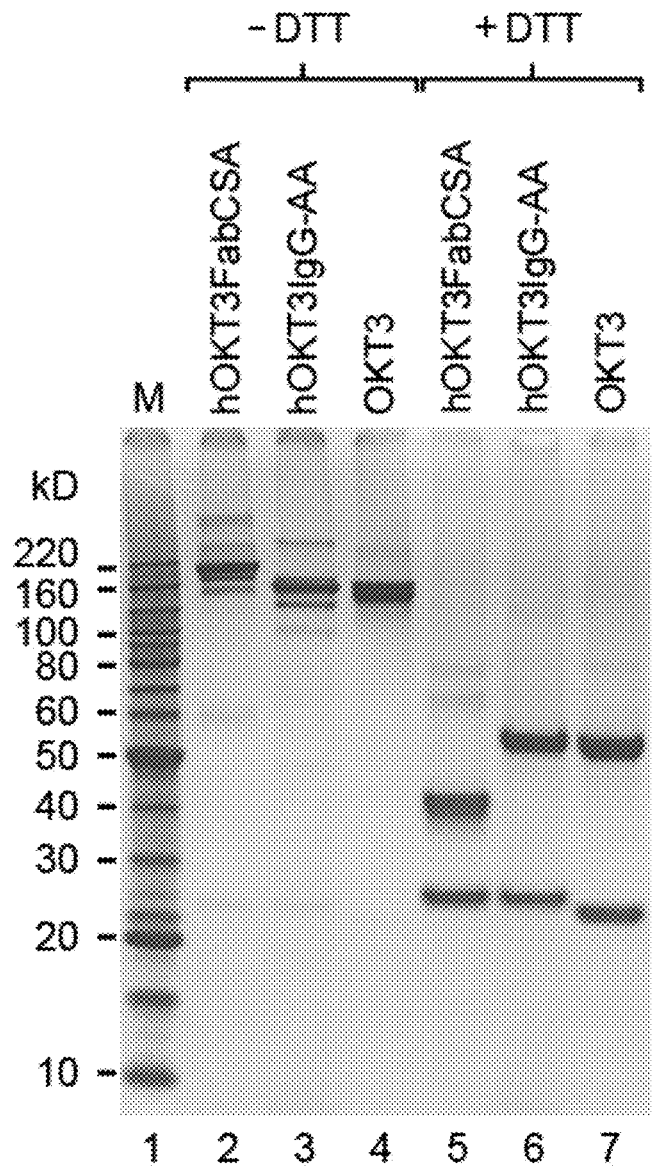
FIG. 4 depicts the purity analysis of the trimeric hOKT3FabCSA (peak 2 in FIG. 3), the low-Fc binding anti-human CD3 antibody hOKT3IgG-AA (purified by protein A column), and muromonab-CD3 (OKT3), separated by SDS-PAGE under non-reducing (lanes 2, 3, and 4) and reducing (lanes 5, 6, and 7) conditions, where samples were treated with 50 mM of DTT for 10 min at 75° C. All samples with equal amounts of protein were electrophoresed on a 4-12% SDS/Bis-Tris polyacrylamide gel with MES as a running buffer. The gels were stained with INSTANT-BLUE™ Protein Stain solution, a Coomassie based solution containing solubilisers, Coomassie Brilliant Blue, phosphoric acid and ethanol, manufactured by Expedeon Ltd. M, BENCHMARK™ molecular weight standard.

Results: Purity analysis of hOKT3FabCSA trimer, hOKT3IgG-AA, and OKT3 by SDS-PAGE FIG. 4 depicts the purity analysis of hOKT3FabCSA derived from the Peak 2 fraction in FIG. 3, the low-Fc binding anti-human CD3 antibody hOKT3IgG-AA and OKT3 antibody by SDSPAGE under non-reducing (lanes 2, 3, and 4) and reducing (lanes 5, 6, and 7) conditions, where samples were treated with 50 mM of DTT for 10 min at 75° C. All samples with equal amounts of protein were electrophoresed on a 4~12% SDS/Bis-Tris polyacrylamide gel with MES as a running buffer. The gels were stained with with 1NSTANTBLUE™ protein stain solution, a Coomassie based solution containing solubilisers, Coomassie Brilliant Blue, phosphoric acid and ethanol, manufactured by Expedeon Ltd. M, BENCHMARK™ molecular weight standard.

Under non-reducing conditions, the major band of hOKT3FabCSA is present as disulfide-linked Fab trimer (lane 2), whereas the non-disulfide linked Fd-CS and light chain were resolved under denaturing conditions (lane 5). hOKT3IgG-AA and OKT3 antibodies are in regular $IgG_1$ format, which contains two heavy and two light chains (lanes 3 and 4), under non-reducing conditions, and lanes 6 and 7, under reducing conditions).

Example 3

Determination of CD3 Binding Activities

Figure 5:
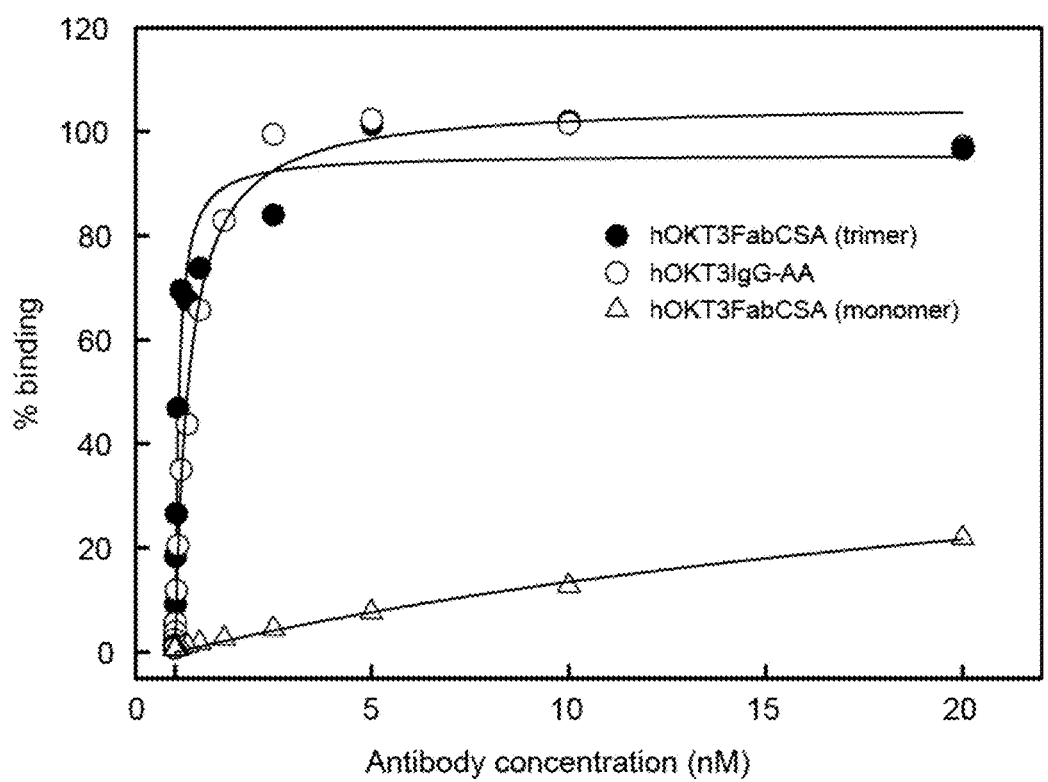
FIG. 5 depicts the binding affinities of the trimeric hOKT3FabCSA (isolated from peak 2 in FIG. 3), the low-Fc binding anti-human CD3 antibody—hOKT3IgG-AA (dimer), and the monomeric hOKT3FabCSA (isolated from peak 3 in FIG. 3) to the purified human T lymphocytes according to the embodiments.

Human T cells ($1\times10^6$/ml) were isolated from PBMC by a pan T cell isolation kit for negative selection (Miltenyi Biotec, CA) following manufacture's instruction. The cells were treated with Fc blocker (2 µg/ml, eBioscience, CA) for 30 min at 4° C. and were then incubated with a serial dilution of the purified low-Fc binding anti-human CD3 antibody—hOKT3IgG-AA, hOKT3FabCSA trimer and monomer for 30 min at 4° C. After washing, the cells were stained with goat anti-Human IgG (H+L)-Alexa Fluor 647 (Invitrogen) for 30 min at 4° C. and the binding of the antibody to T cells was detected by flow cytometry and presented as mean fluorescence intensity (MFI). As shown in FIG. 5, the trimeric hOKT3FabCSA (with a calculated $K_D$=0.02 nM) showed a 7.5-fold greater binding strength toward human T lymphocytes than the bivalent counterpart, hOKT3IgG-AA (with a calculated $K_D$=0.15 nM). The monovalent form of hOKT3FabCSA showed a weak, non-significant bind affinity towards the CD3+ human T cells.

Figure 6:
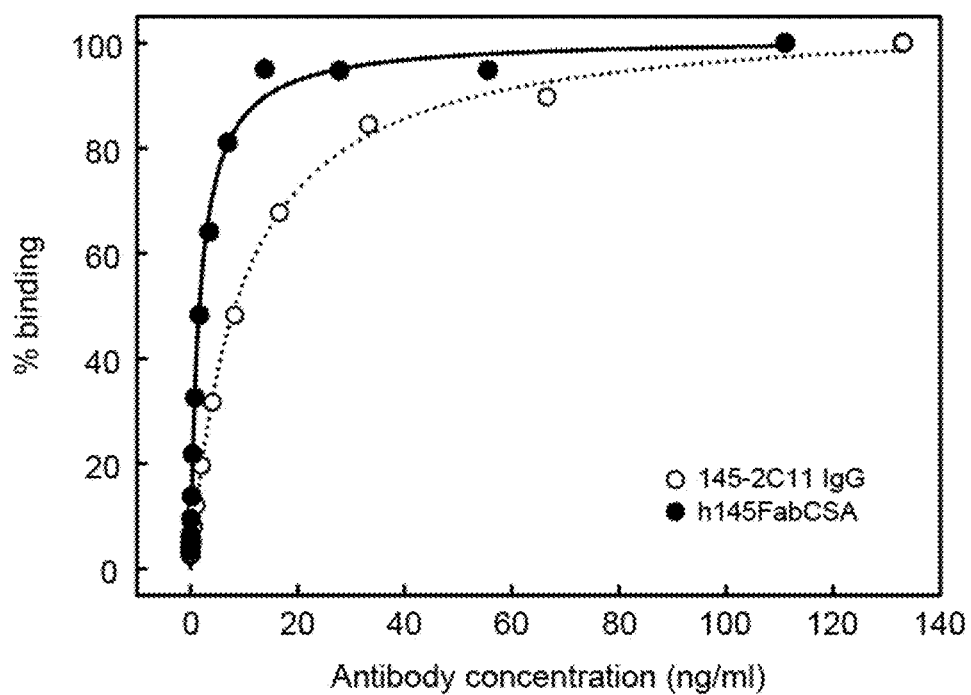
FIG. 6 depicts the binding affinities of the anti-mouse CD3 antibody—145-2C11 and the trimeric h145FabCSA (isolated from peak 2 in FIG. 2A) to the purified mouse spleen T lymphocytes according to the embodiments.

This experiment was also conducted to determine the binding affinities of the purified h145FabCSA trimer, in comparison with 145-2C11 hamster IgG, to mouse spleen T lymphocytes (FIG. 6). Again, the trimeric h145FabCSA (with a calculated $K_D$=4 nM) showed a 3.75-fold greater binding strength toward mouse T lymphocytes than the parental hamster IgG, 145-2C11 (with a calculated $K_D$=15 nM).

Example 4

Competitive Displacement Binding Assays

Because OKT3 and hOKT3FabCSA recognize the same epitope on CD3 ε chain, hOKT3FabCSA can competitively inhibit the binding of OKT3 to T cells. The avidities of the hOKT3FabCSA and OKT3 for binding to CD3 molecules on the cell surface of human T-cells were compared by flow cytometric analysis using antibody displacement assay with a saturated concentration of fluorescein-conjugated OKT3 as a competitor. All of the following procedures were conducted at 4° C. The CD3(+) Jurkat T cells, Clone E6-1 (ATCC number TIB-152), were suspended in 0.1 ml of staining buffer (phosphate-buffered saline with 2% fetal bovine serum and 0.1% sodium azide) at a total number of $1\times10^6$ cells. The cells were incubated with a serial dilution of hOKT3FabCSA or OKT3 IgG for 1 h. A fixed, saturating amount (0.25 µg/ml, determined by flow cytometry) of FITC-conjugated OKT3 (eBioscience, San Diego, Calif.) was added directly. After incubation for 1 h, the cells were washed with staining buffer and analyzed for immunofluorescence by flow cytometry on a FACSCALIBUR™ (Becton Dickinson, San Jose, Calif., USA) system. The data are presented as percent inhibition of maximal fluorescence intensity, which is defined as the mean fluorescence intensity obtained by staining T cells with OKT3-FITC in the absence of blocking mAbs. The concentration of each mAb required to inhibit half the maximal fluorescence intensity (IC50) was calculated.

Figure 7:
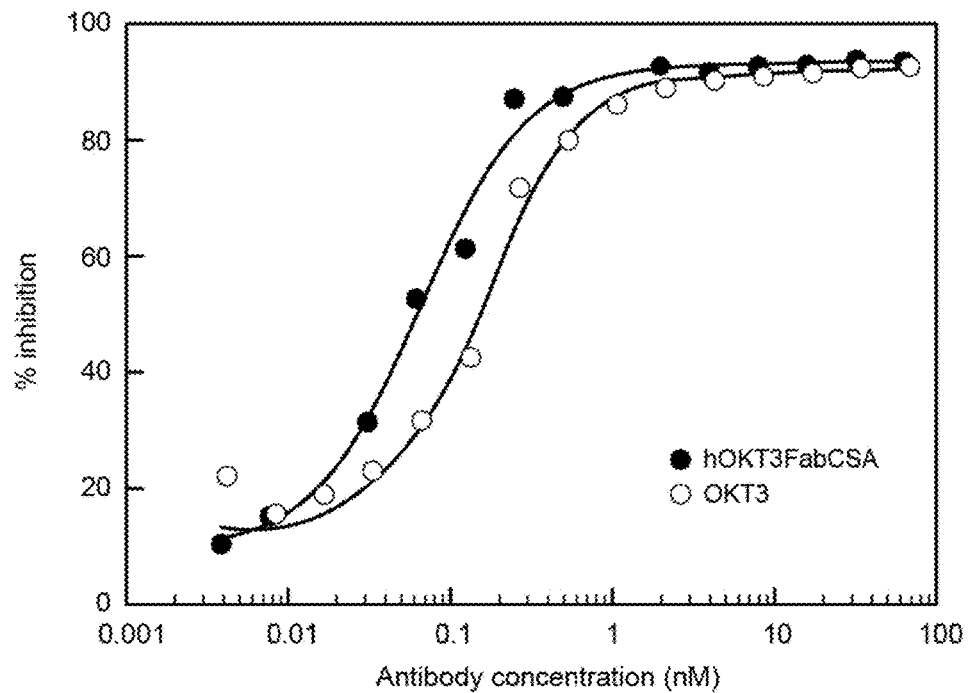
FIG. 7 depicts a two-independent-competitive displacement binding assays according to the embodiments. Jurkat cells expressing CD3(+) T-cell receptor were incubated with a serial dilution of anti-CD3 antibodies—the purified hOKT3FabCSA trimer (filled circles), and OKT3 (open circles), respectively, at 4° C. for 1 hour. A saturated amount of FITC-conjugated OKT3 was added and incubated for an additional hour. Cells were washed and the bound FITC-conjugated OKT3 was quantified by flow cytometry. Values are expressed as percentage inhibition of maximal fluorescence intensity, which is defined as the mean fluorescence intensity obtained by adding FITC-conjugated OKT3 without prior blocking of anti-CD3 antibodies.
Figure 7:
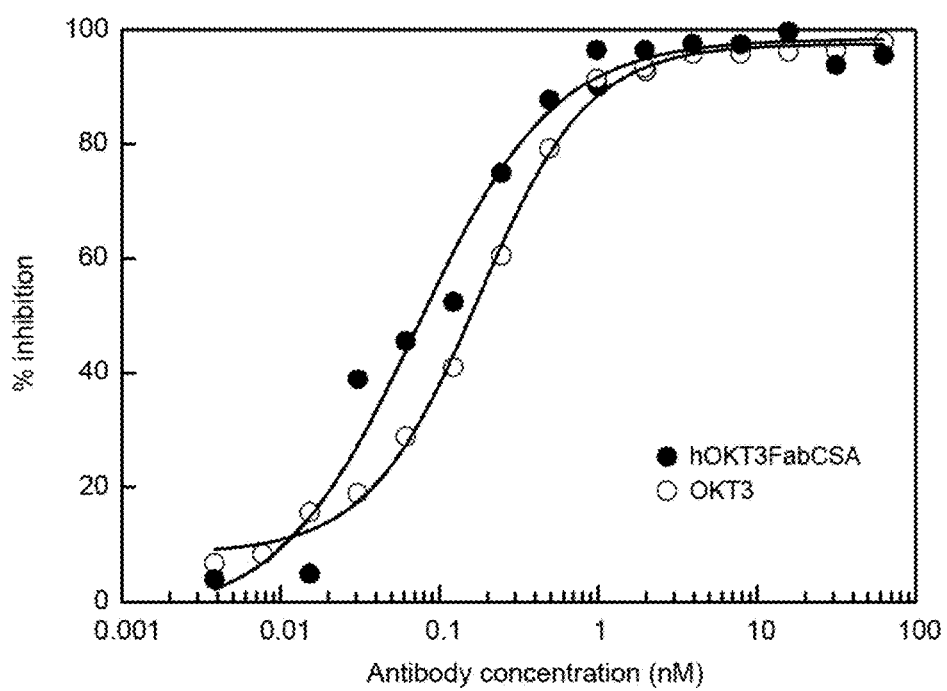

Comparison of the $IC_{50}$ values indicated that OKT3 required an approximately 2-fold higher concentration to achieve the same inhibition effect than that of hOKT3FabCSA using Jurkat T cells (FIG. 7, two independent experiments shown). The results indicated that, due to the avidity effect, the humanized trivalent hOKT3FabCSA exhibits a greater binding strength than its parental murine IgG form, OKT3.

Example 5

T Cell Proliferation

Studies comparing OKT3, hOKT3IgG-AA and hOKT3FabCSA in T cell activation were conducted by cell proliferation assay. Human peripheral blood mononuclear cells (PBMCs) collected from three healthy, normal donors were plated in a black 96-well flat bottom tissue culture plate at $2\times10^5$ cells/well in 100 μl RPMI-1640 medium with 10% FBS at 37° C. in the presence of 10-fold serial dilution of OKT3 (eBioscience, Inc.), hOKT3IgG-AA and hOKT3FabCSA for 66 h. The cells were then pulsed with 10 μM of BrdU for an additional 6 h. After removing the culture medium, the cells were fixed and DNA was denatured in one step with FixDenat (Roche Applied Science, Indianapolis Ind.). Afterward, the cells were incubated with a peroxidase labeled anti-BrdU antibody (anti-BrdU POD, Fab fragments) for 1.5 h at room temperature. Chemiluminescence detection and quantification was performed using a microplate-luminometer (Hidex, CHAMELEON detection platform, Finland). Each point shown in FIG. 8 represents mean±S.D. of three donors.

Figure 8:
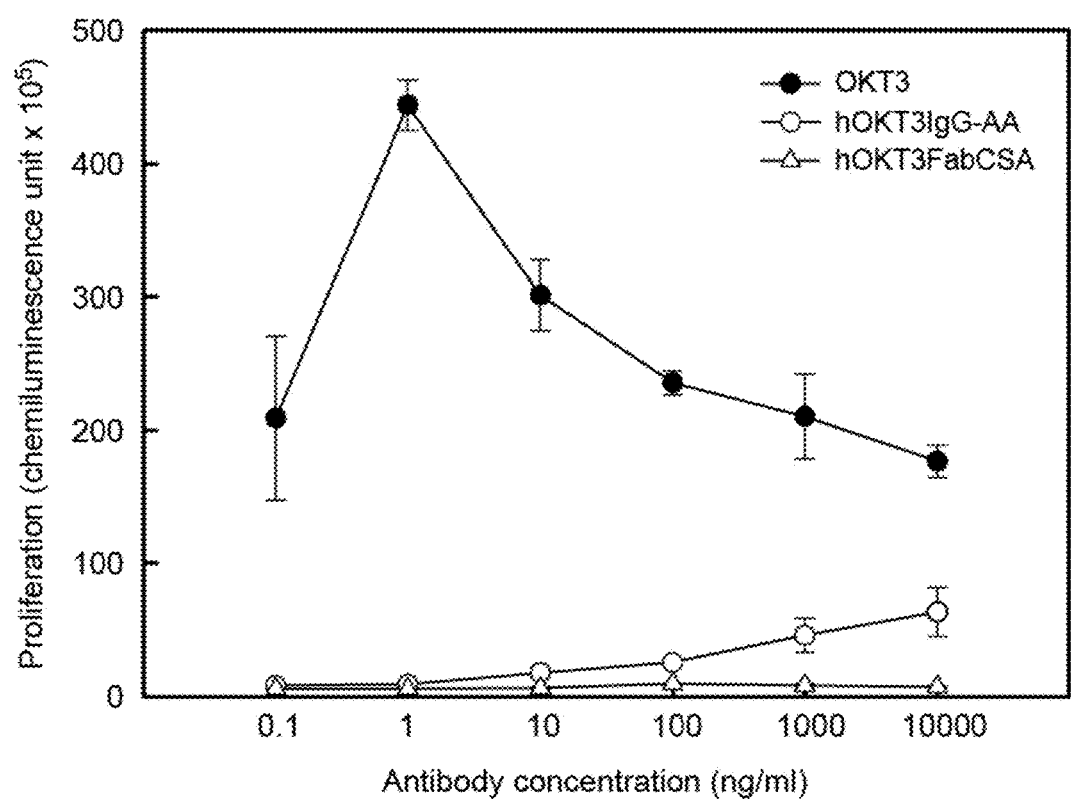
FIG. 8 depicts the T cell proliferation in response to the purified OKT3, the low-Fc binding anti-human CD3 antibody—hOKT3IgG-AA and hOKT3FabCSA trimer. Human PBMCs were collected from three healthy normal donors and incubated individually with serial log dilutions of OKT3 (filled circles), hOKT3IgG-AA (open circles) or hOKT3FabCSA (open triangles) for 66 h, pulsed with 10 μM of BrdU for an additional 6 hours. The cell proliferation was measured by BrdU-ELISA using chemiluminescent immunoassay to quantify the incorporation of BrdU during DNA synthesis. Each point represents mean±S.D. of three donors.

The results in FIG. 8 showed that OKT3, even at very low concentration, induced T cell proliferation significantly. The low-Fc binding hOKT3IgG-AA also induced T cell proliferation at higher antibody concentration, even though the induction was less potent. These results are consistent with earlier published work by Li, Li et al. (Li, J., J. Davis, et al. (2006). "Modulation of antigen-specific T cell response by a non-mitogenic anti-CD3 antibody." Int Immunopharmacol 6(6): 880-891.). In contrast, no detectable T cell proliferation was induced by hOKT3FabCSA. Therefore, the non-Fc version of hOKT3FabCSA trimer is the least inducer of T cell proliferation among different anti-CD3 antibody formats.

Example 6

Cytokine Measurement

Human PBMCs from three healthy normal donors were plated at $2\times10^5$ cells/well in 0.1 ml RPMI-1640 medium with 10% FBS at 37° C. in the presence of 10-fold serial dilution of OKT3, hOKT3IgG-AA and hOKT3FabCSA. The levels of IL-2 and the rest of the cytokines (IL-1β, IL-2, IL-6, IL-10, and IFN-γ) in the culture supernatants were determined using a human cytokine immunoassay kit (eBioscience, Inc.) at 24- and 72-hour time points, respectively.

The mitogenic activity of murine OKT3 is caused by extensive T cell receptor (TCR)-CD3 crosslinking via binding to FcR-positive cells. Therefore, efforts have recently been made to develop non-mitogenic forms of anti-CD3 by altering the binding to the Fc receptor. The capacities of OKT3, hOKT3IgG-AA and the trimeric hOKT3FabCSA to induce cytokines (IL-1β, IL-2, IL-6, IL-10, and IFN-γ) were measured. As expected, OKT3 IgG induced cytokine production dramatically at a very low dose. The low-Fc binding anti-human CD3 antibody—hOKT3IgG-AA, with a structure feature similar to teplizumab (also called MGA031 and hOKT3-γ1 (Ala-Ala)), also induced cytokine production at a higher antibody concentration, even though less potent. These results are consistent with earlier published work by Li (Li, Davis et al. 2006). In contrast, the trimeric hOKT3FabCSA does not induce detectable IL-2 and IFN-γ at a concentration up to 100 μg/ml. In comparison with hOKT3IgG-AA, hOKT3FabCSA had a lower induction level of IL-1β, IL-6, and IL-10 at a concentration above 10 μg/ml. The results showed that hOKT3FabCSA is the least mitogenic version among different anti-CD3 antibody formats (FIG. 9).

Example 7

Mixed Lymphocyte Reaction (MLR)

Immunosuppression in the one-way mixed lymphocyte reaction was assessed as follows. Human PBMCs were obtained from two healthy donors (stimulator and responder). Stimulator or responder cells were treated with 25 μg/ml of mitomycin C (Sigma-Aldrich) in a complete medium (RPMI 1640 supplemented with 10% human AB serum, 2 mM glutamine, 50 nM 2-mercaptoethanol, and 100 units/ml each of penicillin and streptomycin) for 30 minutes in humidified air containing 5% $CO_2$ at 37° C., followed by three washes in RPMI 1640 medium. Responder cells were cultured alone or mixed with mitomycin C treated stimulator or mitomycin C responder cells at 1:1 ratio at $2\times10^5$ cells/well in 200 μl of complete medium. Purified hOKT3FabCSA trimer, hOKT3IgG-AA, or OKT3 was added at different concentrations to cultures immediately after responder cell plating. After 5 days, cultured cells were pulsed with 10 μM of BrdU and harvested 24 h later. 5-bromo-2'-deoxyuridine (BrdU) cell proliferation assay was performed. After removing the culture medium, the cells were fixed and DNA was denatured in one step with FixDenat. Afterward, the cells were incubated with a peroxidase labeled anti-BrdU antibody (anti-BrdU POD, Fab fragments) for 1.5 h at room temperature. Chemiluminescence detection and quantification was performed using a microplate-luminometer (Hidex, CHAMELEON detection platform, Finland).

Figure 10:
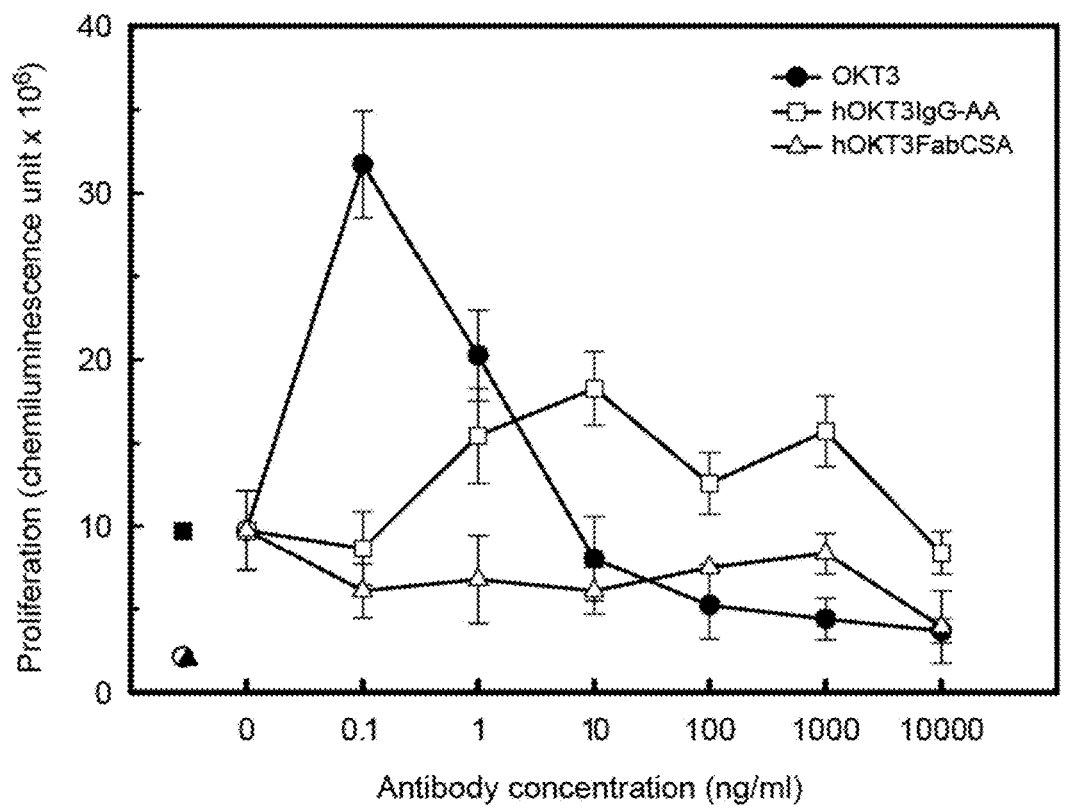
FIG. 10 depicts the inhibition of mixed lymphocyte reaction by the purified OKT3, hOKT3IgG-AA and hOKT3FabCSA trimer. Responder PBMCs mixed with mitomycin C-treated stimulator PBMCs were co-cultured for five days in the presence of different concentrations of OKT3 (filled circles), hOKT3IgG-AA (open squares) or hOKT3FabCSA (open triangles), pulsed with BrdU for an additional 16 hours. The cell proliferation was measured by BrdU-ELISA. The responder PBMCs mixed with mitomycin C-treated stimulator PBMCs and responder PBMCs in the absence of antibody were shown in a filled square and a filled triangle, respectively. The cell proliferation of the untreated stimulator PBMCs in the absence of antibody is shown in an open circle.

To determine whether the trimeric hOKT3FabCSA, upon increasing the binding avidity to CD3(+) T-cells, can exhibit immunosuppressive activity that is superior to that of the parental OKT3 antibody and the low-Fc binding anti-human CD3 antibody—hOKT3IgG-AA, antibodies were tested for T-cell mitogenic activation in a one-way mixed lymphocyte reaction (MLR). In mixed PBMC cultures (mitomycin C treated stimulator+responder) incubated for 5 days without antibody treatment, a mixed lymphocyte reaction (MLR) developed as a result of allogeneic stimulation of T cell activation (FIG. 10, filled square). Treating mixed PBMC cultures with OKT3 resulted in stimulation of T cell proliferation at low concentration level, ranging from 0.1 to 1.0 ng/ml (FIG. 10, solid circles). The immunosuppression of OKT3 is significant when antibody concentration is higher than 10 ng/ml. The low-Fc binding anti-human CD3 antibody—hOKT3IgG-AA did not show significant suppression of T cell activation (FIG. 10, open squares). In contrast, the potency of hOKT3FabCSA trimer in MLR was significant, reaching the background level at a concentration of 0.1 ng/ml (FIG. 10, open triangles). These results indicated that the trimeric hOKT3FabCSA is a potent immunosuppressant of T cell proliferation while exhibiting reduced mitogenicity in vitro.

Example 8

T Cell Receptor (TCR) Modulation

PBMCs from a healthy donor were plated at $2\times10^6$ cells/well in a 24-well plate (Nunc) and incubated in RPMI 1640 plus 10% FCS with varying amounts of hOKT3FabCSA (trimer), hOKT3IgG-AA (dimer), and hOKT3FabCSA (monomer). After 24 hours of incubation, cells were harvested and stained with FITC-conjugated OKT3 or anti-TCRα/β mAb IP26 (eBioscience). The stained cells were counterstained with phycoerythrin-conjugated anti-CD5 mAb UCHT2 (eBioscience) for T cells and analyzed by flow cytometry. Calculation of CD3 modulation and coating was performed as previously described (Cole, M. S., C. Anasetti, et al. (1997). "Human IgG$_2$ variants of chimeric anti-CD3 are non-mitogenic to T cells." J Immunol 159(7): 3613-3621.):

$$\% \ CD3 \ modulation = 100 \times \frac{\text{Control cells } F_{anti\text{-}TCR} - \text{Antibody-treated cells } F_{anti\text{-}TCR}}{\text{Control cells } F_{anti\text{-}TCR}}$$

$$\% \ CD3 \ coating = 100 \times \frac{\text{Antibody-treated cells } F_{anti\text{-}TCR}}{\text{Control cells } F_{anti\text{-}TCR}} - \frac{\text{Antibody-treated cells } F_{OKT3}}{\text{Control cells } F_{OKT3}}$$

where F represents mean fluorescence of stained cells.

Figure 11:
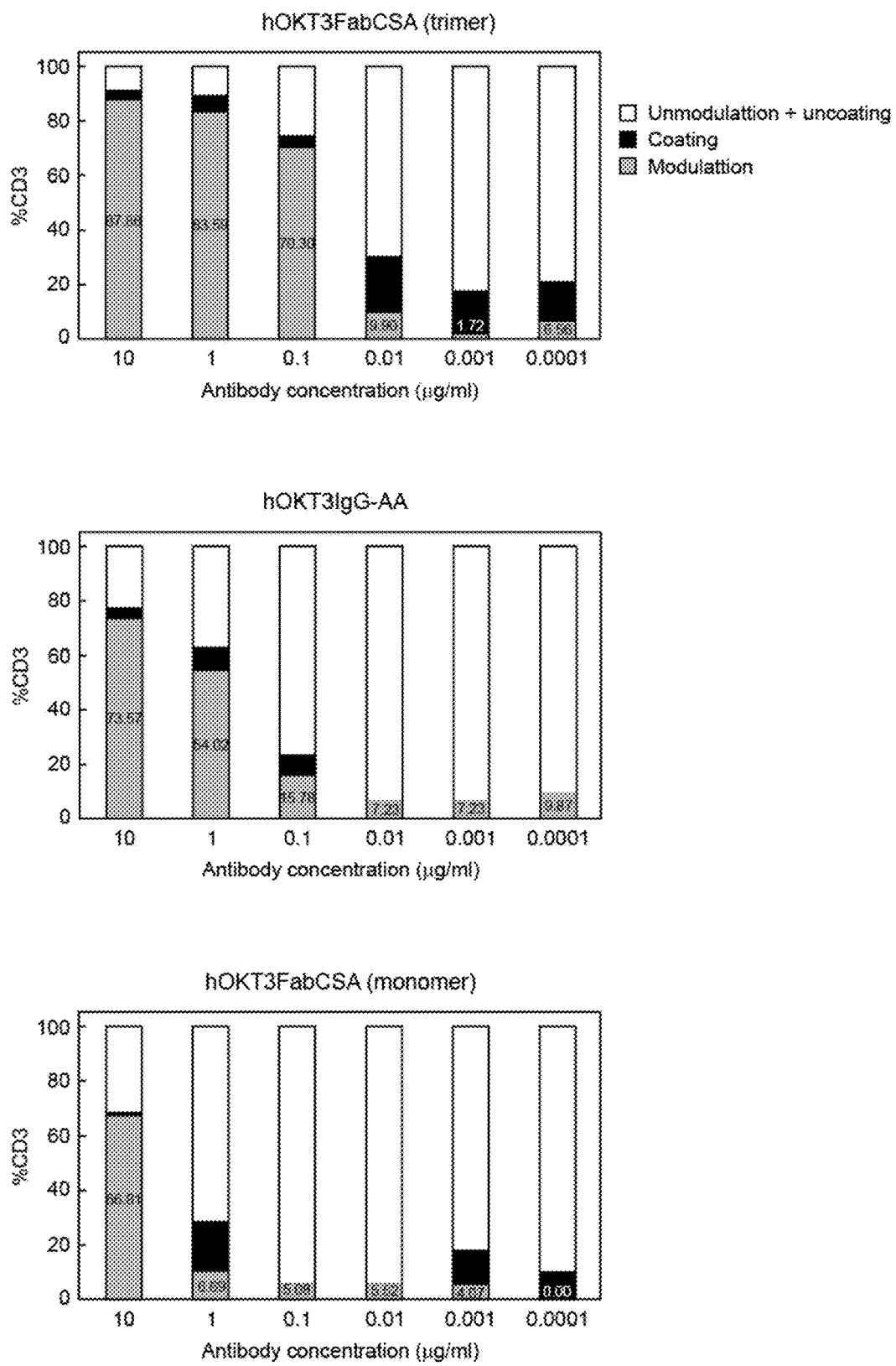
FIG. 11 depicts the quantitation of the T cell receptor (TCR)-CD3 modulation/coating by the purified hOKT3FabCSA (trimer), hOKT3IgG-AA (dimer) and hOKT3FabCSA (monomer). Data for CD3 modulation represent the percentage of TCR-CD3 complexes on the surface of treated CD5-positive T cells as a fraction of TCR-CD3 complexes on the surface of untreated CD5-positive T cells. CD3 coating is shown as the fraction of TCR-CD3 complexes that could not be detected by FITC-conjugated OKT3.

In FIG. 11, the combined modulation and coating of the TCR-CD3 complex achieved by trivalent hOKT3FabCSA is greater than that of the low-Fc binding anti-human CD3 antibody—hOKT3IgG-AA, at antibody concentrations ranging from 0.1 ng/ml to 10 μg/ml. Due to the low-crosslinking activity towards TCR, the monovalent hOKT3FabCSA exhibited a much lower TCR coating and modulation at each corresponding concentration. The results demonstrated that improvement in binding strength of the trimeric hOKT3FabCSA leads to an enhanced degree of TCR modulation.

Example 9

Pharmacokinetic Assays

Figure 12:
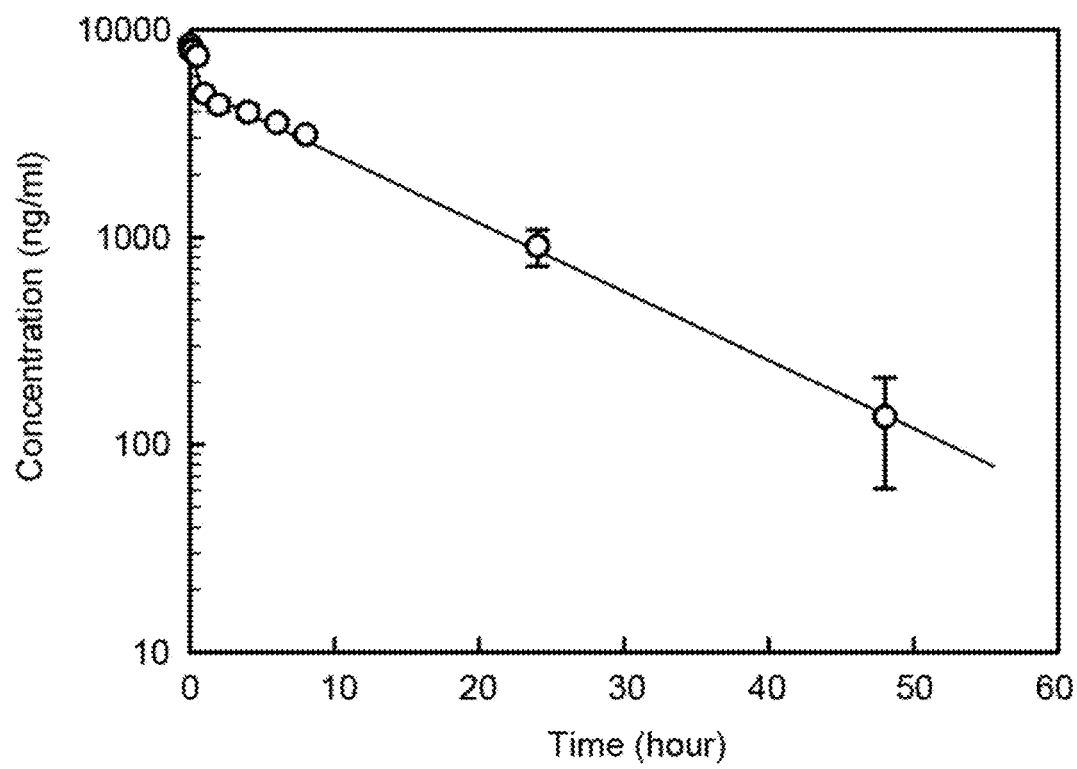
FIG. 12 depicts the blood clearance of the purified h145FabCSA trimer in mice according to the embodiments. Male BALB/c mice were injected intravenously with 25 µg of the h145FabCSA trimer. Blood samples were drawn at different times. The antibody level remaining in plasma was determined by anti-human Fd coated ELISA plates using horseradish peroxidase-conjugated anti-human kappa light chain as detecting antibody. Results are averaged from 3 animals for each time point.

To assess h145FabCSA blood clearance, 15 male BALB/c mice (randomized into five groups) were administered intravenously with the purified h145FabCSA trimer at a single dose level of 25 μg/mouse with a dose volume 0.1 ml/mouse. Blood (100 μl/mouse) was serially collected from mice and was transferred into an EDTA-coated tube at the following time points: 0, 2, 5, 15, 30 minutes, and 1, 2, 4, 6, 8, 24, 48, 72, and 96 hours. The remaining h145FabCSA in plasma samples from each time point were quantitated by interpolation into a standard curve of serial dilutions of h145FabCSA standard using ELISA. Anti-human Fd and horseradish peroxidase-conjugated anti-human kappa light chain were used as capture and detecting antibodies, respectively. 3,3',5,5',-tetramethylbenzidine was used as peroxidase substrate. The pharmacokinetic profile of h145FabCSA in mice is shown in FIG. 12.

Kinetics of the non-compartment model was determined. The plasma level of immunoreactivity decreased biphasically, with a terminal elimination phase half-life ($t_{1/2}$) of 8.85 hours.

Example 10

Biodistribution

The purified h145FabCSA trimer was radiolabeled with iodine-131 and the biodistribution of $^{131}$I-h145FabCSA was evaluated in 30 male BALB/c mice. Groups of five mice were administered intravenously with h145FabCSA (specific activity: 1.2 μCi/μg; 30 μCi/mouse). Time points for analysis of h145FabCSA were 0.5, 1, 2, 6, 24, and 48 hours. At the selected time points, euthanized and percent of injected dose per gram (% ID/g) tissue was determined. The $^{131}$I-h145FabCSA trimer exhibited a rapid blood clearance with the majority clearing by 48 hours (Table 1). However, the $^{131}$I-h145FabCSA showed a localization in the spleen, with 33.76±1.56% ID/g at 0.5 hour and reaching a maximum of 42.09±1.64% ID/g at 24 hours.

TABLE 1

Biodistribution of $^{131}$I-h145FabCSA trimer in BALB/c mice.

| Organ | 0.5 hr | 1 hr | 2 hr | 6 hr | 24 hr | 48 hr |
|---|---|---|---|---|---|---|
| Whole blood | 167.21 ± 10.04 | 151.21 ± 3.43 | 119.32 ± 1.95 | 68.12 ± 1.06 | 15.29 ± 0.54 | 2.77 ± 0.22 |
| Brain | 3.50 ± 0.29 | 3.67 ± 0.19 | 2.66 ± 0.10 | 1.72 ± 0.15 | 0.53 ± 0.06 | 0.12 ± 0.01 |
| Thymus | 9.22 ± 0.84 | 8.41 ± 0.80 | 6.94 ± 0.90 | 9.23 ± 0.57 | 4.69 ± 0.46 | 2.84 ± 0.40 |
| Muscle | 8.45 ± 1.08 | 7.24 ± 0.55 | 7.72 ± 1.35 | 5.70 ± 0.57 | 2.91 ± 0.44 | 1.39 ± 0.11 |
| Bone | 31.84 ± 3.27 | 29.79 ± 1.97 | 28.58 ± 1.83 | 26.33 ± 1.60 | 25.42 ± 2.88 | 8.82 ± 0.88 |
| Heart | 27.02 ± 1.90 | 23.62 ± 0.68 | 20.60 ± 0.39 | 16.13 ± 0.38 | 8.09 ± 0.46 | 4.90 ± 0.30 |
| Lung | 59.65 ± 5.71 | 55.33 ± 5.36 | 45.41 ± 3.66 | 28.73 ± 2.84 | 7.76 ± 0.34 | 4.13 ± 0.72 |
| Liver | 24.81 ± 2.58 | 21.64 ± 0.40 | 23.04 ± 1.23 | 22.67 ± 1.19 | 15.09 ± 1.00 | 9.12 ± 0.77 |
| Kidney | 38.16 ± 2.31 | 37.14 ± 1.13 | 32.41 ± 1.32 | 25.85 ± 0.70 | 10.61 ± 1.00 | 5.89 ± 0.35 |
| Large intestine | 7.78 ± 0.43 | 6.56 ± 1.03 | 10.48 ± 2.26 | 17.72 ± 6.60 | 5.44 ± 0.56 | 3.62 ± 0.34 |
| Small intestine | 23.42 ± 3.63 | 30.59 ± 2.71 | 51.28 ± 2.59 | 46.45 ± 3.93 | 18.99 ± 2.62 | 13.87 ± 1.52 |
| Spleen | 33.76 ± 1.56 | 38.82 ± 0.52 | 37.14 ± 0.91 | 42.09 ± 1.64 | 40.23 ± 1.44 | 37.87 ± 2.15 |
| Stomach | 8.25 ± 0.73 | 7.52 ± 0.39 | 9.12 ± 0.55 | 13.36 ± 0.98 | 6.63 ± 0.74 | 3.58 ± 0.32 |
| Testies | 5.74 ± 0.62 | 7.38 ± 0.36 | 8.32 ± 0.36 | 10.63 ± 0.30 | 6.80 ± 0.57 | 4.77 ± 0.21 |
| Bladder | 8.59 ± 1.25 | 10.42 ± 1.26 | 9.01 ± 0.66 | 11.17 ± 0.26 | 7.35 ± 0.55 | 4.14 ± 0.15 |

Note:
Organ uptakes are expressed as percent injected dose per gram (% ID/g).
SEMs are shown in parentheses.

Example 11

Experimental Autoimmune Encephalomyelitis Mouse Disease Model

Experimental autoimmune encephalomyelitis (EAE) is a widely used mouse model of multiple sclerosis. In this study, myelin oligodendrocyte glycoprotein (MOG)-induced murine EAE was used for studying the therapeutic effect of h145FabCSA on the modulation of paralysis. Female 6- to 8-week old C57BL/6 mice (National Laboratory Animal Center, Taiwan) were immunized subcutaneously with 200 µg MOG (35-55) in 200 µL of an emulsion in complete Freund's adjuvant containing 500 µg *Mycobacterium tuberculosis* H37RA. Immediately after immunization, mice received 500 ng intraperitoneally of pertussis toxin and again 48 hours later. Clinical EAE scores were evaluated using the following scale: 0=no symptoms, 0.5=distal weak or spastic tail, 1=completely limp tail, 1.5=limp tail and hindlimb weakness (feet slip through cage grill), 2.0=unilateral partial hindlimb paralysis, 2.5=bilateral partial hindlimb paralysis, 3.0=complete bilateral hindlimb paralysis, 3.5=complete hindlimb and unilateral partial forelimb paralysis, 4.0=moribund and 5=dead. Ten mice were assigned to each of four groups (vehicle: hamster IgG isotype control; treatment: 145-2C11 IgG and h145FabCSA (trimer); and positive control: interferon-β1a) for a total of 40 mice. Treatment was started at the onset of the first clinical sign of EAE to test the effect of different test articles on the modulation of paralysis. For the vehicle, 145-2C11 IgG and h145FabCSA groups, mice were injected intravenously once daily for five consecutive days at a dose level of 1.0, 0.1 and 1.0 µg/mouse, respectively. For the interferon-β1a group, mice were injected intraperitoneally once daily over the entire treatment period at a dose level of 10,000 units/mouse.

Initially, EAE mice treated with 145-2C11 IgG at a dose level over 0.2 µg/mouse resulted in 50% lethality one day after treatment. Gross necropsy observation showed that all dead mice had enlarged spleens, indicative of a major systemic uncontrolled inflammatory response or cytokine storm. The experimental dose level of the 145-2C11 group was therefore reduced to 0.1 µg per mouse. For the trimeric h145FabCSA group, a dose level 1.0 µg/mouse was conducted for the treatment. The results showed that the trimeric h145FabCSA generated a lower level of paralysis at all stages of the immunization (see FIG. 13A). In particular, mice treated with h145FabCSA showed less paralysis than mice treated with 145-2C11 IgG or the control treated groups, with statistically lower paralysis between the h145FabCSA treated group and the 145-2C11 IgG treated group. Ultimately, the maximum level of paralysis demonstrated by the h145FabCSA treated group was less severe than unilateral hindlimb paralysis (i.e., clinical scale 2), while the untreated group demonstrated symptoms as severe as complete bilateral hindlimb paralysis.

Induction of regulatory T (Treg) cells is one of the major goals for the immunotherapy of autoimmune diseases. Previous studies on orally administered CD3-specific antibody demonstrated that the CD4+CD25-LAP+ Treg cells were induced (Ochi et. al (2006) "Oral CD3-specific antibody suppresses autoimmune encephalomyelitis by inducing CD4+CD25-LAP+ T cells." Nat Med 12(6):627-635). Comparison of the Treg populations in EAE mice after h145-2C-11 IgG and the trimeric h145FabCSA treatment was performed. One day after the last intravenously injection, the spleen lymphoid cells of three mice from each of the vehicle (hamster control IgG), 145-2C11 IgG and the trimeric h145FabCSA group were prepared individually and then stained with LAP-APC and CD4-FITC for flow cytometry. Splenocytes were stained with LAP-APC and CD4-FITC for flow cytometry. Determination of Treg populations was gated on LAP+ cells.

Figure 13:
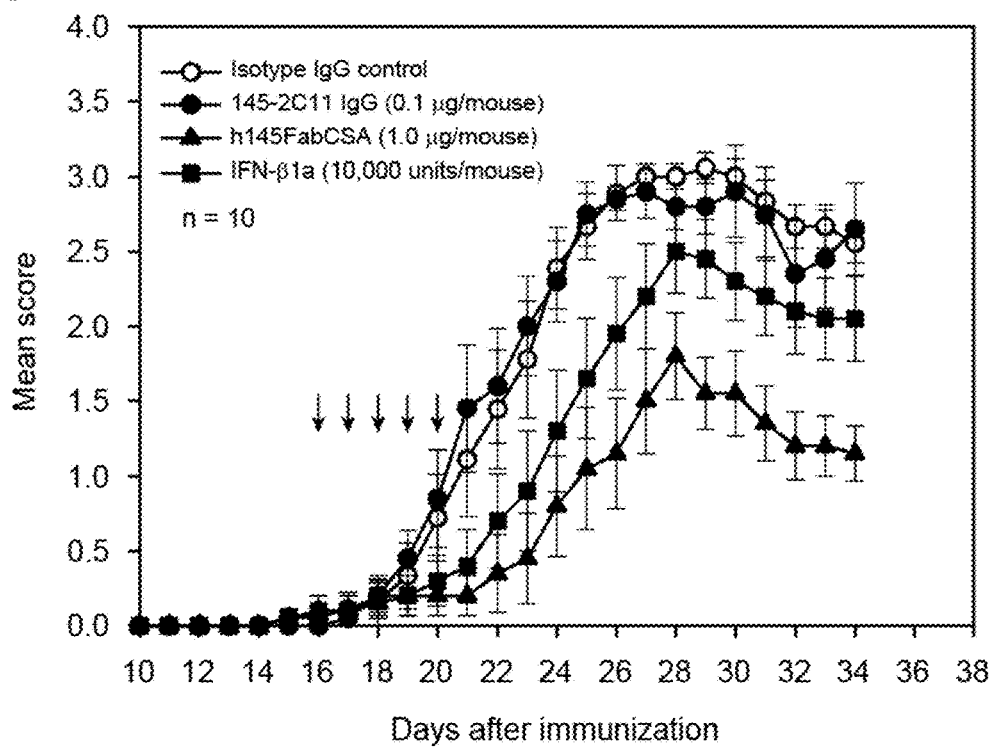
FIG. 13 depicts the biological effects of different anti-mouse CD3 antibodies on experimental autoimmune encephalomyelitis (EAE) mouse disease model according to the embodiments. (A) Efficacy of different biologics on EAE mice. For the vehicle (hamster control IgG), 145-2C11 (hamster IgG) and the purified trimeric h145FabCSA groups, mice were injected intravenously once daily for five consecutive days (indicated by arrows) at a dose level of 1.0, 0.1 and 1.0 µg/mouse, respectively. For the interferon-β1a (positive control) group, mice were injected intraperitoneally once daily over the entire treatment period at a dose level of 10,000 units/mouse. Results are shown as the mean±S.D. for each group (n=10) of a representative experiment from two independent experiments. (B) Flow cytometry of the Treg cell population in response to h145-2C-11 IgG and the trimeric h145FabCSA treatment on EAE mice. One day after the last intravenously injection, the spleen lymphoid cells of three mice from each of the vehicle (hamster control IgG), 145-2C11 IgG and the trimeric h145FabCSA group were prepared individually and then stained with LAP-APC and CD4-FITC for flow cytometry. Determination of Treg populations was gated on LAP+ cells. The data are from one representative mouse in three experiments.
Figure 13:
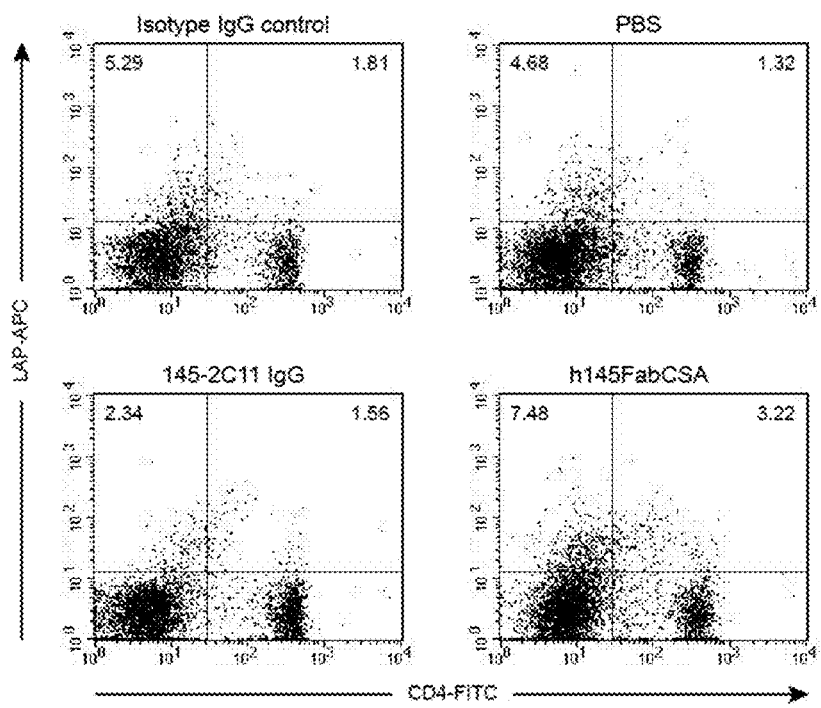

The results indicated that after h145FabCSA treatment, the CD4+LAP+ T cell population was increased in comparison with the isotype IgG control and the 145-2C-11 groups (see FIG. 13B). Notably, the CD4– LAP+ T cell population, which may represent the CD8+LAP+ T cells, was also increased in the h145FabCSA treatment group.

Example 12

Systemic Lupus Erythematosus (SLE) in Mouse Model

Figure 14:
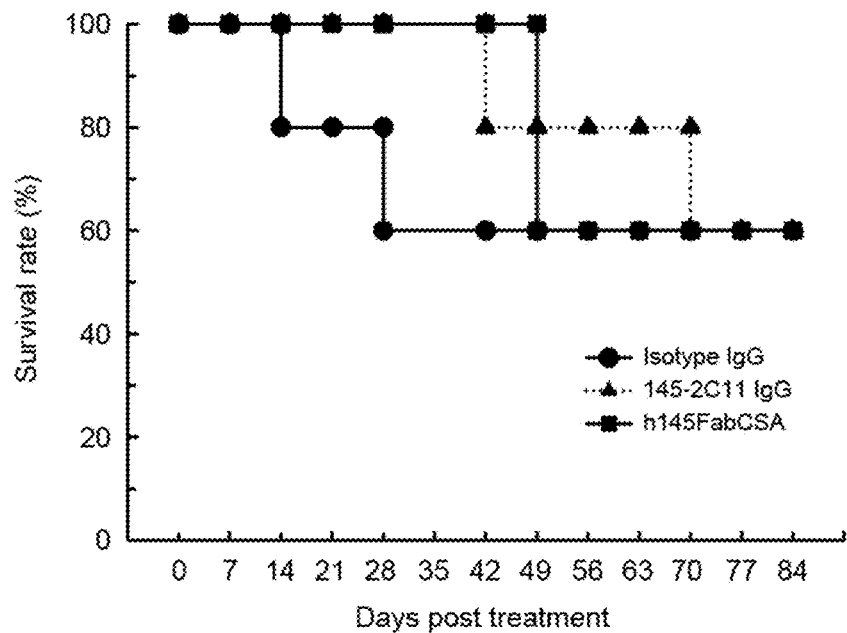
FIGS. 14 A and B depict the therapeutic effect of 145-2C11 IgG and h145FabCSA trimer on SLE mouse model.
Figure 14:
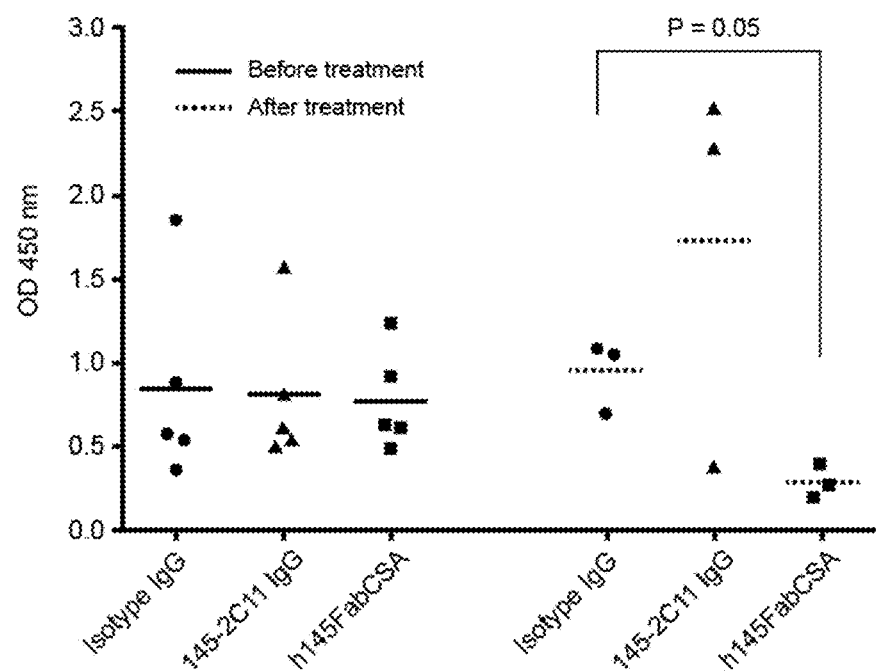

The therapeutic effect of anti-CD3 antibodies of 145-2C11 IgG and h145FabCSA trimer on NZB/W F1 mice with spontaneously developed lupus was investigated. Around 6-month-old female NZB/W F1 mice that had developed spontaneous lupus were treated with six 5-day courses of 5 µg of isotype IgG control, 145-2C11 IgG or h145FabCSA (trimer) every other week by intravenous injection over a 12-week period. As shown in FIG. 14A, the mice treated with h145FabCSA survived longer than those mice treated with the isotype IgG control, indicating that the trimeric h145FabCSA is more effective in treating SLE mouse model than 145-2C11 and the isotype IgG control.

Example 13

Measurement of Mouse Serum Antibodies to Double-Stranded DNA (dsDNA)

When lupus is active, high amounts of serum anti-dsDNA antibodies are present. Therefore, anti-dsDNA autoantibody test was used to measure the disease progression in SLE mouse model. ELISA of mouse sera from the above treatment groups for detection of anti-dsDNA autoantibodies was determined as follows: 96 well polystyrene ELISA plates were coated with 50 µl of methylated bovine albumin from bovine serum (Sigma) (50 µg/ml in distilled water) and incubated for one hour at 37° C. Each well was then washed three times with phosphate buffered saline before the addition of 50 µl of dsDNA (10 µg/ml) in PBS. The dsDNA was prepared by treating calf thymus DNA (Sigma) with 1 U/mg 51 nuclease (Sigma) for 30 minutes at 37° C. After overnight incubation at 4° C. the plates were washed four times with PBS. These were then treated with 100 µl of 2% BSA (Sigma) in PBS to prevent non-specific binding, incubated for one hour at 37° C., and then washed five times with PBS containing 0.05% of TWEEN-20™ (nonionic detergent, Polyethylene glycol sorbitan monolaurate) (PBS-T) (Sigma). Test serum samples were diluted 800-fold in PBS-T and 50 µl aliquots were added to the wells in duplicate. After incubated for one hour at 37° C. the plates were washed six times with PBS-T. For the detection of total IgG antibodies, 50 µl/well of HRP-conjugated rat antimouse antibody (BD Bioscieces) at 5000-fold dilution was added and incubated at 37° C. for one hour. After washing seven times with PBS-T, the reaction was developed using 100 µl/well of tetramethylbenzene (Sigma-Aldrich) at 1 mg/ml in citrate phosphate buffer and stopped by the addition of 50 µl/well of 1 N HCl. Absorbance readings were taken at 450 nm with an ELISA reader.

As shown in FIG. 14B, the level of anti-dsDNA autoantibodies in the h145FabCSA treated mice was significantly lower than that in the control isotype IgG group, and would appear to also be lower than the majority of the animals treated with 145-2C11 IgG. The results indicated that the trimeric h145FabCSA is effective in treating SLE mouse model and no progression of disease over the treatment time course.

Example 14

In Vivo Pro-Inflammatory Cytokine Analysis

Administration of anti-mouse CD3 antibody, 145-2C11, has previously been associated with T cell proliferation and specific cytokine induction including IL-2, IFNγ, TNFα, IL-1β, IL-6, IL-10 and IL17A. Time course studies on serum pro-inflammatory cytokine levels in mice after intravenously injection of a single dose of 50 µg of different anti-CD3 antibodies were conducted to evaluate whether the non-Fc version of h145FabCSA (trimer) is beneficial to therapeutic value with non-mitogenicity. Mice were grouped and administered intravenously with 50 µg of the purified 145-2C11 IgG (light grey squares), the low-Fc binding anti-mouse CD3 antibody—145IgG-AA (dark grey squares), or h145FabCSA trimer (open squares). Blood (100 µl/mouse) was collected at 0 (pre-bleed), 0.5-, 24-, and 144-hour time points. The level of cytokine was determined using ELISA. Each point represents the mean±S.D. of three wells. PBS (black squares) was used as control.

Figure 15:
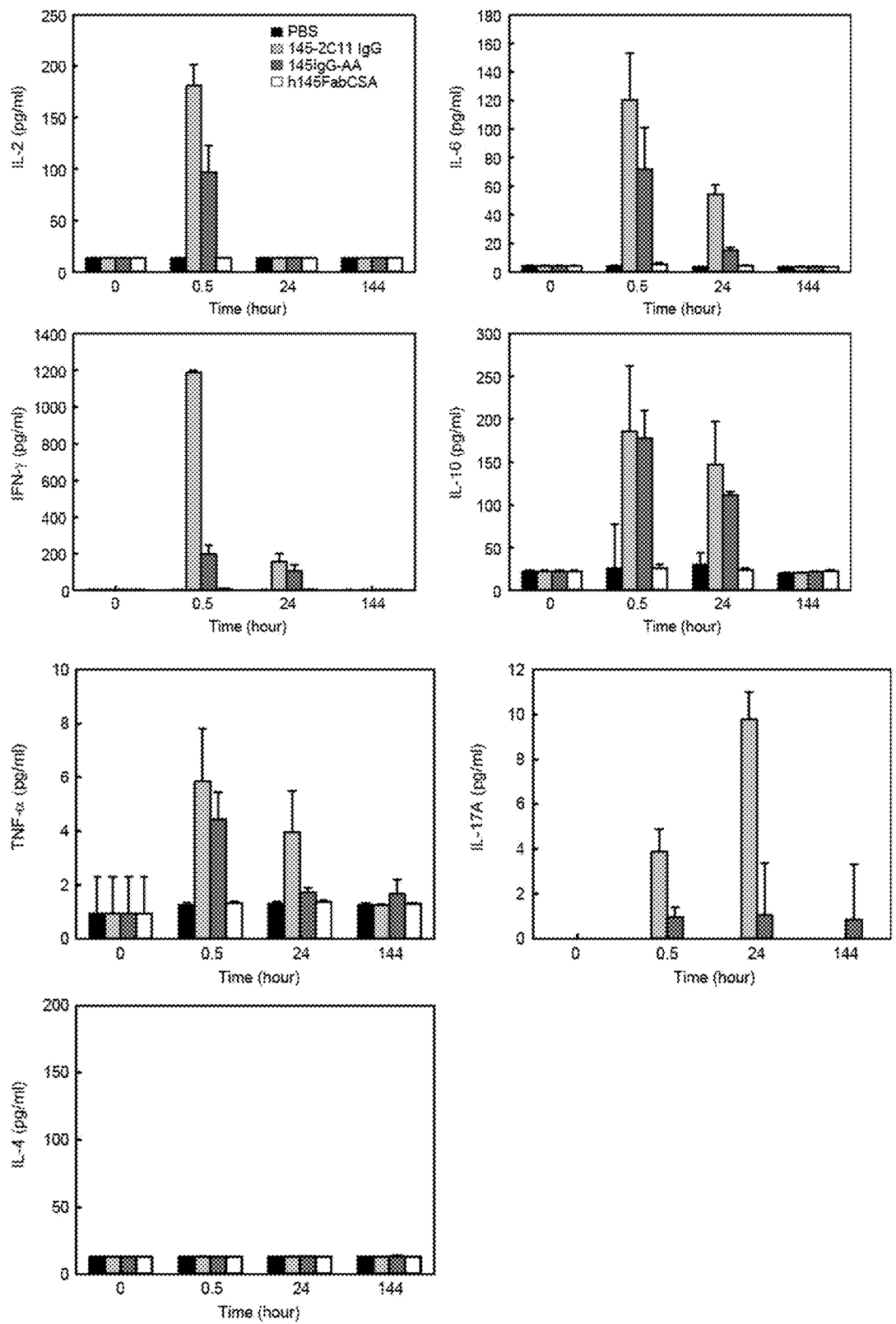
FIG. 15 depicts the time course studies on serum cytokine levels in mice after intravenously injection of a single dose of 50 µg of different anti-mouse CD3 antibodies. Mice were grouped and administered intravenously with 50 µg of the purified 145-2C11 IgG (light grey squares), the low-Fc binding anti-mouse CD3 antibody—145IgG-AA (dark grey squares), or h145FabCSA trimer (open squares). Blood (100 µl/mouse) was collected at 0 (pre-bleed), 0.5-, 24-, and 144-hour time points. The level of cytokine was determined using ELISA. Each point represents the mean±S.D. of three wells. PBS (black squares) was used as control.

Results are shown in FIG. 15. As expected, most cytokines were produced significantly in the 145-2C11 group. The low-Fc binding version of 145IgG-AA results in a moderate transient induction of IL-2, TNFα, IL-6, and IL-10. Administration of the non-Fc version of h145FabCSA (trimer) shows negligible levels of cytokine induction. These results demonstrate that the trimeric h145FabCSA does not induce cytokine production in vivo after first injection.

Example 15

Figure 16:
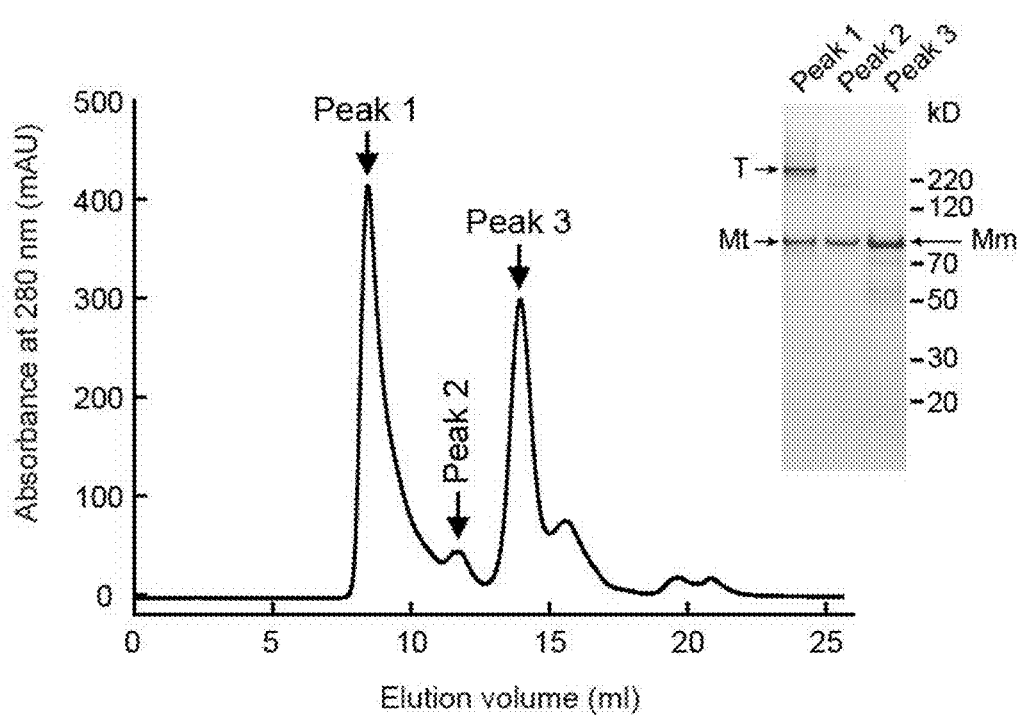
FIG. 16 depicts the structural characterization of the hOKT3FabCSA763scFv molecules derived from a non-single (A) or a single stable clone (B). Each culture media was purified by sequential chromatographies on KappaSelect (an affinity medium designed for the purification of human Fab (kappa) fragments) and SUPERDEX™ 200 column (a prepacked size exclusion chromatography column). (A) Separation of hOKT3FabCSA763scFv species derived from a non-single clone by gel filtration. Upper right panel: different peak fractions (numbered Peaks 1 to 3) were analyzed by SDS-PAGE under nonreducing conditions. The band positions corresponding to the conformation of disulfide linked trimers (T), non-disulfide-bonded trimers (Mt), and monomers (Mm) are indicated by arrows; (B) Separation of hOKT3FabCSA763scFv species derived from a stable clone by gel filtration. The peak fraction was analyzed by SDS-PAGE under non-reducing conditions. The band positions corresponding to the conformation of disulfide linked trimers (T) and non-disulfidebonded trimers (Mt) are indicated by arrows. All samples were electrophoresed on a 4~12% SDS/Bis-Tris polyacrylamide gel with MES as a running buffer. The gels were stained with INSTANT-BLUE™ Protein Stain solution, a Coomassie based solution containing solubilisers, Coomassie Brilliant Blue, phosphoric acid and ethanol, manufactured by Expedeon Ltd.
Figure 16:
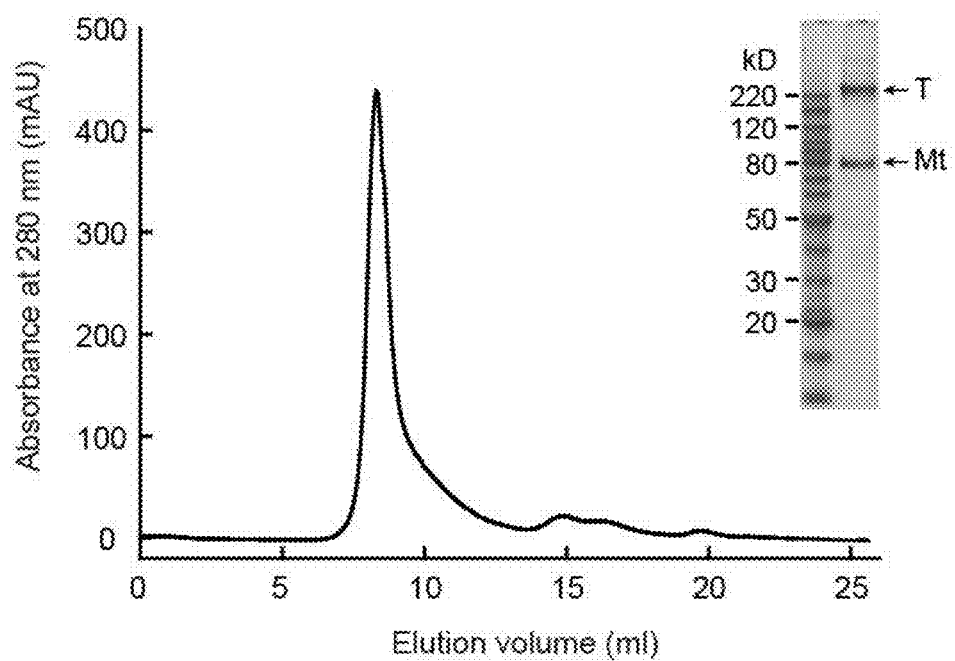

Chromatography and Structure Characterization of a Trivalent Bispecific Anti-CD3×EGFR Antibody, hOKT3FabCSA763scFv The present multivalent antibody fragments are especially feasible for making bispecific antibodies by fusion of two different antibody fragments with a collagen-scaffold at either ends. A trivalent bispecific anti-CD3×EGFR antibody, hOKT3FabCSA763scFv, which targets both CD3 and EGFR, was developed to demonstrate the use of such modality. FIG. 16 depicts the structural characterization of the hOKT3FabCSA763scFv molecules derived from a non-single (A) or a single stable clone (B). Each culture media was purified by sequential chromatographies on KappaSelect and SUPERDEX™ 200 column (a prepacked size exclusion chromatography column). (A) Separation of hOKT3FabCSA763scFv species derived from a non-single clone by gel filtration. Upper right panel: different peak fractions (numbered Peaks 1 to 3) were analyzed by SDS-PAGE under non-reducing conditions. The conformation of disulfide linked trimers (T), non-disulfide-bonded trimers (Mt), and monomers (Mm) are shown; (B) Separation of hOKT3FabCSA763scFv species derived from a stable clone by gel filtration. The peak fraction was analyzed by SDS-PAGE under non-reducing conditions. The conformation of disulfide linked trimers (T) and non-disulfide-bonded trimers (Mt) are shown.

The results demonstrated that in the eukaryotic cell expression system, the collagen-like peptide of the invention is capable of trimerizing an N-terminal Fd fragment and a C-terminal scFv fragment simultaneously. Moreover, the light chain can be assembled with the Fd portion of the trimerized polypeptide chain to form an intact Fab trimer with a structure format shown in FIG. 1B.

Example 16

Figure 17:
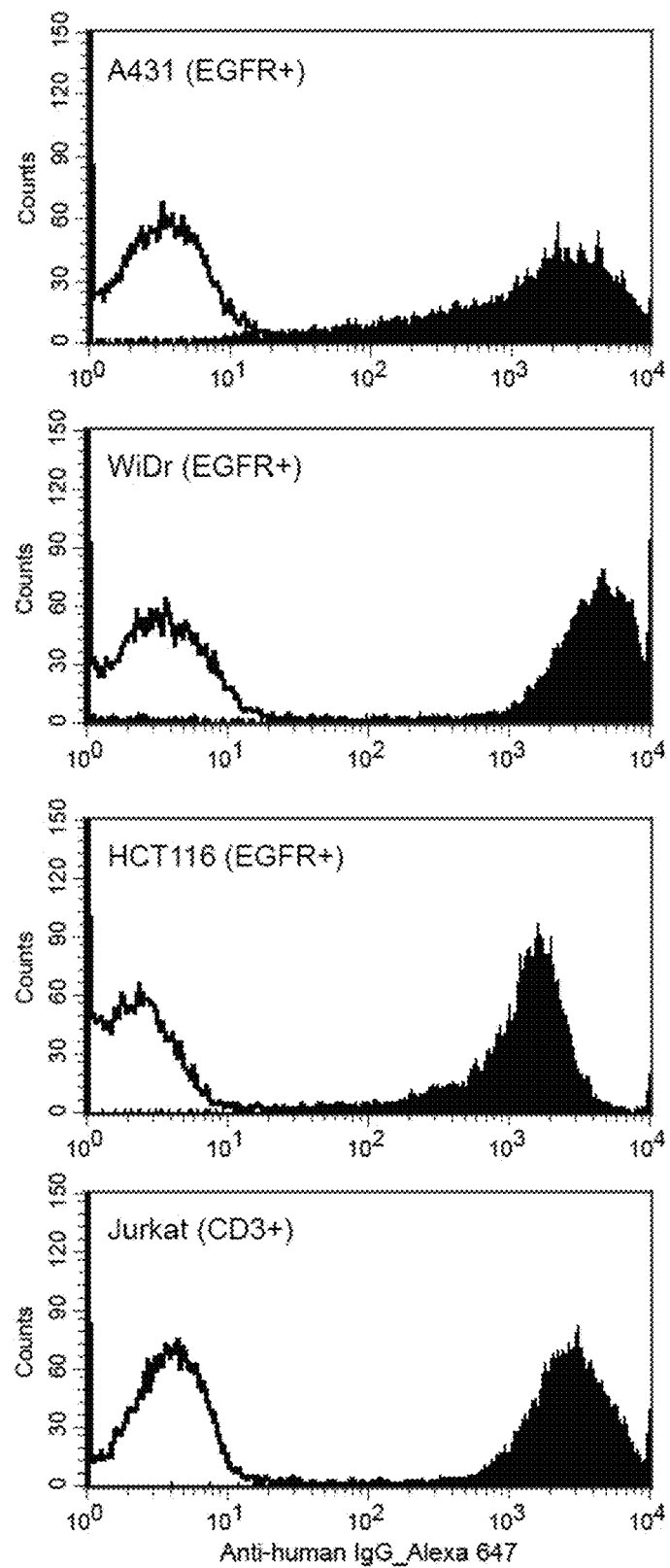
FIG. 17 depicts the flow cytometric analysis of the binding of EGFR(+) cells—A431, WiDr, and HCT116, and the CD3(+) Jurkat T cells with the trimeric bispecific anti-CD3×EGFR antibody, hOKT3FabCSA763scFv, derived from the peak fraction of the trimers containing both of the non-disulfide-bonded and the disulfide linked trimers as shown in FIG. 16B.

Binding Specificity of the Trimeric Bispecific Antibody—hOKT3FabCSA763scFv for EGFR(+) and CD3(+) Cells Binding of hOKT3FabCSA763scFv to each antigen was confirmed by flow cytometry. Strong reactivity was observed with A431, WiDr, and HCT116 cells (EGFR positive) and Jurkat T cells (CD3 positive; FIG. 17).

Example 17

Cytotoxicity Assay

A fluorescence-based Eu TDA nonradioactive cytotoxicity assay (Perkin Elmer, Boston, Mass.) was used to compare the cytotoxic activity of the trimeric hOKT3FabCSA763scFv on different EGFR-bearing tumor cell lines using stimulated human PBMCs as effectors. Human PBMCs from one healthy donor were stimulated by growing cells in an OKT3-coated (2 µg/ml) plate in RPMI+ 10% FBS, containing 50 units/ml (or 0.2 ng/ml) of IL-2 for 72 hours. Around $1 \times 10^6$ of target cells were labeled with DELFIA™ BATDA Reagent (PerkinElmer, a cell marker, which is a non-radioactive label) according to the manufacturer instruction. The cells were washed three times with PBS and then resuspended the Eu3+-labeled target cells in complete culture medium (CM) at a concentration of $5 \times 10^4$ cells/ml. Aliquots 100 µl ($5 \times 10^4$ cells) of target cells into wells of 96-well V-bottom sterile microtiter plates. An equal volume of effector PBMCs was added to each well to give effector/target (E/T) ratios ranging from 50:1 to 2.5:1 for A431 cells and a constant 10:1 for WiDr and HCT116 cells, respectively. The microplates were incubated for 2 h at 37° C. in a humidified hood of 5% $CO_2$. All assays were done in triplicate. After incubation, the plates were centrifuged again, and the supernatants were harvested for measurements of released Eu3+. For the detection of released Eu3+, 20-µl aliquots of the supernatants were transferred to wells of a flat-bottom 96-well microplate, and a 200 µl aliquot of enhancement solution was added to each well.

After mixing for 15 min at room temperature on a rotatory shaker, fluorescence was measured in a time-resolved fluorometer (Hidex, CHAMELEON detection platform, Finland). The percentage of specific cytotoxicity was calculated as (experimental release−spontaneous release)/(maximum release−spontaneous release)×100. Spontaneous release was determined by incubating the target cells with 100 µl of CM instead of effector cells, and maximum release was determined by incubating the targets with 100 µl of lysis buffer (0.5% Triton-X100).

Figure 18:
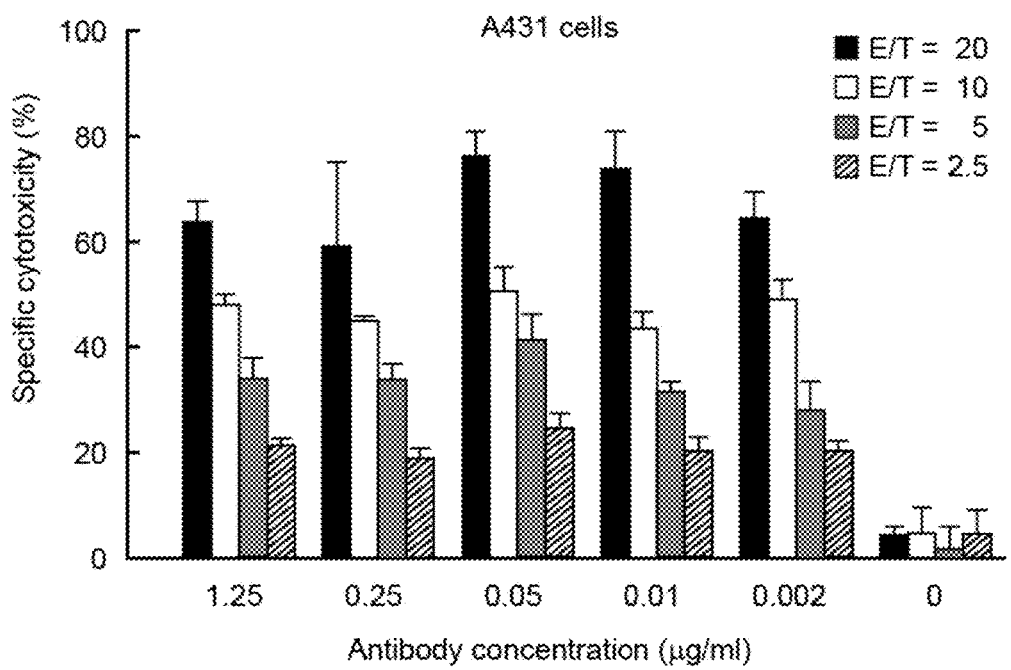
FIG. 18 depicts the cytotoxicity of the trimeric bispecific anti-CD3×EGFR antibody, hOKT3FabCSA763scFv, against EGFR-expressing tumor cells by human PBMCs. Under varying concentrations of the trimeric hOKT3FabCSA763scFv, stimulated human PBMCs were incubated at a different E/T ratio with A431 cells (A); or at a constant 10:1 ratio with WiDr or HCT116 cells (B).
Figure 18:
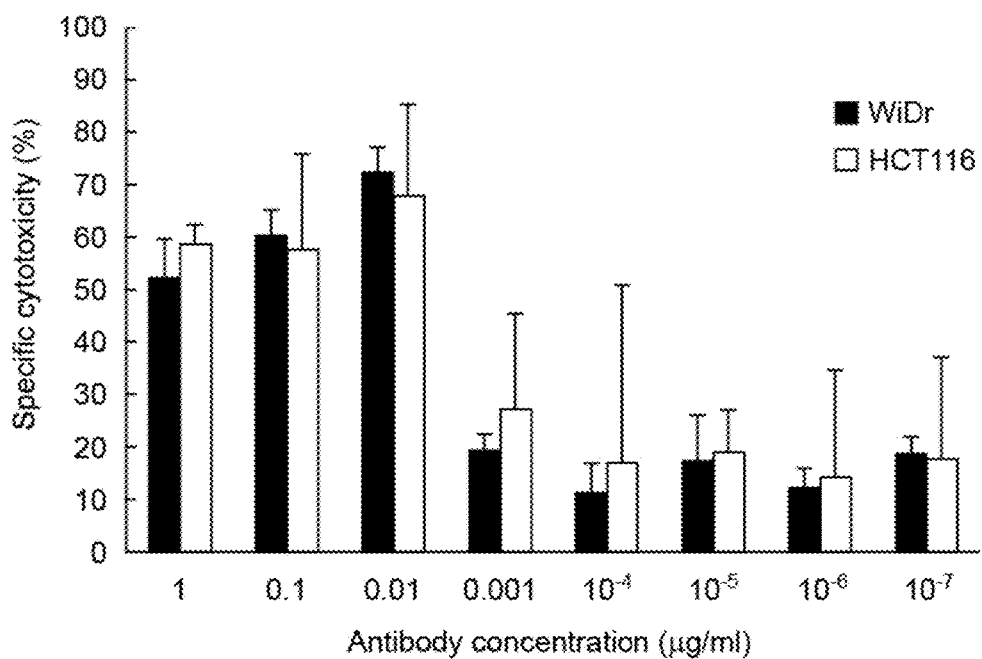

The ability of the trimeric bispecific hOKT3FabCSA763scFv to direct the lysis of different EGFR-expressing tumor cells, including A431, WiDr and HCT116 cell lines, by human PBMCs was evaluated. FIG. 18 depicts the specific cytotoxicity of varying concentrations of the trimeric hOKT3FabCSA763scFv toward A431 cells with different E/T ratios (A); and WiDr or HCT116 cells with a constant E/T ratio of 10:1 (B). Lysis of EGFR-overexpressing A431 tumor cells in the presence of stimulated human PMBCs was specifically triggered by the trimeric bispecific hOKT3FabCSA763scFv in a dose and E/T ratio-dependent manner (FIG. 18A). This resulted in a maximal of ~80% of specific killing at a hOKT3FabCSA763scFv concentration level of 0.05 µg/ml with an E/T ratio of 20:1 (filled squares). In the absence of hOKT3FabCSA763scFv, stimulated human PMBCs alone could not kill A431 cells effectively. Similar results were obtained by incubating either WiDr or HCT116 cell line with the trimeric hOKT3FabCSA763scFv at a fixed E/T ration of 10:1 (FIG. 18B). These results demonstrated that the trimeric hOKT3FabCSA763scFv can effectively direct the lysis of EGFR-bearing tumor cells by human PBMCs (presumably cytotoxic T cells).

Example 18

Time Lapse Microscopy

Figure 19:
FIG. 19 depicts the time-lapse photography of the redirected lysis of EGFR-overexpressing tumor cells by the trimeric bispecific hOKT3FabCSA763scFv. A431 cells was co-cultured with PKH26-prestained human T lymphocytes in the absence (A), or in the presence (B) of 1 µg/ml of the trimeric hOKT3FabCSA763scFv for indicated time points (hour:minute) and images were recorded by time-lapse microscopy, respectively. Note the completion of apoptosis of the A431 cells by T cells was observed after 13 hours of co-culture.
Figure 19:
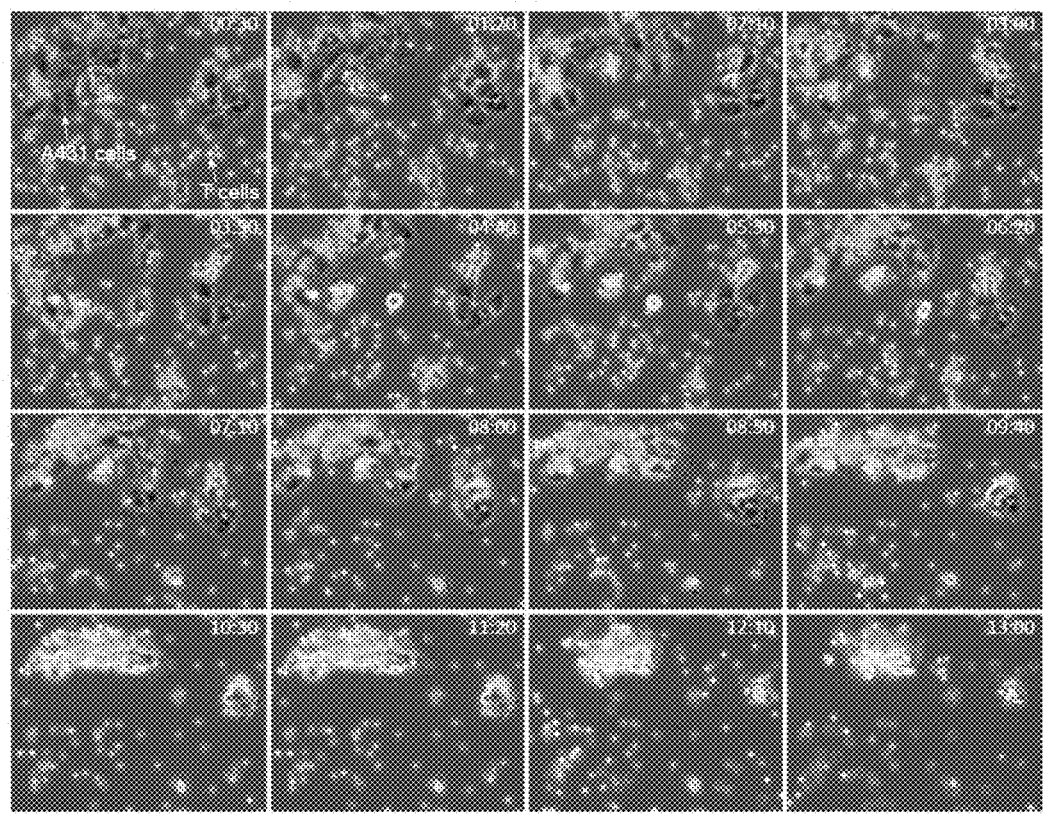

The time lapse microscopy photography in FIG. 19 further demonstrates the redirecting of human cytotoxic T lymphocytes for tumor-cell lysis by the trimeric hOKT3FabCSA763scFv. The trivalent hOKT3FabCSA763scFv can transiently link a T cell and a tumor cell by simultaneously binding CD3 and a target antigen—EGFR, respectively. This will trigger T-cell activation, followed by attacking the crosslinked tumor cell. The attached tumor cell undergoes programmed cell death (apoptosis). The free available T-cell can redirect to another tumor cell and engage the killing event by crosslinking with another hOKT3FabCSA763scFv. In the absence of hOKT3FabCSA763scFv, human T lymphocytes did not affect the tumor cell A431 growth. In FIG. 19B, in the presence of the trimeric hOKT3FabCSA763scFv, human T lymphocytes and A431 cells were crosslinked. T lymphocytes were activated and start attacking tumor cells. In 13 hours of culturing time, most of tumor cells were lysed through apoptosis pathway. In the absence of hOKT3FabCSA763scFv, no crosslinking between A431 cells and T lymphocytes were observed even after 24 hours of co-culturing time (FIG. 19A).

Example 19

Tumor Xenograft Mouse Model

In vivo studies to evaluate antitumor activity were done in 8- to 10-week-old, female NOD/SCID mice (NOD.CB17-Prkdc$^{scid}$/JNarl, National Laboratory Animal Center, Taiwan). Unstimulated human PBMCs (effector) from one healthy donor and premixed with HTC116 tumor cells (target) followed by subcutaneous injection of cell mixes into NOD/SCID mice on day 0. A low 1:1 (effector-to-target) ratio of cells was used. The indicated doses of hOKT3FabCSA763scFv or PBS vehicle control were administered via tail vein injections once daily starting on day 1, for 10 consecutive days. Progress of tumors was determined twice weekly by external caliper measurements, and tumor volumes were calculated using a standard hemiellipsoid formula: (length×width)/2.

Figure 20:
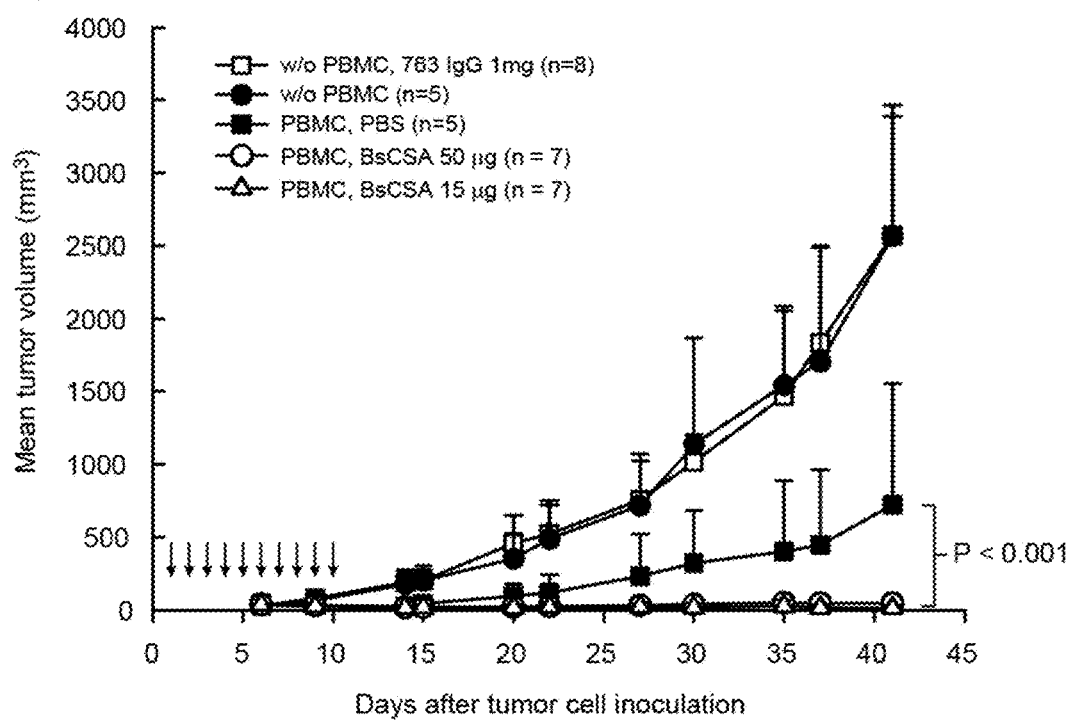
FIG. 20 depicts the in vivo efficacy of the trimeric hOKT3FabCSA763scFv in HCT116 colon cancer NOD/

Results are shown in FIG. 20. FIG. 20 depicts the antitumor effect of the trimeric hOKT3FabCSA763scFv in HCT116 colon cancer NOD/SCID mouse model. Two groups of NOD/SCID mice were inoculated subcutaneously with $5\times10^6$ HCT116 cells in the absence of human PBMC (anti-EGFR 763 IgG and PBS control). The remaining three groups were s.c. injected with mixtures of $5\times10^6$ HCT116 cells and $5\times10^6$ unstimulated human PBMCs from a healthy donor. PBS vehicle control (100 µl), 50 µg and 15 µg of the trimeric hOKT3FabCSA763scFv were administered via tail vein injections on day 1 for 10 consecutive days after HCT116 cell inoculation on day 0. Tumor growth curves derived from each group with the indicated n numbers of animals are shown.

Statistically significant difference ($P<0.001$) between the dosing of the trimeric hOKT3FabCSA763scFv groups and the unstimulated human PBMC control group is shown. The results indicated that the bispecific anti-CD3×EGFR antibody of hOKT3FabCSA763scFv can effectively diminish tumor growth in the presence of human PBMC.

It will be apparent to those skilled in the art that various modifications and variations can be made to the disclosed embodiments. It is intended that the specification and examples be considered as exemplary only, with a true scope of the disclosure being indicated by the following claims and their equivalents.

The invention claimed is:

1. A method for producing a multivalent Fab fragment comprising the steps of
  (i) co-expressing in an isolated host cell:
    (1) a first nucleic acid coding for an amino acid sequence comprising, in an N-terminal to C-terminal direction, a signal peptide, a humanized OKT3 heavy chain variable region, a CH1 region of human IgG, a hinge region, SEQ ID NO: 32 and a collagen-like peptide, wherein the hinge region consists of SEQ ID NO: 19, wherein the nucleotides coding for the hinge region are directly linked to the nucleotides coding for SEQ ID NO: 32,
    wherein the nucleotides coding for SEQ ID NO: 32 are directly linked to the nucleotides coding for the collagen-like peptide; and
    (2) a second nucleic acid coding for an amino acid sequence comprising, in an N-terminal to C-terminal direction, a signal peptide, a humanized OKT3 light chain variable region and a kappa light chain constant domain of human IgG; and
  (ii) allowing polypeptides expressed in the isolated host cell from the first nucleic acid and the second nucleic acid to trimerize into one or more multivalent Fab fragments.

2. The method according to claim 1, wherein the first nucleic acid further comprises a sequence coding for a single chain Fv after the sequence that encodes the collagen-like peptide.

3. A trimeric, multivalent Fab fragment comprising (1) three identical heavy chains each comprising an amino acid sequence comprising, in an N-terminal to C-terminal direction, a humanized OKT3 heavy chain variable region, a CH1 region of human IgG, a hinge region, SEQ ID NO: 32, and a collagen-like peptide, wherein the hinge region consists of SEQ ID NO: 19, wherein the amino acid sequence of SEQ ID NO: 19 is directly linked to the amino acid sequence of SEQ ID NO: 32, wherein the amino acid sequence of SEQ ID NO: 32 is directly linked to the collagen-like peptide; and (2) three identical light chains each comprising an amino acid sequence comprising, in an N-terminal to C-terminal direction, a humanized OKT3 light chain variable region and a kappa light chain constant domain of human IgG.

4. An isolated nucleic acid encoding the heavy chains and light chains of the trimeric, multivalent Fab fragment of claim 3.

5. An isolated expression vector comprising the nucleic acid of claim 4.

6. An isolated host cell comprising the expression vector of claim 5.

7. The method for producing a multivalent Fab fragment of claim 1, wherein the second nucleic acid (2) codes for an amino acid sequence consisting of, from N-terminus to C-terminus, the signal peptide, the humanized OKT3 light chain variable region and the kappa light chain constant domain of human IgG.

8. The method for producing a multivalent Fab fragment of claim 1, wherein the first nucleic acid codes for an amino acid sequence consisting of from N-terminus to C-terminus, the signal peptide, the humanized OKT3 heavy chain variable region, the CH1 region of human IgG, the hinge region, SEQ ID NO: 32, and the collagen-like peptide.

9. The method for producing a multivalent Fab fragment of claim 1, wherein, in the first nucleic acid, the nucleotides coding for the collagen-like peptide code for the peptide set forth in SEQ ID NO: 27.

10. The method for producing a multivalent Fab fragment of claim 1, further comprising (iii) a purification step comprising an anti-human kappa light chain binding column chromatography.

11. A method for producing a multivalent Fab fragment comprising the steps of
  (i) co-expressing in an isolated host cell:
    (1) a first nucleic acid coding for the amino acid sequence set forth in SEQ ID NO: 5; and (2) a second nucleic acid coding for the amino acid sequence set forth in SEQ ID NO: 7; and (ii) allowing polypeptides expressed in the isolated host cell from the first nucleic acid and the second nucleic acid to trimerize into one or more multivalent Fab fragments.

12. Isolated nucleic acids, consisting of:

(1) a first nucleic acid coding for the amino acid sequence set forth in SEQ ID NO: 5; and (2) a second nucleic acid coding for the amino acid sequence set forth in SEQ ID NO: 7.

\* \* \* \* \*